ial*

(12) United States Patent
Hedtjarn

(10) Patent No.: US 8,450,291 B2
(45) Date of Patent: May 28, 2013

(54) RNA ANTAGONIST COMPOUNDS FOR THE MODULATION OF PIK3CA EXPRESSION

(75) Inventor: Maj Hedtjarn, Copenhagen (DK)

(73) Assignee: Santaris Pharma A/S, Horsholm (DK)

( * ) Notice: Subject to any disclaimer, the term of this patent is extended or adjusted under 35 U.S.C. 154(b) by 281 days.

(21) Appl. No.: 12/947,865

(22) Filed: Nov. 17, 2010

(65) Prior Publication Data
US 2011/0077285 A1   Mar. 31, 2011

Related U.S. Application Data

(62) Division of application No. 12/323,744, filed on Nov. 26, 2008, now Pat. No. 7,863,437.

(60) Provisional application No. 60/992,050, filed on Dec. 3, 2007.

(51) Int. Cl.
*C12N 15/00* (2006.01)

(52) U.S. Cl.
USPC ..................................................... 514/44 A

(58) Field of Classification Search
USPC ..................................................... 514/44 A
See application file for complete search history.

(56) References Cited

U.S. PATENT DOCUMENTS

| 4,914,210 | A | 4/1990 | Levenson et al. |
|---|---|---|---|
| 4,962,029 | A | 10/1990 | Levenson et al. |
| 7,087,229 | B2 | 8/2006 | Zhao et al. |
| 2004/0235773 | A1 | 11/2004 | Zhao et al. |
| 2005/0272682 | A1 | 12/2005 | Evers et al. |
| 2006/0030536 | A1 | 2/2006 | Yu et al. |

FOREIGN PATENT DOCUMENTS

| EP | 1222309 | 12/2005 |
|---|---|---|
| WO | 2004046160 | 6/2004 |
| WO | 2005091849 | 10/2005 |
| WO | 2007031081 | 3/2007 |
| WO | 2007031091 | 3/2007 |
| WO | 2007107162 | 9/2007 |
| WO | 2007136758 | 11/2007 |
| WO | 2008034122 | 3/2008 |
| WO | 2008034123 | 3/2008 |

OTHER PUBLICATIONS

Akinc, et al., "A combinatorial library of lipid-like materials for delivery of RNAi therapeutics," Nature Biotechnology, 26:561-569, 2008.
Freier & Altmann; "The ups and downs of nucleic acid duplex stability: structure-stability studies on chemically-modified DNA:RNA duplexes," Nucl. Acid Research, 25:4429-4443, 1997.
Hsieh et al, "A library of siRNA duplexes targeting the phosphoinositide 3-kinase pathway: determinants of gene silencing for use in cell-based screens," NAR 32:893-901, 2004.
Manoharan et al., "Novel Functionalization of the Sugar Moiety of Nucleic Acids for Multiple Labeling in the Minor Groove," Tetrahedron Letters 32:7171-7174, 1991.
Meng, et al., "Role of PI3K and AKT specific isoforms in ovarian cancer cell migration, invasion and proliferation through the p70S6K1 pathway," Cellular Signalling 18:2262-2271, 2006.
Rychahou et al., "Targeted Molecular Therapy of the PI3K Pathway: Therapeutic Significance of PI3K Subunit Targeting in Colorectal Carcinoma," Annals of Surgery 243:833-844, 2006.
Samuels et al., "Oncogenic PI3K and its role in cancer," Curr. Opin. Oncol. 18:77-82, 2006.
Uhlmann, Eugen, "Recent advances in the medicinal chemistry of antisense oligonucleotides," Curr. Opinion in Drug Development 3:203-213, 2000.
Zhang et al., "A Potential Strategy for Isoform-Specific Phosphatidylinositol 3-Kinase Targeted Therapy in Ovarian Cancer," Cancer Biology and Therapy, 3:1283-1289, 2004.
Zhao et al., "A New Platform for Oligonucleotide Delivery Utilizing the PEG Prodrug Approach," Bioconjugate Chemistry 16:758-766, 2005.
Zhao et al., "Delivery of G3139 using releasable PEG-linkers: Impact on pharmacokinetic profile and anti-tumor efficacy," J. of Controlled Release 119:143-152, 2007.
Broderick, D. et al., "Mutations of PIK3CA in anaplastic oligodendrogliomas, high-grade astrocytomas, and medulloblastomas". Cancer Research 64:5048-5050, 2004.
Kurreck et al., "Design of antisense oligonucleotides stabilized by locked nucleic acids". Nucleic Acids Research 30:1911-1918, 2002.
International Search Report issued in PCT/DK2008/000418 and dated Jun. 8, 2009.

*Primary Examiner* — Brian Whiteman
(74) *Attorney, Agent, or Firm* — Fish & Richardson P.C.

(57) ABSTRACT

The invention relates to oligomeric compounds (oligomers), which target PIK3CA mRNA in a cell, leading to reduced expression of PIK3CA. Reduction of PIK3CA expression is beneficial for the treatment of certain medical disorders, such as hyperproliferative diseases (e.g., cancer). The invention provides therapeutic compositions that include the oligomers and methods for modulating the expression of PIK3CA using the oligomers, including methods of treatment.

14 Claims, 22 Drawing Sheets

FIGURE 3

```
                    1                                                  50
NM_006218     (1)   TCTCCCTCGGCGCCGCCGCCGCCGCCCGCGGGGCTGGGACCCGATGCGGT
NM_008839     (1)   --------------------------------------------------
Consensus     (1)
                    51                                                 100
NM_006218    (51)   TAGAGCCGCGGAGCCTGGAAGAGCCCCGAGCGTTTCTGCTTTGGCACAAC
NM_008839     (1)   --------------------------------------------------
Consensus    (51)
                    101                                                150
NM_006218   (101)   CATACATCTAATTCCTTAAAGTAGTTTTATATGTAAAACTTGCAAAGAAT
NM_008839     (1)   --------------------------------------------------
Consensus   (101)
                    151                                                200
NM_006218   (151)   CAGAACAATGCCTCCACGACCATCATCAGGTGAACTGTGGGGCATCCACT
NM_008839     (1)   ------ATGCCTCCACGACCATCTTCGGGTGAACTGTGGGGCATCCAC
Consensus   (151)         ATGCCTCCACGACCATC TC GGTGAACTGTGGGGCATCCACT
                    201                                                250
NM_006218   (201)   TGATGCCCCCAAGAATCCTAGTAGAATGTTTACTACCAAGATGGATGATA
NM_008839    (44)   TGATGCCCCCACGAATCCTAGTGGAATGTTTAGTCCCAATGGATGATA
Consensus   (201)   TGATGCCCCCA GAATCCTAGT GAATGTTTACT CC AATGGAATGATA
                    251                                                300
NM_006218   (251)   GTGACTTTAGAATGCCTCCGTGAGGCTAGATTAATAAGCATAACATGA
NM_008839    (94)   GTGACTTTAGAATGCCTCCGTGAGGCCACACTCGTCACCATCATAATGA
Consensus   (251)   GTGACTTTAGAATGCCTCCGTGAGGC ACA T  T ACCAT AA CATGA
                    301                                                350
NM_006218   (301)   ACTATTTAAAGAAGCAAGAAAATACCCTCCTCCATCAACTTCTTGAGATC
NM_008839   (144)   ACTGTTCAGAGAGGTCAGGAAATACCCTCCCATCAGCTTCTGAAGACG
Consensus   (301)   ACT TT A AGA GC AG AAATACCC CTCCATCA CTTCT CAAGA G
                    351                                                400
NM_006218   (351)   AATCTTCTACATTTTCGTAAGTGTTACTCAAGAAGCAGAAAGGGAAGAA
NM_008839   (194)   AAACTTCTTACATTTTCGTAAGTGTCAGCCAAGAAGCAGAAAGCGAAGAT
Consensus   (351)   AA CTTCTTACATTTTCGTAAGTGT AC CAAGAAGCAGAAAGGGAAGAA
                    401                                                450
NM_006218   (401)   TTTTTTGATGAAACAAGACGACTTTGTGACCTTCGGCTTTTTCAACCCTT
NM_008839   (244)   TTTTTTCATGAAACAAGACGACTTTGTGGCCTTTTTCAACCCTT
Consensus   (401)   TTTTTTGATGAAACAAGACGACTTTGTGACCTTCGGCTTTTTCAACCCTT
                    451                                                500
NM_006218   (451)   TTTAAAAGTAATTGAACCAGTAGGCAAGCGTGAAGAAAAGATCCTCAATC
NM_008839   (294)   TTTAAAAGTTATTGAACCAGTAGGCAACCGTGAAGAAAAGATCCTCAATC
Consensus   (451)   TTTAAAAGT ATTGAACCAGTAGGCAACCGTGAAGAAAAGATCCTCAATC
                    501                                                550
NM_006218   (501)   GAGAAATTGGTTTTGCTATCGGCATGCCAGTGTGTGAATTTGATATGGTT
NM_008839   (344)   GAGAAATTGGTTTTGTTATTGGCATGCCAGTGTGTGAATTTGATATGGTT
Consensus   (501)   GAGAAATTGGTTTTG TAT GGCATGCCAGTGTGTGAATTTGATATGGTT
                    551                                                600
NM_006218   (551)   AAAGATCCAGAAGTACAGGACTTCGAAGAAATATTCTGAACGTTGTAA
NM_008839   (394)   AAAGATCCAGAAGTCAAGACTTTCGAAGGAACATTCTGAATGTTCCAA
Consensus   (551)   AAAGATCCAGAAGT CA GACTT CGAAG AA ATTCTGAA GTTTG AA
                    601                                                650
NM_006218   (601)   AGAAGCTGTGGATCTTAGGCACCTGAATTCACCTCATAGTAGAGCAATGT
NM_008839   (444)   AGAAGCTCCGCACCTGCGGGATCTGAACTGGCCTCATAGCAGAGCAATGT
Consensus   (601)   AGAAGCTGTGGA CT  GGGA CTCAA TC CCTCATAG AGAGCAATGT
                    651                                                700
NM_006218   (651)   ATGTCTATCCTCCAAATGTAGAATCTTCACCAGAATTGCCAAAGCACATA
NM_008839   (494)   ATGTCTACCCTCCAAATGTCGAGTCTTCCCAGAACTGCCAAAGCACATC
Consensus   (651)   ATGTCTA CCTCCAAATGT GA TCTTC CCAGAA TGCCAAAGCACAT
                    701                                                750
NM_006218   (701)   TATAATAAATTAGATAAAGGGCAAATAATAGTGGTCATCTGGGTAATAGT
NM_008839   (544)   TACAACAAGTTAGATAAAGGACAAATCATAGTGGTGATTGGGTAATAGT
Consensus   (701)   TA AA AA TTAGATAAAGG CAAAT ATAGTGGTGAT TGGGTAATAGT
                    751                                                800
NM_006218   (751)   TTCTCCAAATAATGACAAGCAGAAGTATACTCTGAAATCAACCATGACT
NM_008839   (594)   CTCTCCAAACAACGACAAGCAGAAGTACACTCTGAAGATCAATCATGACT
Consensus   (751)    TCTCCAAA AA GACAAGCAGAAGTA ACTCTGAA ATCAA CATGACT
                    801                                                850
NM_006218   (801)   GTGTACCAGAACAAGTAATTGCTGAAGCAATCAGGAAAAAACTCGAAGT
NM_008839   (644)   GTGTGCCAGAGCAAGTCATTGCTGAAGCCATCAGGAAAAAGACTCGGAGC
Consensus   (801)   GTGT CCAGA CAAGT ATTGCTGAAGC ATCAGGAAAAA ACTCG AG
                    851                                                900
NM_006218   (851)   ATGTTGCTATCCTCTGAACAACTAAAACTCTGTGTTTTAGAATATCAGGG
NM_008839   (694)   ATGTTGTGTGTCCTGAGCAGCTGAAACTCTGTGTCCTTAGAATATCAGGG
Consensus   (851)   ATGTTG T  CCTCTGA CA CT AAACTCTGTGT TTAGAATATCAGGG
                    901                                                950
NM_006218   (901)   CAAGTATATTTTAAAGTGTGTGGATGTGATGAATACTTCCTAGAAAAAT
NM_008839   (744)   CAAGTATATTCTGAAGTGTGTGGCCTGAGAATACTTCCTGAAAAGT
Consensus   (901)   CAAGTATATT T AAAGTGTGTGG TCTGA GAATACTTCCT GAAAA T
                    951                                               1000
NM_006218   (951)   ATCCTCTGAGTCAGTATAAGTAATAAGAAGCTGTATAATGCTTGGGAGG
NM_008839   (794)   ACCCTCTGAGTCAGTACATAAGTACATAAGAAGCTGTATAATGCTGGGAGG
Consensus   (951)   A CCTCTGAGTCAGTA AAGTA ATAAGAAGCTGTATAATGCT GGGAGG
                    1001                                              1050
NM_006218  (1001)   ATGCCCAATTTGATGTTGATGGCTAAAGAAAGCCTTTATTCCCAACTGCC
NM_008839   (844)   ATGCCCAACTTGATGCTGATGGCCAAAGAAAGCCTATACTCCCAGCTGCC
```

FIGURE 3 (cont'd)

```
Consensus   (1001) ATGCCCAA TTGATG TGATGGC AAAGAAAGCCT TA TCTCA CTGCC
                   1051                                                1100
NM_006218   (1051) AATGGACTGTCTTAAATGCCATCTTATTCCAGACGCATTCCACAGCTA
NM_008839    (894) GAATGATAGCTCCACCATGCCTCATCTGCAGGCGCATCTCCACAGGCA
Consensus   (1051)   AT GA  G TT AC ATGCC TC TA TCCAG CGCAT TCCACAGC A
                   1101                                                1150
NM_006218   (1101) CACCAATATATGAATGGAGAAACATCTACAAAATCCCTTTGGGTTATAAAT
NM_008839    (944) CACCCTACATGAATGGAGAGACATCTACGAAATCCCTCTGGTTCATAAAT
Consensus   (1101) CACC TA ATGAATGGAGA ACATCTAC AAATCCCT TGGGT ATAAAT
                   1151                                                1200
NM_006218   (1151) AGTGCACTCCAGAATAAAAATTCTTTGTGCAACCTACCTGAATGTAAATAT
NM_008839    (994) AGTGCGCTCAGAATAAAAATTCTTTGTGCAACCTATGTAAATGTAAATAT
Consensus   (1151) AGTGC CTCAGAATAAAAATTCTTTGTGCAACCTA GT AATGTAAATAT
                   1201                                                1250
NM_006218   (1201) TCGAGACACATTGATAACATCTATGTTCGAACAGGTATCTACCATGGAGGAG
NM_008839   (1044) TCGAGACATTGATAAGATCTATGTTCGAACAGGTATCTACCAGGCAGGAG
Consensus   (1201) TCGAGACATTGATAAGATCTATGTTCGAACAGGTATCTACCATGGAGGAG
                   1251                                                1300
NM_006218   (1251) AACCCTTATGTGACAATGTGAACGCTCAAAGAGTACCTTGTTCCAATCGC
NM_008839   (1094) AACCCTTATGTGACAATGTGAACACTCAAAGAGTACCTTGTTCCAATCGT
Consensus   (1251) AACCCTTATGTGACAATGTGAACAC CAAAGAGTACCTTGTTCCAATC
                   1301                                                1350
NM_006218   (1301) AGGTGGAATGAATGGCTGAATTATGATATATACATTCCTGATCTTCCTCG
NM_008839   (1144) AGGTGGAATGAATGGCTGAATTATGATATATACATTCCTGATCTTCCTCG
Consensus   (1301) AGGTGGAATGAATGGCTGAATTATGATATATACATTCCTGATCTTCCTCG
                   1351                                                1400
NM_006218   (1351) TGCTGCTCGACTTTGCCTTTCCATTTGCTCTGTTAAAGGCCGAAACGGTG
NM_008839   (1194) TCTCGCCGCCCTTTGCCTTTCAATCTGCTCTGTTAAAGGCCGAAACGGTG
Consensus   (1351) T    GC CG CTTTGCCTTTC AT TGCTCTGTTAAAGGCCGAAACGGTG
                   1401                                                1450
NM_006218   (1401) CTAAAGAGGAACACTGTCCAATGGCAGGGGAAATATAAACTTGTTTGAT
NM_008839   (1244) CTAACGAGGACCACTGTCCGTTGGCCTGGGGAAACATAAACTTGTTTGAT
Consensus   (1401) CTAA GAGGA CACTGTCC TTGGC TCGGGAAA ATAAACTTGTTTGAT
                   1451                                                1500
NM_006218   (1451) TACACAGACACTCTAGTATCTGGAAAAATGGCTTTGAATCTTTGGCCAGT
NM_008839   (1294) TATACAGACACCCTAGTGTCCGGGAAAATGGCTTTGAATCTCTGGCTGT
Consensus   (1451) TA ACAGACAC CTAGT TC GG AAAATGGCTTTGAATCT TGGCC GT
                   1501                                                1550
NM_006218   (1501) ACCTCATGGATTAGAAGATTGCTGAACCCTATTGGTGTTACTGGATCAA
NM_008839   (1344) ACCGCATGGCTTAGAAGATCTGCTGAACCCTATTGGTGTTACTGGCTCAA
Consensus   (1501) ACC CATGG TTAGAAGAT TGCTGAACCCTATTGGTGTTACTGG TCAA
                   1551                                                1600
NM_006218   (1551) ATCCAAATAAAGAAACTCCATGCTTAGAGTTGGACTTTGACTGGTTCAGC
NM_008839   (1394) ATCCAAATAAAGAAAGTCCATGCTTAGAGTTGGAGTTCGATTGGTCAGC
Consensus   (1551) ATCCAAATAAAGAAACTCCATGCTTAGAGTTGGAGTTTGA TGGTTCAGC
                   1601                                                1650
NM_006218   (1601) AGTGTGGTAAAGTTCCAGATATGTCAGTGATTGAACAGCATGCCAATTG
NM_008839   (1444) AGTGTCGTGAAGTTTCCAGACATGTCTGTGAATCGAACGAACATGCCAATTG
Consensus   (1601) AGTGTGGT AAGTT CCAGA ATGTC GTGAT GAAGA CATGCCAATTG
                   1651                                                1700
NM_006218   (1651) CTCTGTATCCCGAGAAGCAGGATTTAGCTATTCCCACGAGGACTGAGTA
NM_008839   (1494) GTCCGTGTCCCGAGAAGCTGGATTCAGTTACTCCCATACAGGACTGAGTA
Consensus   (1651) GTC GT TCCCGAGAAGC GGATT AG TA TCCCA CAGGACTGAGTA
                   1701                                                1750
NM_006218   (1701) ACAGACTAGCTAGAGACAATGAATTAAGCGTAAAATGACAAAGAACAGCTC
NM_008839   (1544) ACAGACTAGCCAGAGACAATGAGTTAAGAGAAAATGACAAGGAACAGCTC
Consensus   (1701) ACAGACTAGC AGAGACAATGA TTAAG GAAAATGACAA GAACAGCTC
                   1751                                                1800
NM_006218   (1751) AAAGCAATTCTACACGAGATCCTCTCTGAAATCACTGCACCAGAGAA
NM_008839   (1594) CGAGGCACTTTGCACCCGGACCCACTACCTGAAATCACTGACACAAGAGAA
Consensus   (1751)   AGCA TTT AC CG GA CC CT TCTGAAATCACTG CA GAGAA
                   1801                                                1850
NM_006218   (1801) AGATTTTCTATGGAGTCACAGACACTATTGTGTAACTATCCGCGAAATC
NM_008839   (1644) AGACTTCCTATGCAGCCACAGATACTACTGGTAACTATTGTGTAAATCT
Consensus   (1801) AGA TT CTATGGAG CACAGACACTA TG GTAACTAT CC GAAAT C
                   1851                                                1900
NM_006218   (1851) TACCCAAATTGCTTCTGTCTGTCAATGGAATTCTACAGAGAAGTGCC
NM_008839   (1694) TACCCAAATTGCTTCTGTCTGTCAAGTGGAATTCAGAGAACAACTGCC
Consensus   (1851) TACCCAAATTGCTTCTGTCTGT AA TGGAATTC AGAGA GAAGT GCC
                   1901                                                1950
NM_006218   (1901) CAGATGTATTGCTTGCTAAAGATTGGCCTCCAATCAAACCTGTAACAGGC
NM_008839   (1744) CAGATGTACTGCTTAGTAAAAGATGGCCTCCAATCAAACCACAGCAAGC
Consensus   (1901) CAGATGTA TGCTT GTAAAAGATTGGCCTCCAATCAAACC GA CA GC
                   1951                                                2000
NM_006218   (1951) TATGGAACTTCTGGACTGTAATTACCCAGATCCTATGGTTCCAGGTTTTG
NM_008839   (1794) CATGGAACTCCTGGACTTAACTATCCAGATCCTATGGTTCGGAGTTTTG
Consensus   (1951) ATGGAACT CTGGACTGTAA TA CCAGATCCTATGGTTCG  GTTTTG
                   2001                                                2050
NM_006218   (2001) CTGTTCGCTGCTTGGAAAAATATTTAACAGATGACAAACTTTCTCAGTT
NM_008839   (1844) CTGTTCGCTGCAGAAAAATATTTAACAGATGCCAAACTTTCTCAGTAC
Consensus   (2001) CTGTTCGGTGCTT GAAAAATATTTAACAGATGACAAACTTTCTCAGTA
                   2051                                                2100
NM_006218   (2051) TAAATTCAGCTAGTAGAGGTCCTAAAATATGAACACATTTGGATAACTT
NM_008839   (1894) CCCATTCAGTTCTACAGGTCTTAAAATATGAACATATTTGGATAAGCT
Consensus   (2051) T ATTCA CT GTACAGGTC TAAAATATGAACA TATTTGGATAAC T
```

FIGURE 3 (cont'd)

```
                  2101                                            2150
NM_006218  (2101) GCTTGTGAGATTTCTACTGAAGAAAGCATTGACTAATCAAAGGATTGGGC
NM_008839  (1944) GCTTGTGAGATTTTTACTCAAGAAAGCATTGACAAATAAAGGATTGGCC
Consensus  (2101) GCTTGTGAGATTTTTACT AAGAAAGCATTGAC AATCAAAGGATTGG C
                  2151                                            2200
NM_006218  (2151) ACTTTTCTTTTGGCATTTAAAAATCTGAGATGCACAATAAACAGTTAGC
NM_008839  (1994) ATTTTTTCTTTTGGCATTTAAAATCTGAGATGCACAATAAGACTGTCAGT
Consensus  (2151) A TTTTTCTTTTGGCATTTAAAATCTGAGATGCACAATAA AC GT AG
                  2201                                            2250
NM_006218  (2201) CAGAGGTTTGGCCTGCTTTTGGAGTCCTATTGTCGTGCATGTGGGATGTA
NM_008839  (2044) CAGAGGTTTGGCCTGCTATTGGAGTCCTACTGCCGTGCCTGTGGGATGTA
Consensus  (2201) CAGAGGTTTGGCCTGCT TTGGAGTCCTA TG CGTGC TGTGGGATGTA
                  2251                                            2300
NM_006218  (2251) TTTGAAGCACCTGAATAGGCAAGTCGAGGGAATGGAAAAGCTCATTAACT
NM_008839  (2094) TCTCAAGCACCTGAACAGACAAGTAGAGGGCATGGAGAAGCTCATCAACC
Consensus  (2251) T TGAAGCACCTGAA AG CAAGT GAGGG ATGGA AAGCTCAT AAC
                  2301                                            2350
NM_006218  (2301) TAACTGACATTCTCAAACAGGAGAAGAAGGATGAAACACAAAAGGTACAG
NM_008839  (2144) TAACCGACATCCTTAAGCAGGAGAAGAAGGATGACACACAAAAGGTACAG
Consensus  (2301) TAAC GACAT CT AA CAGGAGAAGAAGGATGA ACACAAAAGGTACAG
                  2351                                            2400
NM_006218  (2351) ATGAAGTTTTTACTTGAGCAAATGAGGGACCAGATTCATGGATGCTTCT
NM_008839  (2194) ATGAAGTTTTTCTTGAACAGATGAGAGACCAGCTTCATGGATGCTTT
Consensus  (2351) ATGAAGTTTTT GTTGA CA ATGAG C  CCAGA TTCATGGATGCT T
                  2401                                            2450
NM_006218  (2401) ACAGGGCTTTCTGTCTCCTCTAAACCTGCTCATCAACTAGGAAAGCTCA
NM_008839  (2244) GCAGGGCTTTTCTGTGCCCCTGTGAATCCTGCTCACCAACTAGGAAAGCTCA
Consensus  (2401)  CAGGG TTTCTGTC CCTCT AA CCTGCTCA CAACTAGGAAAGCTCA
                  2451                                            2500
NM_006218  (2451) GGCTTGAAGAGTGTCGAATTATGTCCTCTGCAAAAAGCCCACTCTGGTTG
NM_008839  (2294) GGCTTGAAGAGTGTCGAATTATGTCCTCTGCAAAAAGCCCACTGTGGTTG
Consensus  (2451) GGCTTGAAGAGTGTCGAATTATGTCCTCTGCAAAAAGCCCACTGTGGTTG
                  2501                                            2550
NM_006218  (2501) AATTGGGAGAACCCAGACATCATGTCAGAGTTACTGTTTCAGAACAATGA
NM_008839  (2344) AATTGGGAGAACCCAGACATCATGTCAGAGCTACTGTTTCAGAACAATGA
Consensus  (2501) AATTGGGAGAACCCAGACATCATGTCAGAG TACTGTTTCAGAACAATGA
                  2551                                            2600
NM_006218  (2551) GATCATCTCTAAAAATGGGGATGATTACGGCAAGATATGCAACACTTC
NM_008839  (2394) GATCATCTCTAAAAATGGCGACTACTTACGGCAAGATATGTAACCCTTC
Consensus  (2551) GATCATCTCTAAAAATGG GA GA TTACGGCAAGATATG TAAC CTTC
                  2601                                            2650
NM_006218  (2601) AAATTATTCGTATTATGGAAAATATCTGGCAAAATCAAGGTCTTGATCTT
NM_008839  (2444) AGATCATCGGAATCATGGAGAACACCTGGCAAAACGAAGGCCTTGACCTT
Consensus  (2601) A AT AT CG AT ATGGA AA ATCTGGCAAAA CAAGG CTTGA CTT
                  2651                                            2700
NM_006218  (2651) CGAATGTTACCTTATGGTGTCTCATGGCAATCGTGACTGTGTGGGACTTAT
NM_008839  (2494) CGCATGCTACCTTATGGCTGTCTATCCATTGGGACTGTGTGGGTCTCAT
Consensus  (2651) CG ATG TACCTTATGG TGTCT  C AT GG GACTGTGTGGG CT AT
                  2701                                            2750
NM_006218  (2701) TCAGGTGGTGCGAAATCCTCACACTATTATGCAAATTCAGTGCAAAGGCA
NM_008839  (2544) CGGAGGTGGTGAGAAACTCTGACAGCATCATGCAAATCGAGTGCAAAGGAG
Consensus  (2701) CAGGTGGTG GAAA TCTCACAC AT ATGCAAAT CAGTGCAAAGG G
                  2751                                            2800
NM_006218  (2751) GCTTGAAAGGCTGCACTGGACAGTTGAACAGCCACACGACTAGATCACTGGCTC
NM_008839  (2594) GCCTGAAGGGCGCCCTGCACTTGAACAGCCACACACTGCACCAATGGCTC
Consensus  (2751) GC TGAA GG GC CTGCACTTGAACAGCCACACACT CATCA TGGCTC
                  2801                                            2850
NM_006218  (2801) AAAGACAAGAACAAAGAAGGAGAATATATGATGCAGCCATTGACCTCTTAC
NM_008839  (2644) AAGCACAAGAACAAGGGGCAGATATATGATGCAGCCATTGACCTGTCAC
Consensus  (2801) AA GACAAGAACAA GG GA ATATATGATGCAGCCATTGACCTCTT AC
                  2851                                            2900
NM_006218  (2851) ACGTTCATGTGCTGGACTGTCTCAGCTACCTTCATTTGGGAATTCGAG
NM_008839  (2694) TCGGTCCTGCACTGGGTACTGCTGGAACCTTTATCTTGGGAATTCGAG
Consensus  (2851) CG TC TG GCTGG TACTG GT GC ACCTT AT TTGGGAATTCGAG
                  2901                                            2950
NM_006218  (2901) ATCGTCACAATAGTAACATCATGGTGAAAGACGATGGATAACGCTTCAT
NM_008839  (2744) ACCGGCACAACAGCAACATCATGGTGAAAGATGACGACACGTGTTTCAT
Consensus  (2901) A CG CACAA AG AACATCATGGTGAAAGA GA GGACA CTGTTTCAT
                  2951                                            3000
NM_006218  (2951) ATAGATTTTGGACACTTTTTGGATCACAAGAAGAAAAATTTGGCTATAA
NM_008839  (2794) ATAGATTTTGGCCACTTTTTGGATCACAAGAAGAAAAATTTGGCTATAA
Consensus  (2951) ATAGATTTTGG CACTTTTTGGATCACAAGAAGAAAAATTTGG TATAA
                  3001                                            3050
NM_006218  (3001) ACGAGAACGTGTGCCATTTGTTTTGACACAGGACTTCTAATAGTGATTA
NM_008839  (2844) GCGCGAACGTGTGCCATTTGTCTTGACACAGGATTCTTGATTGTGATTA
Consensus  (3001) CG GAACGTGTGCCATTTGT TTGACACAGGATTCTT AT GTGATTA
                  3051                                            3100
NM_006218  (3051) GTAAAGGAGCCCAAGAATGCAGAAAGACAAGAGAATTTGAGAGGCTTCAG
NM_008839  (2894) GTAAGGGAGCACAAGAGTACACCAAGACCAGAGAGTTTGAGAGGTTTCAG
Consensus  (3051) GTAA GGAGC CAAGA T CAC AAGAC AGAGA TTTGAGAGGTTTCAG
                  3101                                            3150
NM_006218  (3101) GACATGTGTTAGAAGGCTTATCTAGCTATTCGCAGCATGCCAATCTCTT
NM_008839  (2944) GACATGTGTTACAAGGCTTACCTAGCAATTCGGCAGCATGCCAATCTCTT
Consensus  (3101) GACATGTGTTACAAGGCTTA CTAGC ATTCG CAGCATGCCAATCTCTT
                  3151                                            3200
```

FIGURE 3 (cont'd)

```
NM_006218  (3151) CATAAATCTTTTCTCAATGATGCTTGGCTCTGGAATGCCAGAACTACAAT
NM_008839  (2994) CATCAACCTTTTTTCAATGATGCTTGGCTCTGGAATGCCAGAACTACAAT
Consensus  (3151) CAT AA CTTTT TCAATGATGCTTGGCTCTGGAATGCCAGAACTACAAT
                  3201                                              3250
NM_006218  (3201) CTTTTGATGACATTGCATACATTCGAAAGACCCTAGCCTTAGATAAAACT
NM_008839  (3044) CTTTTGATGACATTGCATATATCCGAAAGACTCTAGCCTTGGACAAAACT
Consensus  (3201) CTTTTGATGACATTGCATA AT CGAAAGAC CTAGCCTT GA AAAACT
                  3251                                              3300
NM_006218  (3251) GAGCAAGAGGCTTTGGAGTATTTCATGAAACAAATGAATGATGCACATCA
NM_008839  (3094) GAGCAAGAAGCTTTGGAATATTTCACAAAGCAAATGAATGATGCACATCA
Consensus  (3251) GAGCAAGA GCTTTGGA TATTTCA  AA CAAATGAATGATGCACATCA
                  3301                                              3350
NM_006218  (3301) TGGTGGCTGGACAACAAAAATGGATTGGATCTTCCACACAATTAAACAGC
NM_008839  (3144) TGGTGGATGGACGACAAAAATGGATTGGATCTTCCACACCATCAAGCAGC
Consensus  (3301) TGGTGG TGGAC ACAAAAATGGATTGGATCTTCCACAC AT AA CAGC
                  3351                                              3400
NM_006218  (3351) ATGCATTGAACTGAAAAGATAACTGAGAAAATGAAAGCTCACTCTGGATT
NM_008839  (3194) ATGCTTTGAACTGA-------------------------------------
Consensus  (3351) ATGC TTGAACTGA
                  3401                                              3450
NM_006218  (3401) CCACACTGCACTGTTAATAACTCTCAGCAGGCAAAGACCGATTGCATAGG
NM_008839  (3208) --------------------------------------------------
Consensus  (3401)
                  3451                                              3500
NM_006218  (3451) AATTGCACAATCCATGAACAGCATTAGAATTTACAGCAAGAACAGAAATA
NM_008839  (3208) --------------------------------------------------
Consensus  (3451)
                  3501                                              3550
NM_006218  (3501) AAATACTATATAATTTAAATAATGTAAACGCAAACAGGGTTTGATAGCAC
NM_008839  (3208) --------------------------------------------------
Consensus  (3501)
                  3551                                              3600
NM_006218  (3551) TTAAACTAGTTCATTTCAAAATTAAGCTTTAGAATAATGCGCAATTTCAT
NM_008839  (3208) --------------------------------------------------
Consensus  (3551)
                  3601                                              3650
NM_006218  (3601) GTTATGCCTTAAGTCCAAAAAGGTAAACTTTGAAGATTGTTTGTATCTTT
NM_008839  (3208) --------------------------------------------------
Consensus  (3601)
                  3651                                              3700
NM_006218  (3651) TTTTAAAAACAAAACAAAACAAAAATCCCCAAAATATATAGAAATGATG
NM_008839  (3208) --------------------------------------------------
Consensus  (3651)
                  3701            3724
NM_006218  (3701) GAGAAGGAAAAAAAAAAAAAAAAA
NM_008839  (3208) ------------------------
```

FIGURE 4

```
   1    TCTCC CTCGG CGCCG CCGCC GCCGC CCGCG GGGCT GGGAC CCGAT GCGGT
  51    TAGAG CCGCG GAGCC TGGAA GAGCC CCGAG CGTTT CTGCT TTGGG ACAAC
 101    CATAC ATCTA ATTCC TTAAA GTAGT TTTAT ATGTA AAACT TGCAA AGAAT
 151    CAGAA CAATG CCTCC ACGAC CATCA TCAGG TGAAC TGTGG GGCAT CCACT
 201    TGATG CCCCC AAGAA TCCTA GTAGA ATGTT TACTA CCAAA TGGAA TGATA
 251    GTGAC TTTAG AATGC CTCCG TGAGG CTACA TTAAT AACCA TAAAG CATGA
            ~~~~~~~~~~~~~~~~~~~~
            SEQ ID NO: 2
 301    ACTAT TTAAA GAAGC AAGAA AATAC CCCCT CCATC AACTT CTTCA AGATG
 351    AATCT TCTTA CATTT TCGTA AGTGT TACTC AAGAA CCAGA AGGGG AAGAA
                                                   ~~~~~~~~~~~~~~~~~~~~
                                                   SEQ ID NO: 3
 401    TTTTT TGATG AAACA AGACG ACTTT GTGAC CTTCG GCTTT TTCAA CCCTT
 451    TTTAA AAGTA ATTGA ACCAG TAGGC AACCG TGAAG AAAAG ATCCT CAATC
 501    GAGAA ATTGG TTTTG CTATC GGCAT GCCAG TGTGT GAATT TGATA TGGTT
 551    AAAGA TCCAG AAGTA CAGGA CTTCC GAAGA AATAT TCTGA ACGTT TGTAA
 601    AGAAG CTGTG GATCT TAGGG ACCTC AATTC ACCTC ATAGT AGAGC AATGT
                                                         ~~~~~~~~~~
                                                         SEQ ID NO: 4
 651    ATGTC TATCC TCCAA ATGTA GAATC TTCAC CAGAA TTGCC AAAGC ACATA
            ~~~~~~~~
 701    TATAA TAAAT TAGAT AAAGG GCAAA TAATA GTGGT GATCT GGGTA ATAGT
 751    TTCTC CAAAT AATGA CAAGC AGAAG TATAC TCTGA AAATC AACCA TGACT
 801    GTGTA CCAGA ACAAG TAATT GCTGA AGCAA TCAGG AAAAA ACTC GAAGT
 851    ATGTT GCTAT CCTCT GAACA ACTAA AACTC TGTGT TTTAG AATAT CAGGG
                                                         ~~~~~~~~~~
                                                         SEQ ID NO: 5
 901    CAAGT ATATT TTAAA AGTGT GTGGA TGTGA TGAAT ACTTC CTAGA AAAAT
            ~~~~~~~~
 951    ATCCT CTGAG TCAGT ATAAG TATAT AAGAA GCTGT ATAAT GCTTG GGAGG
1001    ATGCC CAATT TGATG TTGAT GGCTA AGAAA AGCCT TTATT CTCAA CTGCC
1051    AATGG ACTGT TTTAC AATGC CATCT TATTC CAGAC GCATT CCAC AGCTA
1101    CACCA TATAT GAATG GAGAA ACATC TACAA AATCC CTTTG GGTTA TAAAT
1151    AGTGC ACTCA GAATA AAAAT TCTTT GTGCA ACCTA CGTGA ATGTA AATAT
1201    TCGAG ACATT GATAA GATCT ATGTT CGAAC AGGTA TCTAC CATGG AGGAG
                                                                  ~~~~

1251    AACCC TTATG TGACA ATGTG AACAC TCAAA GAGTA CCTTG TTCCA ATCCC
            ~~~~~~~~~~~~~~
            SEQ ID NO: 6
1301    AGGTG GAATG AATGG CTGAA TTATG ATATA TACAT TCCTG ATCTT CCTCG
            ~~~~~~~~~~~~~~~~~~~~
            SEQ ID NO: 7
1351    TGCTG CTCGA CTTTG CCTTT CCATT TGCTC TGTTA AAGGC CGAAA GGGTG
1401    CTAAA GAGGA ACACT GTCCA TTGGC ATGGG AAAT ATAAA CTTGT TTGAT
1451    TACAC AGACA CTCTA GTATC TGGAA AAATG GCTTT GAATC TTTGG CCAGT
1501    ACCTC ATGGA TTAGA AGATT TGCTG AACCC TATTG GTGTT ACTGG ATCAA
                                                   ~~~~~~~~~~~~~~~~~~~~
                                                   SEQ ID NO: 8
1551    ATCCA AATAA AGAAA CTCCA TGCTT AGAGT TGGAG TTTGA CTGGT TCAGC
                             ~~~~~~~~~~~~~~~~~~~~
                             SEQ ID NO: 9
1601    AGTGT GGTAA AGTTC CCAGA TATGT CAGTG ATTGA AGAGC ATGCC AATTG
1651    GTCTG TATCC CGAGA AGCAG GATTT AGCTA TTCCC ACGCA GGACT GAGTA
1701    ACAGA CTAGC TAGAG ACAAT GAATT AAGGG AAAAT GACAA AGAAC AGCTC
1751    AAAGC AATTT CTACA CGAGA TCCTC TCTCT GAAAT CACTG AGCAG GAGAA
                                                 ~~~~~~~~~~~~~~~~~~~~~~
                                                 SEQ ID NO: 17
                                                 ~~~~~~~~~~~~~~~~~~~
                                                 SEQ ID NO: 18
                                                 ~~~~~~~~~~~~~~~~~
                                                 SEQ ID NO: 23
                                                 ~~~~~~~~~~~~~~~~~
                                                 SEQ ID NO: 24
                                                                  ~~~~~~~~~~~~~~
                                                                  SEQ ID NO: 19
                                                                   ~~~~~~~~~~~~~~~~~~~~~~
                                                                   SEQ ID NO: 20
                                                                   ~~~~~~~~~~~~~~~~
                                                                   SEQ ID NO: 25
```

FIGURE 4 (cont'd)

```
                                                    ~~~~~~~~~~~~~~~~~~~
                                                    SEQ ID NO: 26
1801    AGATT TTCTA TGGAG TCACA GACAC TATTG TGTAA CTATC CCCGA AATTC
1851    TACCC AAATT GCTTC TGTCT GTTAA ATGGA ATTCT AGAGA TGAAG TAGCC
             ~~~~~~~~~~~~~~~~~~~
             SEQ ID NO: 10
1901    CAGAT GTATT GCTTG GTAAA AGATT GGCCT CCAAT CAAAC CTGAA CAGGC
1951    TATGG AACTT CTGGA CTGTA ATTAC CCAGA TCCTA TGGTT CGAGG TTTTG
2001    CTGTT CGGTG CTTGG AAAAA TATTT AACAG ATGAC AAACT TTCTC AGTAT
2051    TTAAT TCAGC TAGTA CAGGT CCTAA AATAT GAACA ATATT TGGAT AACTT
2101    GCTTG TGAGA TTTTT ACTGA AGAAA GCATT GACTA ATCAA AGGAT GGGGC
2151    ACTTT TTCTT TTGGC ATTTA AAATC TGAGA TGCAC AATAA AACAG TTAGC
                                      ~~~~~~~~~~~~~~~~~~~
                                      SEQ ID NO: 11
2201    CAGAG GTTTG GCCTG CTTTT GGAGT CCTAT TGTCG TGCAT GTGGG ATGTA
2251    TTTGA AGCAC CTGAA TAGGC AAGTC GAGGC AATGG AAAAG CTCAT TAACT
2301    TAACT GACAT TCTCA AACAG GAGAA GAAGG ATGAA ACACA AAAGG TACAG
2351    ATGAA GTTTT TAGTT GAGCA ATGA GGCGA CCAGA TTTCA TGGAT GCTCT
2401    ACAGG GCTTT CTGTC TCCTC TAAAC CCTGC TCATC AACTA GGAAA CCTCA
2451    GGCTT GAAGA GTGTC GAATT ATGTC CTCTG CAAAA AGGCC ACTGT GGTTG
             ~~~~~~~~~~~~~~~~~~~
             SEQ ID NO: 12
2501    AATTG GGAGA ACCCA CACAT CATGT CAGAG TTACT GTTTC AGAAC AATGA
             ~~~~~~~~~~~~~~~~~~~
             SEQ ID NO: 13
2551    GATCA TCTTT AAAAA TGGGG ATGAT TTACG GCAAG ATATG CTAAC ACTTC
2601    AAATT ATTCG TATTA TGGAA AATAT CTGGC AAAAT CAAGG TCTTG ATCTT
2651    CGAAT GTTAC CTTAT GGTTG TCTGT CAATC GGTGA CTGTG TGGGA CTTAT
2701    TGAGG TGGTG CGAAA TTCTC ACACT ATTAT GCAAA TTCAG TGCAA AGGCG
2751    GCTTG AAAGG TGCAC TGCAG TTCAA CAGCC ACACA CTACA TCAGT GGCTC
2801    AAAGA CAAGA ACAAA GGAGA AATAT ATGAT GCAGC CATTG ACCTG TTTAC
2851    ACGTT CATGT GCTGG ATACT GTGTA GCTAC CTTCA TTTTG GGAAT TGGAG
2901    ATCGT CACAA TAGTA ACATC ATGGT GAAAG ACGAT GGACA ACTGT TTCAT
2951    ATAGA TTTTG GACAC TTTTT GGATC ACAAG AAGAA AAAAT TTGGT TATAA
                                 ~~~~~~~~~~~~~~~~~~~
                                 SEQ ID NO: 14
3001    ACGAG AACGT GTGCC ATTTG TTTTG ACACA GGATT TCTTA ATAGT GATTA
                                 ~~~~~~~~~~~~~~~~~~~
                                 SEQ ID NO: 15
3051    GTAAA GGAGC CCAAG AATGC ACAAA GACAA GAGAA TTTGA GAGGT TTCAG
                                                    ~~~~~~~~~~~~~~~~
                                                    SEQ ID NO: 16
3101    GAGAT GTGTT ACAAG GCTTA TCTAG CTATT CGACA GCATG CCAAT CTCTT
        ~~~~
3151    CATAA ATCTT TTCTC AATGA TGCTT GGCTC TGGAA TGCCA GAACT ACAAT
3201    CTTTT GATGA CATTG CATAC ATTCG AAAGA CCCTA GCCTT AGATA AAACT
3251    GAGCA AGAGG CTTTG GAGTA TTTCA TGAAA CAAAT GAATG ATGCA CATCA
                                                    ~~~~~~~~~~~~~
                                                    SEQ ID NO: 21
                                                 ~~~~~~~~~~~~~~~~
                                                 SEQ ID NO: 22
                                                    ~~~~~~~~~~~
                                                    SEQ ID NO: 27
                                              ~~~~~~~~~~~~~~~~~~
                                              SEQ ID NO: 28
3301    TGGTG GCTGG ACAAC AAAAA TGGAT TGGAT CTTCC ACACA ATTAA ACAGC
        ~~~~~~~~

~~~~

~~~~~~~~

~~~~

3351    ATGCA TTGAA CTGA A AAGAT AACTG AGAAA ATGAA AGCTC ACTCT GGATT
3401    CCACA CTGCA CTCTT AATAA CTCTC AGCAG GCAAA GACCG ATTGC ATAGG
3451    AATTG CACAA TCCAT GAACA GCATT AGAAT TTACA GCAAG AACAG AAATA
3501    AAATA CTATA TAATT TAAAT AATGT AAACG CAAAC AGGGT TTGAT AGCAC
3551    TTAAA CTAGT TCATT TCAAA ATTAA GCTTT AGAAT AATGC GCAAT TTCAT
3601    GTTAT GCCTT AAGTC CAAAA AGGTA AACTT TGAAG ATTGT TTGTA TCTTT
3651    TTTTA AAAAA CAAAA CAAAA CAAAA ATCCC CAAAA TATAT AGAAA TGATG
3701    GAGAA GGAAA AAAAA AAAAA AAAA
```

FIGURE 5

SEQ ID NO: 1 Homo sapiens phosphoinositide-3-kinase, catalytic, alpha polypeptide
(PIK3CA)mRNA, Accession number NM_006218, 3724 bp

```
   1 tctccctcgg cgccgccgcc gccgcccgcg gggctgggac ccgatgcggt tagagccgcg
  61 gagcctggaa gagccccgag cgtttctgct ttgggacaac catacatcta attccttaaa
 121 gtagtttat atgtaaaact tgcaaagaat cagaacaatg cctccacgac catcatcagg
 181 tgaactgtgg ggcatccact tgatgccccc aagaatccta gtagaatgtt tactaccaaa
 241 tggaatgata gtgactttag aatgcctccg tgaggctaca ttaataacca taaagcatga
 301 actatttaaa gaagcaagaa ataccccct ccatcaactt cttcaagatg aatcttctta
 361 cattttcgta agtgttactc aagaagcaga aagggaagaa tttttgatg aaacaagacg
 421 actttgtgac cttcggcttt ttcaacccctt tttaaaagta attgaaccag taggcaaccg
 481 tgaagaaaag atcctcaatc gagaaattgg ttttgctatc ggcatgccag tgtgtgaatt
 541 tgatatggtt aaagatccag aagtacagga cttccgaaga aatattctga acgtttgtaa
 601 agaagctgtg gatcttaggg acctcaattc acctcatagt agagcaatgt atgtctatcc
 661 tccaaatgta gaatcttcac cagaattgcc aaagcacata tataataaat tagataaagg
 721 gcaaataata gtggtgatct gggtaatagt ttctccaaat aatgacaagc agaagtatac
 781 tctgaaaatc aaccatgact gtgtaccaga acaagtaatt gctgaagcaa tcaggaaaaa
 841 aactcgaagt atgttgctat cctctgaaca actaaaactc tgtgtttag aatatcaggg
 901 caagtatatt ttaaaagtgt gtggatgtga tgaatacttc ctagaaaaat atcctctgag
 961 tcagtataag tatataagaa gctgtataat gcttgggagg atgcccaatt tgatgttgat
1021 ggctaaagaa agcctttatt ctcaactgcc aatggactgt tttacaatgc catcttattc
1081 cagacgcatt tccacagcta caccatatat gaatggagaa acatctacaa aatcccttttg
1141 ggttataaat agtgcactca gaataaaaat tctttgtgca acctacgtga atgtaaatat
1201 tcgagacatt gataagatct atgttcgaac aggtatctac catggaggag aacccttatg
1261 tgacaatgtg aacactcaaa gagtaccttg ttccaatccc agtgggaatg aatggctgaa
1321 ttatgatata tacattcctg atcttcctcg tgctgctcga cttttgccttt ccatttgctc
1381 tgttaaaggc cgaaagggtg ctaaagagga acactgtcca ttggcatggg aaatataaa
1441 cttgtttgat tacacagaca ctctagtatc tggaaaaatg ctttgaatc tttggccagt
1501 acctcatgga ttagaagatt tgctgaaccc tattggtgtt actggatcaa atccaaataa
1561 agaaactcca tgcttagagt tggagtttga ctggttcagc agtggtgtaa agttcccaga
1621 tatgtcagtg attgaagagc atgccaattg gtctgtatcc cgagaagcag gatttagcta
1681 ttcccacgca ggactgagta acagactagc tagagacaat gaattaaggg aaaatgacaa
1741 agaacagctc aaagcaattt ctacacgaga tcctctctct gaaatcactg agcaggagaa
1801 agattttcta tggagtcaca gacactattg tgtaactatc cccgaaattc tacccaaatt
1861 gcttctgtct gttaaatgga attctagaga tgaagtagcc cagatgtatt gcttggtaaa
1921 agattggcct ccaatcaaac ctgaacaggc tatggaactt ctggactgta attacccaga
1981 tcctatggtt cgaggttttg ctgttcggtg cttggaaaaa tatttaacag atgacaaact
2041 ttctcagtat ttaattcagc tagtacaggt cctaaaatat gaacaatatt tggataactt
2101 gcttgtgaga ttttactga agaaagcatt gactaatcaa aggattgggc actttttctt
2161 ttggcattta aaatctgaga tgcacaataa aacagttagc cagaggtttg gcctgctttt
2221 ggagtcctat tgtcgtgcat gtgggatgta tttgaagcac ctgaataggc aagtcgaggc
2281 aatggaaaag ctcattaact taactgacat tctcaaacag gagaagaagg atgaaacaca
2341 aaaggtacag atgaagtttt tagttgagca aatgaggcga ccagatttca tggatgctct
2401 acagggcttt ctgtctcctc taaaccctgc tcatcaacta ggaaacctca ggcttgaaga
2461 gtgtcgaatt atgtcctctg caaaaggcc actgtggttg aattggaga acccagacat
2521 catgtcagag ttactgtttc agaacaatga gatcatcttt aaaaatgggg atgatttacg
2581 gcaagatatg ctaacacttc aaattattcg tattatggaa aatctctggc aaaatcaagg
2641 tcttgatctt cgaatgttac cttatggttg tctgtcaatc ggtgactgtg tgggacttat
2701 tgaggtggtg cgaaattctc acactattat gcaaattcag tgcaaggcg gcttgaaagg
2761 tgcactgcag ttcaacagcc acacactaca tcagtggctc aaagacaaga acaaggaga
2821 aatatatgat gcagccattg acctgtttca acgttcatgt gctggatact gtgtagctac
2881 cttcatttttg ggaattggag atcgtcacaa tagtaacatc atggtgaaag acgatgacga
2941 actgtttcat atagattttg gacacttttt ggatcacaag aagaaaaaat ttggttataa
3001 acgagaacgt gtgccatttg ttttgacaca ggatttctta atagtgatta gtaaggagc
3061 ccaagaatgc acaaagacaa gagaattga gaggtttcag gagatgtgtt acaaggctta
3121 tctagctatt cgacagcatg ccaatctctt cataaatctt ttctcaatga tgcttggctc
3181 tggaatgcca gaactacaat cttttgatga cattgcatac attcgaaaga ccctagcctt
3241 agataaaact gagcaagagg ctttggagta tttcatgaaa caatgaatg atgcacatca
3301 tggtggctgg acaacaaaaa tggattggat cttccacaca attaaacagc atgcattgaa
3361 ctgaaaagat aactgagaaa atgaaagctc actctggatt ccacactgca ctgttaataa
3421 ctctcagcag gcaaagaccg attgcatagg aattgcacaa tccatgaaca gcattagaat
3481 ttacagcaag aacagaaata aaatactata taatttaaat aatgtaaacg caaacagggt
3541 ttgatagcac ttaaactagt tcatttcaaa attaagcttt agaataatgc gcaatttcat
3601 gttatgcctt aagtccaaaa aggtaaactt tgaagattgt ttgtatcttt ttttaaaaa
3661 caaaacaaaa caaaaatccc caaaatatat agaaatgatg gagaaggaaa aaaaaaaaa
3721 aaaa
```

FIGURE 6

```
SEQ ID NO: 105
LOCUS       NP_006209                1068 aa
DEFINITION  phosphoinositide-3-kinase, catalytic, alpha polypeptide [Homo
            sapiens].
ACCESSION   NP_006209
VERSION     NP_006209.2  GI:54792082
SOURCE      Homo sapiens (human)

ORIGIN
        1 mpprpssgel wgihlmppri lvecllpngm ivtleclrea tlitikhelf kearkyplhq
       61 llqdessyif vsvtqeaere effdetrrlc dlrlfqpflk viepvgnree kilnreigfa
      121 igmpvcefdm vkdpevqdfr rnilnvckea vdlrdlnsph sramyvyppn vesspelpkh
      181 iynkldkgqi ivviwvivsp nndkqkytlk inhdcvpeqv iaeairkktr smllsseqlk
      241 lcvleyqgky ilkvcgcdey flekyplsqy kyirscimlg rmpnlmlmak eslysqlpmd
      301 cftmpsysrr istatpymng etstkslwvi nsalrikilc atyvnvnird idkiyvrtgi
      361 yhggeplcdn vntqrvpcsn prwnewlnyd iyipdlpraa rlclsicsvk grkgakeehc
      421 plawgninlf dytdtlvsgk malnlwpvph gledllnpig vtgsnpnket pclelcfdwf
      481 ssvvkfpdms vieehanwsv sreagfsysh aglsnrlard nelrendkeq lkaistrdpl
      541 seiteqekdf lwshrhycvt ipeilpklll svkwnsrdev aqmyclvkdw ppikpeqame
      601 lldcnypdpm vrgfavrcle kyltddklsq yliqlvqvlk yeqyldnllv rfllkkaltn
      661 qrighfffwh lksemhnktv sqrfgllles ycracgmylk hlnrqveame klinltdilk
      721 qekkdetqkv qmkflveqmr rpdfmdalqg flsplnpahq lgnlrleecr imssakrplw
      781 lnwenpdims ellfqnneii fkngddlrqd mltlqiirim eniwqnqgld lrmlpygcls
      841 igdcvgliev vrnshtimqi qckgglkgal qfnshtlhqw lkdknkgeiy daaidlftrs
      901 cagycvatfi lgigdrhnsn imvkddgqlf hidfghfldh kkkkfgykre rvpfvltqdf
      961 liviskgaqe ctktrefrf qemcykayla irqhanlfin lfsmmlgsgm pelqsfddia
     1021 yirktlaldk teqealeyfm kqmndahhgg wttkmdwifh tikqhaln
```

FIGURE 7

```
SEQ ID NO: 106
LOCUS       NM_008839               3207 bp    mRNA
DEFINITION  Mus musculus phosphatidylinositol 3-kinase, catalytic, alpha
            polypeptide (Pik3ca), mRNA.
ACCESSION   NM_008839
VERSION     NM_008839.1  GI:6679316
SOURCE      Mus musculus (house mouse)

ORIGIN
        1 atgcctccac gaccatcttc gggtgaactg tggggcatcc acttgatgcc cccacgaatc
       61 ctagtggaat gtttactccc caatggaatg atagtgactt tagaatgcct ccgtgaggcc
      121 acactcgtca ccatcaaaca tgaactgttc agagaggcca ggaaataccc tctccatcag
      181 cttctgcaag acgaaacttc ttacattttc gtaagtgtca cccaagaagc agaaagggaa
      241 gaattttttg atgaaacaag acgactttgt gaccttcggc ttttcaacc cttttaaaa
      301 gttattgaac cagtaggcaa ccgtgaagaa aagatcctca atcgagaaat tggttttgtt
      361 attggcatgc cagtgtgtga atttgatatg gttaaagatc cagaagtcca agactttcga
      421 aggaacattc tgaatgtttg caaagaagct gtggacctgc gggatctcaa ctcgcctcat
      481 agcagagcaa tgtatgtcta ccctccaaat gtcgagtctt ccccagaact gccaaagcac
      541 atctacaaca agttagataa aggacaaatc atagtggtga tttgggtaat agtctctcca
      601 aacaacgaca agcagaagta cactctgaag atcaatcatg actgtgtgcc agagcaagtc
      661 attgctgaag ccatcaggaa aaagactcgg agcatgttgt tgtcctctga gcagctgaaa
      721 ctctgtgtct tagaatatca gggcaagtat attctgaaag tgtgtggctg tgacgaatac
      781 ttcctggaaa agtaccctct gagtcagtac aagtacataa gaagctgtat aatgctgggg
      841 aggatgccca acttgatgct gatggccaaa gaaagcctat actctcagct gccgattgat
      901 agcttcacca tgcgtcata ctccaggcgc atctccacag ccacaccta catgaatgga
      961 gagacatcta cgaaatccct ctgggtcata aatagtgcgc tcagaataaa aattctttgt
     1021 gcaacctatg taaatgtaaa tattcgagac attgataaga tctatgttcg aacaggtatc
     1081 taccatggag gagaaccctt atgtgacaat gtgaacactc aaagagtacc ttgttccaat
     1141 cctaggtgga atgaatggct gaattatgat atatacattc ctgatcttcc tcgtctggcg
     1201 cgcctttgcc tttcaatctg ctctgttaaa ggccgaaagg gtgctaagga ggagcactgt
     1261 ccgttggcct ggggaaacat aaacttgttt gattatacag acaccctagt gtccgggaaa
     1321 atggctttga atctctggcc tgtaccgcat gggttagaag atctgctgaa ccctattgt
     1381 gttactgggt caaatccaaa taaagaaact ccatgcttag agttggagtt tgattggttc
     1441 agcagtgtgg tgaagtttcc agacatgtct gtgatcgaag aacatgccaa ttggtccgtg
     1501 tcccgagaag ctggattcag ttactcccat acaggactga gtaacagact agccagagac
     1561 aatgagttaa gagaaaatga caaggaacag ctccgagcac tttgcacccg ggacccacta
     1621 tctgaaatca ctgaacaaga gaaagacttc ctatggagcc acagacacta ctgcgtaact
     1681 attcctgaaa tcctacccaa attgcttctg tctgtcaagt ggaattccag agacgaagtg
     1741 gcccagatgt actgcttagt aaaagattgg cctccaatca aaccagagca agccatgaa
     1801 ctcctggact gtaactatcc agatcctatg gttcggagtt ttgctgttcg gtgcttagaa
     1861 aaatatttaa cagatgacaa actttctcag tacctcattc aacttgtaca ggtcttaaaa
     1921 tatgaacagt atttggataa cctgcttgtg agattttac tcaagaaagc attgacaaat
     1981 caaaggattg gccattttt cttttggcat ttaaaatctg agatgcacaa taagactgtc
     2041 agtcagaggt ttggcctgct attggagtcc tactgccgtg cctgtgggat gtatctgaag
     2101 cacctgaaca gacaagtaga ggccatggag aagctcatca acctaacgga catccttaag
     2161 caggagagaa aggtagagac acaaaaggta cagatgaagt ttttggttga acagatgaga
     2221 cagccagact tcatggatgc tttgcagggt tttctgtccc ctctgaatcc tgctcaccaa
     2281 ctaggaaacc tcaggcttga agagtgtcga attatgtcct ctgcaaaaag gccactgtgg
     2341 ttgaattggg agaacccaga catcatgtca gagctactgt tcagaacaa tgagatcatc
     2401 tttaaaaatg gcgacgactt acggcaagat atgttaaccc ttcagatcat ccgaatcatg
     2461 gagaacatct ggcaaaacca aggccttgac cttcgcatgc taccttatgg ctgtctatcc
     2521 attggggact gtgtgggtct catcgaggtg gtgagaaact ctcacaccat catgcaaatc
     2581 cagtgcaaag gaggcctgaa gggggcgctg cagttcaaca gccacacact gcatcaatgg
     2641 ctcaaggaca agaacaaggg cgagatatat gatgcagcc ttgacctgtt cactcggtcc
     2701 tgcgctgggt actgcgtggc aacctttatc ttgggaattg agaccggca caacagcaac
     2761 atcatggtga agatgacgg acagctgttt catatagatt ttggcactt tttggatcac
     2821 aagaagaaaa aatttggcta taagcgggaa cgtgtgccat tgtgttgac acaggatttc
     2881 ttgattgtga ttagtaaggg agcacaagag tacaccaaga ccagagagtt tgagaggttt
     2941 caggagatgt gttacaaggc ttacctagca attcggcagc atgccaatct cttcatcaac
     3001 cttttttcaa tgatgcttgg ctctggaatg ccagaactac aatcttttga tgacattgca
     3061 tatatccgaa agactctagc cttggacaaa actgagcaag aagctttga atatttcaca
     3121 aagcaaatga tgatgcaca tcatggtgga tggacgacaa aaatggattg gatcttccac
     3181 accatcaagc agcatgcttt gaactga
```

FIGURE 8

```
SEQ ID NO: 107
LOCUS       NP_032865                1068 aa
DEFINITION  phosphatidylinositol 3-kinase, catalytic, alpha
polypeptide [Mus
            musculus].
ACCESSION   NP_032865
VERSION     NP_032865.1  GI:6679317
SOURCE      Mus musculus (house mouse)

ORIGIN
        1 mpprpssgel wgihlmppri lvecllpngm ivtleclrea tlvtikhelf rearkyplhq
       61 llqdetsyif vsvtqcaere effdetrrlc dlrlfqpflk viepvgnree kilnreigfv
      121 igmpvcefdm vkdpevqdfr rnilnvckea vdlrdlnsph sramyvyppn vesspelpkh
      181 iynkldkgqi ivviwvivsp nndkqkytlk inhdcvpeqv iaeairkktr smllsseqlk
      241 lcvleyqgky ilkvcgcdey flekyplsqy kyirscimlg rmpnlmlmak eslysqlpid
      301 sftmpsysrr lstatpymng etstkslwvi nsalrikilc atyvnvnird idkiyvrtgi
      361 yhggeplcdn vntqrvpcsn prwnewlnyd iyipdlprla rlclsicsvk grkgakeehc
      421 plawgninlf dytdtlvsgk malnlwpvph gledllnpig vtgsnpnket pclelefdwf
      481 ssvvkfpdms vieehanwsv sreagfsysh tglsnrlard nelrendkeq lralctrdpl
      541 seiteqekdf lwshrhycvt ipeilpklll svkwnsrdev aqmyclvkdw ppikpeqame
      601 lldcnypdpm vrsfavrcle kyltddklsq yliqlvqvlk yeqyldnllv rfllkkaltn
      661 qrighfffwh lksemhnktv sqrfqllles ycracgmylk hlnrqveame klinitdilk
      721 qekkdetqkv qmkflveqmr qpdfmdalqg flsplnpahq lgnlrleecr imssakrplw
      781 lnwenpdims ellfqnneii fkngddlrqd mltlqiirim eniwqnqgld lrmlpygcls
      841 igdcvgliev vrnshtimqi qckgglkgal qfnshtlhqw lkdknkgeiy daaidlftrs
      901 cagycvatfi lgigdrhnsn imvkddgqlf hidfghfldh kkkkfgykre rvpfvltqdf
      961 liviskgaqe ytktreferf qemcykayla irqhanlfin lfsmmlgsgm pelqsfddia
     1021 yirktlaldk teqealeyft kqmndahhgg wttkmdwifh tikqhaln
//
```

FIGURE 9

```
SEQ ID NO: 108
LOCUS       XM_001109162           4326 bp    mRNA
DEFINITION  PREDICTED: Macaca mulatta similar to phosphoinositide-3-kinase,
            catalytic, alpha polypeptide (LOC709959), mRNA.
ACCESSION   XM_001109162
VERSION     XM_001109162.1  GI:109043556
SOURCE      Macaca mulatta (rhesus monkey)

ORIGIN
        1 tctccctcgg cgccgccgcc gccgcccgcg gggctgggac ccgatgcggt tagagccgcg
       61 gagcctggaa gagcccgag cgtttctgct ttgggacaac catacgtcta attctttaaa
      121 gtagttttat atgtaaaacc tgcaaaaaat cagaacaatg cctccacgac catcatcagg
      181 tgaactgtgg ggcatccact tgatgccccc aagaatccta gtagaatgtt tactaccaaa
      241 tggaatgata gtgactttag aatgcctccg tgaggctaca ttaataacca taaagcatga
      301 actatttaaa gaagcaagaa aatacccct ccatcaactt cttcaagatg aatcttctta
      361 catttttcgta agtgttaccc aagaagcaga aagggaagaa ttttttgatg aaacaagacg
      421 actttgtgac cttcggcttt ttcaacccct tttaaaagta attgaaccag taggcaaccg
      481 tgaagaaaag atcctcaatc gagaaattgg ttttgctatt ggcatgccag tgtgtgaatt
      541 tgatatggtt aaagatccag aagtacagga cttccgaaga aatattctga atgtttgtaa
      601 agaagctgtg gatcttaggg atctcaattc acctcatagt agagcaatgt atgtctatcc
      661 tccaaatgta gaatcttcgc cagaattgcc aaagcacata tataataaat tagataaagg
      721 gcaaataata gtggtgattt gggtaatagt ttctccaaat aatgacaagc agaagtatac
      781 tctgaaaatc aaccatgact ctgtaccaga acaagtaatt gctgaagcaa tcaggaaaaa
      841 aactcgaagt atgttgctat cctctgaaca gctaaaactc tgtgttttag aatatcaggg
      901 caagtatatt ttaaaagtgt gtggatgtga tgaatacttc ctagaaaaat atcctctgag
      961 tcagtataag tatataagaa gctgtataat gcttgggagg atgcccaatt tgatgttgat
     1021 ggctaaagaa agcctttatt ctcaactgcc aatggactgt tttacaatgc catcttattc
     1081 cagacgcatt tccacagcta caccatatat gaatggagaa acatctacaa aatccctttg
     1141 ggttataaat agtgcactca gaataaaaat tctttgtgca acctacgtga atgtaaatat
     1201 tcgagacatt gataagatct atgttcgaac aggtatctac catggaggag aaccccttatg
     1261 tgacaatgtg aacactcaaa gagtaccttg ttccaatccc aggtggaatg aatggctgaa
     1321 ttatgatata tacattcctg accttcctcg tgctgctcga cttttgccttt ccatttgctc
     1381 tgttaaaggc cgaaaggggt ctaaagagga acactgtcca ttggcatggg gaaatataaa
     1441 cttgtttgat tacacagaca ctctagtatc tggaaaaatg gctttgaatc tttggccagt
     1501 acctcatgga ttagaagatt tgctgaaccc tattggtgtt actggatcaa atccaaataa
     1561 agaaactcca tgcttagagt tggagtttga ctggttcagc agtgtggtaa agttcccaga
     1621 tatgtcagtg attgaagagc atgccaattg gtctgtgtcc cgagaagcag gatttagcta
     1681 ttcccacgca ggactgagta acaggctagc tagagacaat gaattaaggg aaaatgacaa
     1741 agaacagctc aaagcaattt ctacacgaga tcctctctct gaaatcactg agcaggagaa
     1801 agatttctg tggagccaca gacactattg tgtaactatc cccgaaattc tacccaaatt
     1861 gcttctgtct gttaaatgga attctagaga tgaagtagcc cagatgtatt gcttggtaaa
     1921 agactggcct ccaatcaaac ctgaacaggc tatgaacctt ctggactgta attacccaga
     1981 tcctatggtt cgaggtttt ctgttcggtg cttggaaaaa tatttaacag atgacaaact
     2041 ttctcagtat ttaattcagc tagtacaggt cctaaaatat gaacaatatt tggataactt
     2101 gcttgtgaga ttttactga agaaagcatt gactaatcaa aggattgggc actttttctt
     2161 ttggcattta aaatctgaga tgcacaataa acagttagc cagaggtttg gcctgctttt
     2221 ggagtcctat tgtcgtgcat gtgggatgta tttgaagcac ctgaataggc aagtcgaggc
     2281 aatgaaaaag ctcattaact taactgacat tctcaaacag gagaaaaagg atgaaacaca
     2341 aaaggtacag atgaagtttt tagttgagca aatgaggcga ccagatttca tggatgctct
     2401 gcagggcttt ctatctcctc taaaccctgc tcatcaacta ggaaatctca ggcttgaaga
     2461 gtgtcgaatt atgtcctctg caaaaaggcc actgtggttg aattgggaga cccagacat
     2521 catgtcagag ttactgtttc agaacaatga gatcatcttt aaaatgggg atgatttacg
     2581 gcaagatatg ctaacacttc aaattattcg tattatggaa aatatctgg aaaatcaagg
     2641 tcttgatctt cgaatgttac cttatgttgtg tctgtcaatc ggtgactgtg tgggacttat
     2701 tgaggtggtg cgaaattctc acactattat gcaaattcag tgcaaggcg gcttgaaagg
     2761 tgcactgcag ttcaacagcc acactctaca tcagtggctc aaagacaaga caaaggaga
     2821 aatatatgat gcagccattg acctgtttac acgttcatgt gctggatatt gtgtcgctac
     2881 cttcattctg ggaattggag atcgtcacaa tagtaacatc atggtgaaag cgatggaca
     2941 actgtttcat atagattttg gacactttt ggatcacaag aagaaaaat ttggctataa
     3001 acgagaacgt gtgccatttg ttttgacaca ggatttctta atagtgatta gtaaaggagc
     3061 ccaagaatgc acaaagacaa gagaatttga gaggtttcag gagatgtgtt acaaggctta
     3121 tctagctatt cgacagcatg ccaatctctt cataaatctt ttctcaatga tgcttggctc
     3181 tggaatgcca gaactacaat cttttgatga cattgcatac attcgaaaga ccctagccct
```

FIGURE 9 (cont'd)

```
3241 agataaaact gagcaagagg ctttggaata tttcatgaaa caaatgaatg atgcacatca
3301 tggtggctgg acaacaaaaa tggattggat cttccacaca attaaacagc atgcattgaa
3361 ctgaaaagat aactgagaaa atgaaagctc actctctgga ttccacactg cactgttaat
3421 aactatcagc aggcaaagac cgattgcata ggaattgcac aatccatgaa cagcattaga
3481 atttacagca agaacagaaa taaaatacta tataatttaa tgtaaacgca aacagggttt
3541 gatagcactt aaactagttc atttcacaat taagctttag aataatgcgc aatttcatgt
3601 tatgccttaa gtccaaaaag gtaaactttg aagattgttt gtatcttttt ttaaaaaaca
3661 aaacaaaaca aaaatcccca aaatatatag aaatgatgga gaaggaaaaa tgatgttttt
3721 ttttgtcttg caaatgttct atgttttgaa atgtggacac aacaaaagct gttattgttt
3781 taggtgtaag taaactggag tttatgttaa attacattaa gattggaaaa gaatgaaaat
3841 ttcttatttt tccattgctg ttcaatttat agtttgagtg ggttttttgac tccttgttta
3901 atgaagaaaa atgcttgggg tggaagggac tcttgagatt tcaccagaga ctttttcttt
3961 ttaataaatc aaaccttttg atgatttgag gtcttatctg cagttttgga agcagtcaca
4021 aatgagacct gttataaggt ggtatttttt ttttttttct ggacagtatt taaaggattt
4081 tatttcccag ggaaattctg ggctcccaca gagtttaaaa aaaaaaaaaa aaaaaaatca
4141 tagaaaaaga atgaacagga atagttctta ttccaaaatt gtacagtatt cacccttaagt
4201 tgatttttttt ctccttttgc agttgaactg aatacatttt tcatgcatgt tttccaaaaa
4261 atagaagtat taatgttatt aaaaagatta tttttttttat taaaggctat ttatattata
4321 gaaact
//
```

FIGURE 10

```
SEQ ID NO: 109
LOCUS       XP_001109162                1068 aa
DEFINITION  PREDICTED: similar to phosphoinositide-3-kinase, catalytic,
alpha polypeptide [Macaca mulatta].
ACCESSION   XP_001109162
VERSION     XP_001109162.1  GI:109043557
SOURCE      Macaca mulatta (rhesus monkey)

ORIGIN
        1 mpprpssgel wgihlmppri lvecllpngm ivtleclrea tlitikhelf kearkyplhq
       61 llqdessyif vsvtqeaere effdetrrlc dlrlfqpflk viepvgnree kilnreigfa
      121 igmpvcefdm vkdpevqdfr rnilnvckea vdlrdlnsph sramyvyppn vesspelpkh
      181 iynkldkgqi ivviwvivsp nndkqkytlk inhdcvpeqv iaeairkktr smllsseqlk
      241 lcvleyqgky ilkvcgcdey flekyplsqy kyirscimlg rmpnlmlmak eslysqlpmd
      301 cftmpsysrr istatpymng etstkslwvi nsalrikilc atyvnvnird idkiyvrtgi
      361 yhggeplcdn vntqrvpcsn prwnewlnyd iyipdlpraa rlclsicsvk grkgakeehc
      421 plawgninlf dytdtlvsgk malnlwpvph gleddllnpig vtgsnpnket pclelefdwf
      481 ssvvkfpdcms vieehanwsv sreagfsysh aglsnrlard nelrendkeq lkaistrdpl
      541 seiteqekdf lwshrhycvt ipeilpklll svkwnsrdev aqmyclvkdw ppikpeqame
      601 lldcnypdpm vrgfavrcle kyltddklsq yliqlvqvlk yeqyldnllv rfllkkaltn
      661 qrighfffwh lksemhnktv sqrfgllles ycracgmylk hlnrqveame klinltdilk
      721 qekkdetqkv qmkflveqmr rpdfmdalqg flsplnpahq lgnlrleecr imssakrplw
      781 lnwenpdims ellfqnneii fkngddlrqd mltlqiirim eniwqnqgld lrmlpygcls
      841 igdcvgliev vrnshtimqi qckgglkgal qfnshtlhqw lkdknkgeiy daaidlftrs
      901 cagycvatfi lgigdrhnsn imvkddgqlf hidfghfldh kkkkfgykre rvpfvltqdf
      961 liviskgaqe ctktreferf qemcykayla irqhanlfin lfsmmlqsgm pelqsfddia
     1021 yirkllaldk teqealeyfm kqmndahhgg wttkmdwifh tikqhaln
//
```

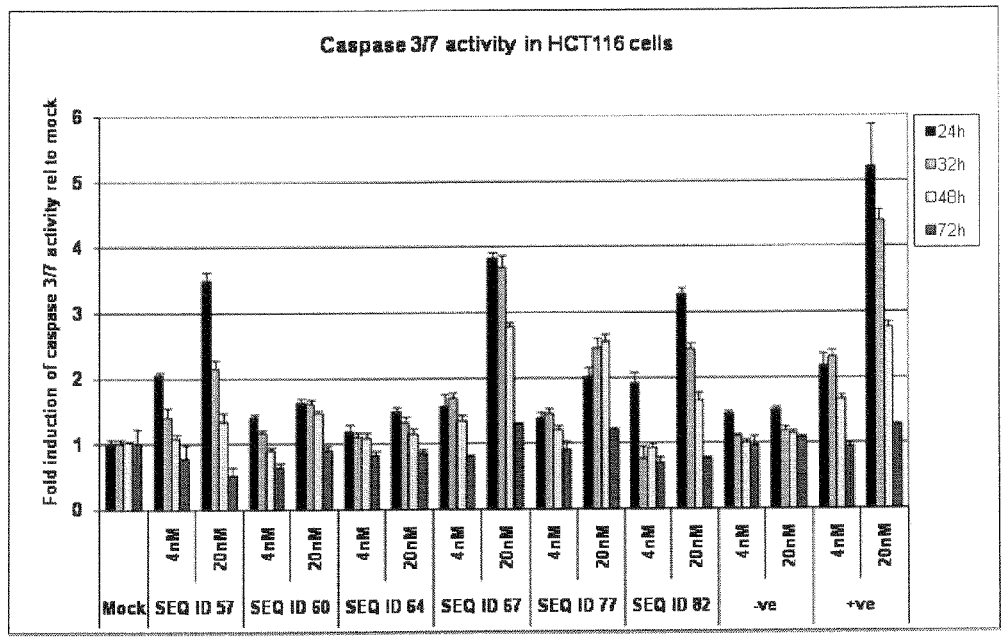
FIGURE 15
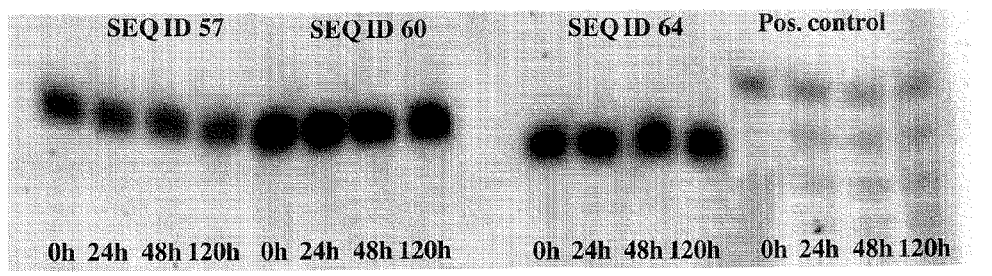
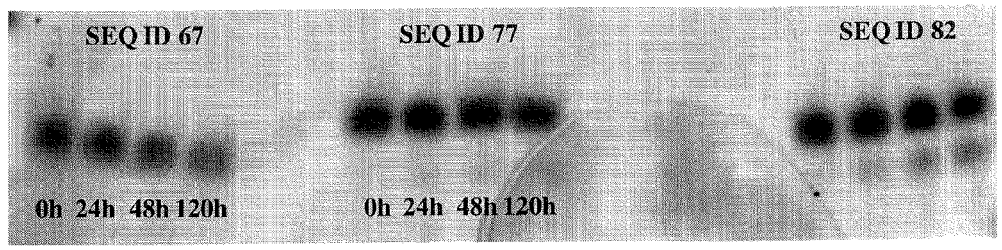
FIGURE 16

| Oligo | Sequence | Tm |
|---|---|---|
| SEQ 57 | 5'- $A_s^o$ $T_s^o$ $T_s^o$ $c_s$ $t_s$ $t_s$ $c_s$ $c_s$ $c_s$ $t_s$ $t_s$ $t_s$ $c_s$ $T_s^o$ $G_s^o$ $^mC^o$ -3' | 66.5 °C |
| SEQ 60 | 5'- $T_s^o$ $A_s^o$ $G_s^o$ $a_s$ $c_s$ $a_s$ $t_s$ $a_s$ $c_s$ $a_s$ $t_s$ $t_s$ $g_s$ $^mC_s^o$ $T_s^o$ $^mC^o$ -3' | 58.7 °C |
| SEQ 64 | 5'- $^mC_s^o$ $A_s^o$ $^mC_s^o$ $a_s$ $t_s$ $a_s$ $a_s$ $g_s$ $g_s$ $g_s$ $t_s$ $t_s$ $c_s$ $T_s^o$ $^mC_s^o$ $^mC^o$ -3' | 62.1 °C |
| SEQ 67 | 5'- $A_s^o$ $G_s^o$ $^mC_s^o$ $c_s$ $a_s$ $t_s$ $t_s$ $c_s$ $a_s$ $t_s$ $t_s$ $c_s$ $c_s$ $A_s^o$ $^mC_s^o$ $^mC^o$ -3' | 66.5 °C |
| SEQ 77 | 5'- $T_s^o$ $T_s^o$ $A_s^o$ $t_s$ $t_s$ $g_s$ $t_s$ $g_s$ $c_s$ $a_s$ $t_s$ $c_s$ $t_s$ $^mC_s^o$ $A_s^o$ $G^o$ -3' | 58.7 °C |
| SEQ 82 | 5'- $T_s^o$ $T_s^o$ $^mC_s^o$ $t_s$ $t_s$ $c_s$ $t_s$ $t_s$ $g_s$ $t_s$ $g_s$ $a_s$ $t_s$ $^mC_s^o$ $^mC_s^o$ $A^o$ -3' | 64.3 °C |

FIGURE 17

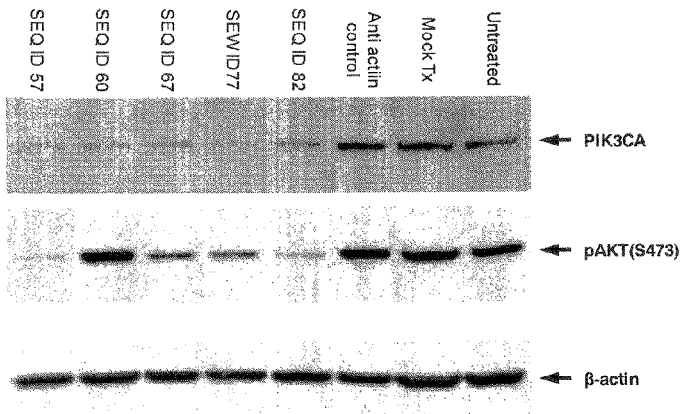

FIGURE 18

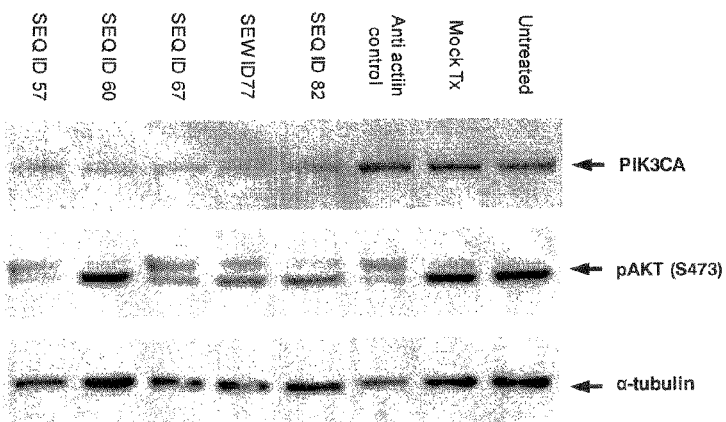

FIGURE 19

G1: saline (KD 0 ± 32.6%)
G2: SEQ ID 57, 3mg/kg (KD20.0 ± 23.3%)
G3: SEQ ID 57, 10mg/kg (KD61.8 ± 16.2%)
G6: SEQ ID 60, 3mg/kg (KD 26.6± 13.9%)
G7: SEQ ID 60, 10mg/kg (KD 65.7± 11.1 %)
G8: SEQ ID 60, 30mg/kg (KD 83.5 ± 8.1%)
G9: SEQ ID 60, 100mg/kg (KD 88.1± 3.7%)
G10: SEQ ID 67, 3mg/kg (KD 32.8± 36.9%)
G11: SEQ ID 67, 10mg/kg (KD 72.5 ± 15.5%)

G12: SEQ ID 67, 30mg/kg (KD 81.8 ± 17.3%)
G13: SEQ ID 67, 100mg/kg (KD 80.7 ± 4.2%)
G14: SEQ ID 77, 3mg/kg (KD 64.8± 18.1%)
G15: SEQ ID 77, 10mg/kg (KD 85.7 ± 5.6%)
G16: SEQ ID 77, 30mg/kg (KD 90.6± 6.9%)
G18: SEQ ID 82, 3mg/kg (KD 62.2 ± 26.4%)
G19: SEQ ID 82, 10mg/kg (KD 71.7 ± 9.7%)
G20: SEQ ID 82, 30mg/kg (KD 94.5 ± 11.7%)

RNA ANTAGONIST COMPOUNDS FOR THE MODULATION OF PIK3CA EXPRESSION

This application is a divisional application of U.S. application Ser. No. 12/323,744 filed Nov. 26, 2008, now U.S. Pat. No. 7,863,437 issued on Jan. 4, 2011 which claims the benefit under 35 U.S.C. §119(e) of U.S. Provisional Application Ser. No. 60/992,050, filed Dec. 3, 2007, the disclosure of which is incorporated herein by reference in its entirety.

FIELD OF INVENTION

The invention relates to oligomeric compounds (oligomers) that target PIK3CA mRNA in a cell, leading to reduced expression of PIK3CA. In particular, this invention relates to oligomeric compounds (oligomers), which target PIK3CA mRNA in a cell, leading to reduced expression of PIK3CA. Reduction of PIK3CA expression is beneficial for a range of medical disorders, such as hyperproliferative diseases such as cancer.

BACKGROUND

Phospatidylinositol 3-kinase (PI3K) is a ubiquitous lipid kinase involved in receptor signal transduction by tyrosine kinase receptors. PI3K comprises a large and complex family that includes 3 classes with multiple subunits and isoforms. The class I PI3Ks are composed of a Src homology-2 domain containing an 85 kDa regulatory subunit (p85) and a 100-kDa catalytic subunit (p110), which catalyses the phosphorylation of phosphoinositol 4-phosphate and phosphoinositol 4,5-phosphate at their D3 positions. The PI3K regulatory subunits include p85alpha and its truncated splice variants p50alpha and p55alpha, as well as p85beta and p55gamma; the catalytic subunits include p110alpha, p110beta, and p110delta. The human catalytic subunit p110alpha is encoded by the PIK3CA gene, located on the human chromosome 3 [Chr 3: 180.35-180.44 M bp] specifically [chr3:180,349,005-180,435,191 bp](NCBI reference sequence annotation) (3q26.3), which is frequently mutated in a variety of human cancers; PIK3CA has been shown to be mutated in 32% of colorectal cancers, 27% of glioblastomas, 25% of gastric cancers, 36% of hepatocellular carcinomas, 18-40% of breast cancers, 4-12% of ovarian cancers and 4% of lung cancers (Samuels et al., 2006). Most of these mutations map to three mutational hot-spots within the PIK3CA coding sequence, which are E542K, E545K and H1047R (Kang et al., 2005).

PI3K has been indicated in a wide range of cancers, such as colorectal carcinoma, where it is has been shown that the activation of PI3K/Akt is associated with colorectal carcinoma and can convert differentiated human gastric or colonic carcinoma cells to a less differentiated and more malignant phenotype (Rychahou et al 2006).

The effects of PI3K on tumor growth and progression are thought to be mediated by Aid, a downstream effector of PI3K. In humans there are three members of the Akt gene family, Akt 1, Akt 2 and Akt3. Aid is over expressed in a number of cancers, including colon, pancreatic, ovarian and some steroid hormone-insensitive breast cancers.

Inhibitors of proteins that are involved in the PI3K/Akt signalling, which have been suggested as potential therapeutic agents, include both siRNAs and antisense oligonucleotides (US2006/030536A), however to date most research in this area appears to have focused on the use of siRNAs.

WO2005/091849 describes antisense down-regulation of PI3K, however no specific antisense oligonucleotides are disclosed.

Zhang et al., 2004 (Cancer Biology and Therapy 3:12 1283-1289) discloses siRNAs targeting p110alpha and suggests its use in gene therapy in ovarian cancer.

Rychahou et al 2006 (Annals of Surgery 243833-844) discloses siRNA complexes targeting p85alpha and p110alpha which were found to decrease in vitro colon cancer cell survival and to increase apoptosis in human colon cancer cells, and decreased liver metastasis in in vivo experiments.

Meng et al., 2006 (Cellular Signalling 18 2262-2271) discloses siRNAs targeting p110alpha for inhibiting PI3K activity in ovarian cancer cells. The authors determined that inhibition of AKT 1 is sufficient to affect cell migration, invasion and proliferation.

Hsieh et al., 2004 (NAR 32 893-901) reports on the use of 148 siRNA duplexes targeting 30 genes within the PI3K pathway.

US 2005/0272682 discloses siRNA complexes targeting a phosphoinositide 3-kinase (PI3K) signal transduction pathway.

In certain embodiments, the invention provides highly efficient antisense oligonucleotides which target the PI3K pathway, specifically the PIK3CA mRNA, and in particular a new class of PIK3CA antagonists which have been selected based on the use of LNA chemistry, and/or by the selection of particularly effective target sites on the PIK3CA mRNA.

SUMMARY OF INVENTION

The invention provides an oligomer of 10-50 monomers, such as 10-30 monomers which comprises a first region of 10-30 monomers, wherein the sequence of the first region is at least 80% (e.g., 85%, 90%, 95%, 98%, or 99%) identical to the reverse complement of a target region of a nucleic acid which encodes a mammalian PIK3CA, such as a mammalian PIK3CA gene or mRNA, such as a nucleic acid have the sequence set forth in SEQ ID NO: 1 or naturally occurring variants thereof.

The invention provides for a conjugate comprising the oligomer according to the invention, and at least one non-nucleoside or non-polynucleotide moiety covalently attached to the oligomer.

The invention provides for a pharmaceutical composition comprising the oligomer or the conjugate according to the invention, and a pharmaceutically acceptable diluent, carrier, salt or adjuvant.

The invention provides for the oligomer or the conjugate according to the invention, for use as a medicament, such as for the treatment of hyperproliferative diseases, such as cancer.

The invention provides for the use of an oligomer or conjugate thereof according to the invention, for the manufacture of a medicament for the treatment of hyperproliferative diseases such as cancer.

The invention provides for a method of treating a hyperproliferative disease such as cancer, the method comprising administering an effective amount of an oligomer, a conjugate or a pharmaceutical composition according to the invention, to a patient suffering from, or susceptible to, said the hyperproliferative disease.

The invention provides for a method of inhibiting PIK3CA in a cell which is expressing PIK3CA, the method comprising contacting the cell in vitro or in vivo with an effective amount of an oligomer, or a conjugate according to the invention to effect the inhibition of PIK3CA expression in the cell.

The invention further provides for an oligomer according to the invention, for use in medicine.

The invention further provides for an oligomer according to the invention, for use for the treatment of one or more of the diseases referred to herein, such as a disease selected from the group consisting of hyperproliferative diseases, such as cancer.

Also disclosed are methods of treating a non-human animal or a human, suspected of having or being susceptible to a hyperproliferative disease, such as cancer and/or other hyperproliferative diseases, associated with the expression, or overexpression, of PIK3CA, by administering to the non-human animal or human a therapeutically or prophylactically effective amount of an oligomer, conjugate or composition of the invention. Further, methods of using oligomers for the inhibition of expression of PIK3CA, and for treatment of diseases associated with PIK3CA (e.g., PI3K) are provided.

The invention provides for a method for treating a disease selected from the group consisting of hyperproliferative diseases such as cancer; the method comprises administering an effective amount of an oligomer, a conjugate, or a pharmaceutical composition according to the invention to a patient in need thereof.

BRIEF DESCRIPTION OF FIGURES

FIG. 3. Sequence alignment of the human PIK3CA mRNA sequence, GenBank Accession number NM_006218 (SEQ ID NO: 1), and the mouse PIK3CA mRNA sequence, GenBank Accession number NM_008839 (SEQ ID NO: 106). Consensus sequence disclosed as SEQ ID NO: 164.

FIG. 4. Location of target regions on the human PIK3CA mRNA sequence (GenBank Accession number NM_006218) (SEQ ID NO: 1). Positions marked in grey are mutation hot-spots-1781, 1790 and 3297.

FIG. 5. SEQ ID NO: 1 Homo sapiens phosphoinositide-3-kinase, catalytic, alpha polypeptide (PIK3CA) mRNA, GenBank Accession number NM_006218, 3724 bp.

FIG. 6. SEQ ID NO 105. Homo sapiens phosphoinositide-3-kinase, catalytic, alpha polypeptide protein sequence (PIK3CA) GenBank Accession number NP_006209.

FIG. 7. SEQ ID NO 106. Mus musculus phosphatidylinositol 3-kinase, catalytic, alpha polypeptide (PIK3CA), mRNA. GenBank Accession number NM_008839.

FIG. 8. SEQ ID NO 107. Mus musculus phosphoinositide-3-kinase, catalytic, alpha polypeptide protein sequence (PIK3CA) GenBank Accession number NP_032865.

FIG. 9. SEQ ID NO 108. Macaca mulatta phosphatidylinositol 3-kinase, catalytic, alpha polypeptide (PIK3CA), mRNA. GenBank Accession number XM_001109162.

FIG. 10. SEQ ID NO 109. Macaca mulatta phosphoinositide-3-kinase catalytic, alpha polypeptide protein sequence (PIK3CA) GenBank Accession number XP_001109162.

FIG. 15. Caspase 3/7 activity in HCT116 cells after transfection with PIK3CA oligomers. Data are expressed as fold induction compared to mock.

FIG. 16. Plasma stability of PIK3CA oligonucleotides. The LNA oligonucleotides were incubated with mouse plasma at 37° C. and aliquots were taken at 0, 24, 48 and 120 h. The results were visualized by gel electrophoresis using an SDS-PAGE gel.

FIG. 17. Tm determination of PIK3CA oligonucleotides hybridised to a target region of a target nucleic acid. Bold, uppercase letters with a superscript "o" to the right represent β-D-oxy LNA monomers. MC represents LNA monomers with 5-methylcytosine bases. Subscript "s" represents a phosphorothioate linkage. Lowercase letters represent DNA monomers.

FIG. 18. Down-regulation of PIK3CA protein and pAkt in A549 cells

FIG. 19. Down-regulation of PIK3CA protein and pAkt in 15PC3 cells

DETAILED DESCRIPTION OF INVENTION

The Oligomer

Figure 1:
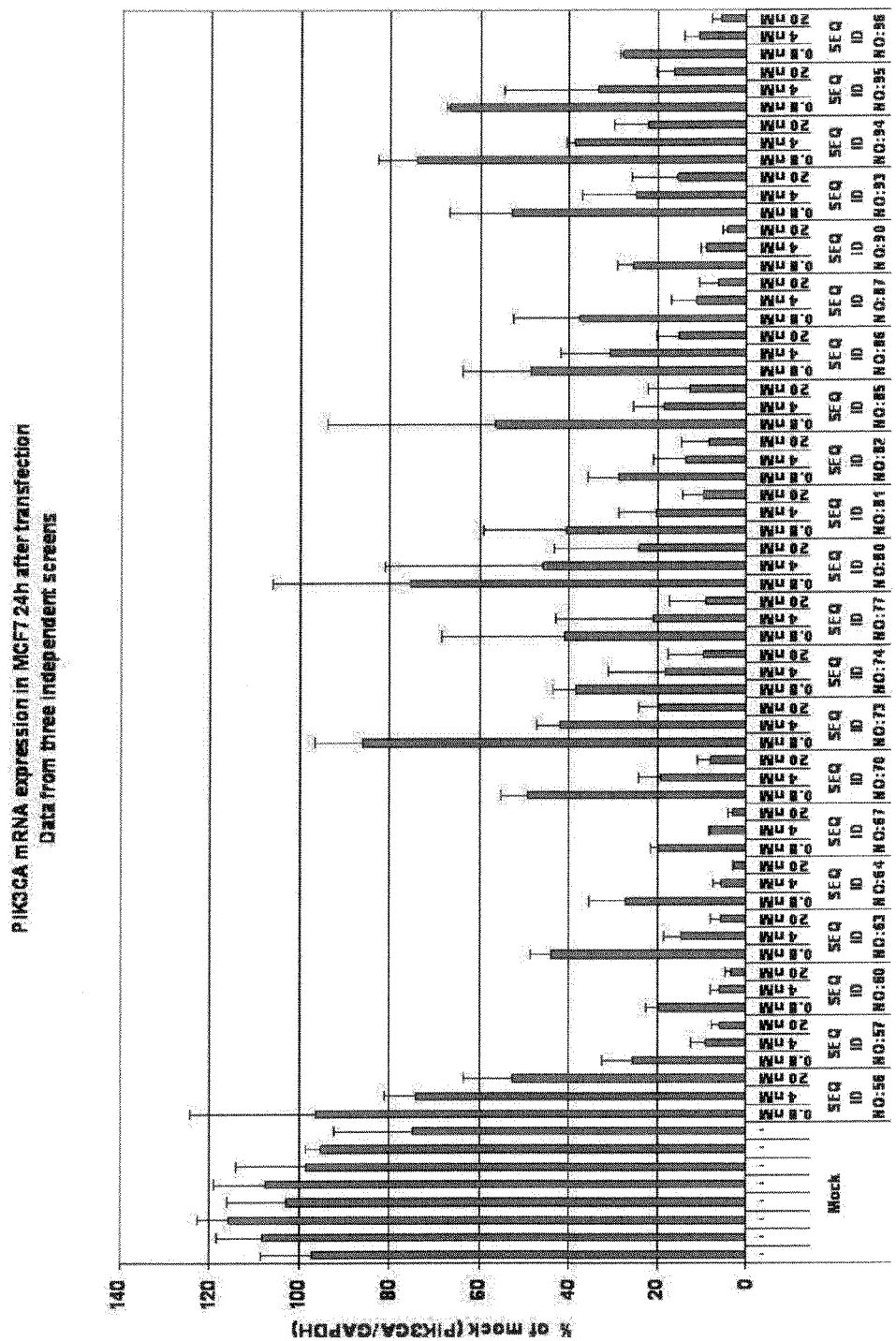
FIG. 1. Oligonucleotides presented in Table 5 were evaluated for their potential to knock down the PIK3CA mRNA at concentrations of 0.8 nM, 4 nM and 20 nM in MCF7 cells 24 hours after transfection using Real-time PCR. All results were normalised to GAPDH and inhibition of PIK3CA mRNA is shown as percent of mock-transfected control. Results shown are the average of results from three independent experiments.

The invention employs oligomeric compounds (referred herein as oligomers), for use in modulating the function of nucleic acid molecules encoding mammalian PIK3CA, such as the PIK3CA nucleic acid having the sequence shown in SEQ ID NO.: 1, and naturally occurring variants of such nucleic acid molecules encoding mammalian PIK3CA. The term "oligomer" in the context of the present invention, refers to a molecule formed by covalent linkage of two or more monomers (i.e. an oligonucleotide). In some embodiments, the oligomer consists of or comprises from 10-30 monomers.

The term "monomer" includes both nucleosides and deoxynucleosides (collectively, "nucleosides") that occur naturally in nucleic acids and that do not contain either modified sugars or modified nucleobases, i.e., compounds in which a ribose sugar or deoxyribose sugar is covalently bonded to a naturally-occurring, unmodified nucleobase (base) moiety (i.e., the purine and pyrimidine heterocycles adenine, guanine, cytosine, thymine or uracil) and "nucleoside analogues," which are nucleosides that either do occur naturally in nucleic acids or do not occur naturally in nucleic acids, wherein either the sugar moiety is other than a ribose or a deoxyribose sugar (such as bicyclic sugars or 2' modified sugars, such as 2' substituted sugars), or the base moiety is modified (e.g., 5-methylcytosine), or both.

An "RNA monomer" is a nucleoside containing a ribose sugar and an unmodified nucleobase.

A "DNA monomer" is a nucleoside containing a deoxyribose sugar and an unmodified nucleobase.

A "Locked Nucleic Acid monomer," "locked monomer," or "LNA monomer" is a nucleoside analogue having a bicyclic sugar, as further described herein below.

The terms "corresponding nucleoside analogue" and "corresponding nucleoside" indicate that the base moiety in the nucleoside analogue and the base moiety in the nucleoside are identical. For example, when the "nucleoside" contains a 2-deoxyribose sugar linked to an adenine, the "corresponding nucleoside analogue" contains, for example, a modified sugar linked to an adenine base moiety.

The terms "oligomer," "oligomeric compound," and "oligonucleotide" are used interchangeably in the context of the invention, and refer to a molecule formed by covalent linkage of two or more contiguous monomers by, for example, a phosphate group (forming a phosphodiester linkage between nucleosides) or a phosphorothioate group (forming a phosphorothioate linkage between nucleosides). The oligomer consists of, or comprises, 10-50 monomers, such as 10-30 monomers.

In some embodiments, an oligomer comprises nucleosides, or nucleoside analogues, or mixtures thereof as referred to herein. An "LNA oligomer" or "LNA oligonucleotide" refers to an oligonucleotide containing one or more LNA monomers.

The terms "corresponding nucleoside analogue" and "corresponding nucleoside" indicate that the base moiety in the nucleoside analogue and the base moiety in the nucleoside are identical. For example, when the "nucleoside" contains a 2-deoxyribose sugar linked to an adenine, the "corresponding nucleoside analogue" contains, for example, a modified sugar linked to an adenine base moiety.

In some embodiments, an oligomer comprises nucleosides, or nucleoside analogues, or mixtures thereof as referred to herein. An "LNA oligomer" or "LNA oligonucleotide" refers to an oligonucleotide containing one or more LNA monomers.

Nucleoside analogues that are optionally included within oligomers may function similarly to corresponding nucleosides, or may have specific improved functions. Oligomers wherein some or all of the monomers are nucleoside analogues are often preferred over native forms because of several desirable properties of such oligomers, such as the ability to penetrate a cell membrane, good resistance to extra- and/or intracellular nucleases and high affinity and specificity for the nucleic acid target. LNA monomers are particularly preferred, for example, for conferring several of the above-mentioned properties.

In various embodiments, one or more nucleoside analogues present within the oligomer are "silent" or "equivalent" in function to the corresponding natural nucleoside, i.e., have no functional effect on the way the oligomer functions to inhibit target gene expression. Such "equivalent" nucleoside analogues are nevertheless useful if, for example, they are easier or cheaper to manufacture, or are more stable under storage or manufacturing conditions, or can incorporate a tag or label. Typically, however, the analogues will have a functional effect on the way in which the oligomer functions to inhibit expression; for example, by producing increased binding affinity to the target region of the target nucleic acid and/or increased resistance to intracellular nucleases and/or increased ease of transport into the cell.

Thus, in various embodiments, oligomers according to the invention comprise nucleoside monomers and at least one nucleoside analogue monomer, such as an LNA monomer, or other nucleoside analogue monomers.

The term "at least one" comprises the integers larger than or equal to 1, such as 1, 2, 3, 4, 5, 6, 7, 8, 9, 10, 11, 12, 13, 14, 15, 16, 17, 18, 19, 20 and so forth. In various embodiments, such as when referring to the nucleic acid or protein targets of the compounds of the invention, the term "at least one" includes the terms "at least two" and "at least three" and "at least four." Likewise, in some embodiments, the term "at least two" comprises the terms "at least three" and "at least four."

In some embodiments, the oligomer comprises or consists of 10, 11, 12, 13, 14, 15, 16, 17, 18, 19, 20, 21, 22, 23, 24, 25, 26, 27, 28, 29 or 30 contiguous monomers.

In some embodiments, the oligomer comprises or consists of 10-22 contiguous monomers, such as 12-18 contiguous monomers, such as 13-17 or 12-16 contiguous monomers, such as 13, 14, 15, 16 contiguous monomers.

In certain embodiments, the oligomer comprises or consists of 10, 11, 12, 13, or 14 contiguous monomers.

In various embodiments, the oligomer according to the invention consists of no more than 22 monomers, such as no more than 20 monomers, such as no more than 18 monomers, such as 15, 16 or 17 monomers. In some embodiments, the oligomer of the invention comprises less than 20 monomers.

In various embodiments, the compounds of the invention do not comprise RNA monomers.

In various embodiments, the compounds according to the invention are linear molecules or are linear as synthesised. The oligomer, in such embodiments, is a single stranded molecule, and typically does not comprise short regions of, for example, at least 3, 4 or 5 contiguous monomers, which are complementary to another region within the same oligomer such that the oligomer forms an internal duplex. In some embodiments, the oligomer is essentially not double stranded, i.e., is not a siRNA.

In some embodiments, the oligomer of the invention consists of a contiguous stretch of monomers, the sequence of which is identified by a SEQ ID NO disclosed herein (see, e.g., Tables 2-5). In other embodiments, the oligomer comprises a first region, the region consisting of a contiguous stretch of monomers, and one or more additional regions which consist of at least one additional monomer. In some embodiments, the sequence of the first region is identified by a SEQ ID NO disclosed herein.

Gapmer Design

Typically, the oligomer of the invention is a gapmer.

A "gapmer" is an oligomer which comprises a contiguous stretch of monomers capable of recruiting an RNAse (e.g., such as RNAseH) as further described herein below, such as a region of at least 6 or 7 DNA monomers, referred to herein as region B, wherein region B is flanked both on its 5' and 3' ends by regions respectively referred to as regions A and C, each of regions A and C comprising or consisting of nucleoside analogues, such as affinity-enhancing nucleoside analogues, such as 1-6 nucleoside analogues.

Typically, the gapmer comprises regions, from 5' to 3', A-B-C, or optionally A-B-C-D or D-A-B-C, wherein: region A consists of or comprises at least one nucleoside analogue, such as at least one LNA monomer, such as 1-6 nucleoside analogues, such as LNA monomers, and region B consists of or comprises at least five contiguous monomers which are capable of recruiting RNAse (when formed in a duplex with a complementary target region of the target RNA molecule, such as the mRNA target), such as DNA monomers; region C consists of or comprises at least one nucleoside analogue, such as at least one LNA monomer, such as 1-6 nucleoside analogues, such as LNA monomers; and region D, when present, consists of or comprises 1, 2 or 3 monomers, such as DNA monomers.

In various embodiments, region A consists of 1, 2, 3, 4, 5 or 6 nucleoside analogues, such as LNA monomers, such as 2-5 nucleoside analogues, such as 2-5 LNA monomers, such as 3 or 4 nucleoside analogues, such as 3 or 4 LNA monomers; and/or region C consists of 1, 2, 3, 4, 5 or 6 nucleoside analogues, such as LNA monomers, such as 2-5 nucleoside analogues, such as 2-5 LNA monomers, such as 3 or 4 nucleoside analogues, such as 3 or 4 LNA monomers.

In certain embodiments, region B consists of or comprises 5, 6, 7, 8, 9, 10, 11 or 12 contiguous monomers which are capable of recruiting RNAse, or 6-10, or 7-9, such as 8 contiguous monomers which are capable of recruiting RNAse. In certain embodiments, region B consists of or comprises at least one DNA monomer, such as 1-12 DNA monomers, preferably 4-12 DNA monomers, more preferably 6-10 DNA monomers, such as 7-10 DNA monomers, most preferably 8, 9 or 10 DNA monomers.

In various embodiments, region A consists of 3 or 4 nucleoside analogues, such as LNA monomers, region B consists of 7, 8, 9 or 10 DNA monomers, and region C consists of 3 or 4 nucleoside analogues, such as LNA monomers. Such designs include (A-B-C) 3-10-3, 3-10-4, 4-10-3, 3-9-3, 3-9-4, 4-9-3, 3-8-3, 3-8-4, 4-8-3, 3-7-3, 3-7-4, 4-7-3, and may further include region D, which may have one or 2 monomers, such as DNA monomers.

Further gapmer designs are disclosed in WO2004/046160, which is hereby incorporated by reference.

US provisional application, 60/977,409, hereby incorporated by reference, refers to 'shortmer' gapmer oligomers. In some embodiments, oligomers presented here may be such shortmer gapmers.

In certain embodiments, the oligomer consists of 10, 11, 12, 13 or 14 contiguous monomers, wherein the regions of the oligomer have the pattern (5'-3'), A-B-C, or optionally A-B-C-D or D-A-B-C, wherein: region A consists of 1, 2 or 3 nucleoside analogue monomers, such as LNA monomers; region B consists of 7, 8 or 9 contiguous monomers which are capable of recruiting RNAse when formed in a duplex with a complementary RNA molecule (such as a mRNA target); and region C consists of 1, 2 or 3 nucleoside analogue monomers, such as LNA monomers. When present, region D consists of a single DNA monomer.

In certain embodiments, region A consists of 1 LNA monomer. In certain embodiments, region A consists of 2 LNA monomers. In certain embodiments, region A consists of 3 LNA monomers. In certain embodiments, region C consists of 1 LNA monomer. In certain embodiments, region C consists of 2 LNA monomers. In certain embodiments, region C consists of 3 LNA monomers. In certain embodiments, region B consists of 7 nucleoside monomers. In certain embodiments, region B consists of 8 nucleoside monomers. In certain embodiments, region B consists of 9 nucleoside monomers. In certain embodiments, region B comprises 1-9 DNA monomers, such as 2, 3, 4, 5, 6, 7 or 8 DNA monomers. In certain embodiments, region B consists of DNA monomers. In certain embodiments, region B comprises at least one LNA monomer which is in the alpha-L configuration, such as 2, 3, 4, 5, 6, 7, 8 or 9 LNA monomers in the alpha-L-configuration. In certain embodiments, region B comprises at least one alpha-L-oxy LNA monomer. In certain embodiments, all the LNA monomers in region B that are in the alpha-L-configuration are alpha-L-oxy LNA units. In certain embodiments, the number of monomers present in the A-B-C regions are selected from the group consisting of (nucleoside analogue monomers—region B—nucleoside analogue monomers): 1-8-1, 1-8-2, 2-8-1, 2-8-2, 3-8-3, 2-8-3, 3-8-2, 4-8-1, 4-8-2, 1-8-4, 2-8-4, or; 1-9-1, 1-9-2, 2-9-1, 2-9-2, 2-9-3, 3-9-2, 1-9-3, 3-9-1, 4-9-1, 1-9-4, or; 1-10-1, 1-10-2, 2-10-1, 2-10-2, 1-10-3, 3-10-1. In certain embodiments, the number of monomers present in the A-B-C regions of the oligomer of the invention is selected from the group consisting of: 2-7-1, 1-7-2, 2-7-2, 3-7-3, 2-7-3, 3-7-2, 3-7-4, and 4-7-3. In certain embodiments, each of regions A and C consists of two LNA monomers, and region B consists of 8 or 9 nucleoside monomers, preferably DNA monomers.

In various embodiments, other gapmer designs include those where regions A and/or C consists of 3, 4, 5 or 6 nucleoside analogues, such as monomers containing a 2'-O-methoxyethyl-ribose sugar (2'-MOE) or monomers containing a 2'-fluoro-deoxyribose sugar, and region B consists of 8, 9, 10, 11 or 12 nucleosides, such as DNA monomers, where regions A-B-C have 5-10-5 or 4-12-4 monomers. Further gapmer designs are disclosed in WO2007/146511A2, hereby incorporated by reference.

Internucleoside Linkages

The monomers of the oligomers described herein are coupled together via linkage groups. Suitably, each monomer is linked to the 3' adjacent monomer via a linkage group.

The terms "linkage group" or "internucleoside linkage" means a group capable of covalently coupling together two contiguous monomers. Specific and preferred examples include phosphate groups (forming a phosphodiester between adjacent nucleoside monomers) and phosphorothioate groups (forming a phosphorothioate linkage between adjacent nucleoside monomers).

Suitable linkage groups include those listed in PCT/DK2006/000512, for example in the first paragraph of page 34 of PCT/DK2006/000512 (hereby incorporated by reference).

It is, in various embodiments, preferred to modify the linkage group from its normal phosphodiester to one that is more resistant to nuclease attack, such as phosphorothioate or boranophosphate—these two being cleavable by RNaseH, thereby permitting RNase-mediated antisense inhibition of expression of the target gene.

In some embodiments, suitable sulphur (S) containing linkage groups as provided herein are preferred. In various embodiments, phosphorothioate linkage groups are preferred, particularly for the gap region (B) of gapmers. In certain embodiments, phosphorothioate linkages are used to link together monomers in the flanking regions (A and C). In various embodiments, phosphorothioate linkages are used for linking regions A or C to region D, and for linking together monomers within region D.

In various embodiments, regions A, B and C comprise linkage groups other than phosphorothioate, such as phosphodiester linkages, particularly, for instance when the use of nucleoside analogues protects the linkage groups within regions A and C from endo-nuclease degradation—such as when regions A and C comprise LNA monomers.

In various embodiments, adjacent monomers of the oligomer are linked to each other by means of phosphorothioate groups.

It is recognised that the inclusion of phosphodiester linkages, such as one or two linkages, into an oligomer with a phosphorothioate backbone, particularly with phosphorothioate linkage groups between or adjacent to nucleoside analogue monomers (typically in region A and/or C), can modify the bioavailability and/or bio-distribution of an oligomer—see WO2008/053314, hereby incorporated by reference.

In some embodiments, such as the embodiments referred to above, where suitable and not specifically indicated, all remaining linkage groups are either phosphodiester or phosphorothioate, or a mixture thereof.

In some embodiments all the internucleoside linkage groups are phosphorothioate.

When referring to specific gapmer oligonucleotide sequences, such as those provided herein, it will be understood that, in various embodiments, when the linkages are phosphorothioate linkages, alternative linkages, such as those disclosed herein may be used, for example phosphate (phosphodiester) linkages may be used, particularly for linkages between nucleoside analogues, such as LNA monomers. Likewise, in various embodiments, when referring to specific gapmer oligonucleotide sequences, such as those provided herein, when one or more monomers in region C comprises a 5-methylcytosine base, other monomers in that region may contain unmodified cytosine bases.

Target Nucleic Acid

The terms "nucleic acid" and "polynucleotide" are used interchangeably herein, and are defined as a molecule formed by covalent linkage of two or more monomers, as above-described. Including 2 or more monomers, "nucleic acids" may be of any length, and the term is generic to "oligomers", which have the lengths described herein. The terms "nucleic acid" and "polynucleotide" include single-stranded, double-stranded, partially double-stranded, and circular molecules.

The term "target nucleic acid", as used herein, refers to DNA or RNA (e.g., mRNA or pre-mRNA) encoding a mammalian PIK3CA polypeptide, such as human PIK3CA, such as the nucleic acid having the sequence shown in SEQ ID NO: 1, and naturally occurring allelic variants of such nucleic acids. In certain embodiments, the target nucleic acid encodes a mouse PIK3CA polypeptide. In some embodiments, target nucleic acid refers to DNA or RNA that encodes a mammalian PIK3CA polypeptide and DNA or RNA that encodes a mammalian beta-catenin polypeptide. The oligomers of the invention are typically capable of hybridising to the target nucleic acid(s).

The term "naturally occurring variant thereof" refers to variants of the PIK3CA polypeptide or nucleic acid sequence which exist naturally within the defined taxonomic group, such as mammalian, such as mouse, monkey, and preferably human PIK3CA. Typically, when referring to "naturally occurring variants" of a polynucleotide the term also encompasses any allelic variant of the PIK3CA encoding genomic DNA which is found at the Chromosome 3 [Chr 3: 180.35-180.44 M bp] specifically [Chr 3: 180,349,005-180,435, 191 bp] (NCBI reference sequence annotation) (3q26.3) by chromosomal translocation or duplication, and the RNA, such as mRNA, derived therefrom. "Naturally occurring variants" may also include variants derived from alternative splicing of the PIK3CA mRNA. When referenced to a specific polypeptide sequence, e.g., the term also includes naturally occurring forms of the protein which may therefore be processed, e.g. by co- or post-translational modifications, such as signal peptide cleavage, proteolytic cleavage, glycosylation, etc. In certain embodiments, variant target nucleic acids, have at least 60%, more preferably at least 70%, more preferably at least 80%, more preferably at least 85%, more preferably at least 90%, more preferably at least 95% sequence homology (also, identity) to wild-type PIK3CA. Typically, an oligomer of the invention corresponding to (i.e., that is complementary to and binds to) a target region that contains one or more mutations compared to the wild-type PIK3CA sequence is still capable of down-regulating PIK3CA expression. In certain embodiments, the mutation is "silent" (i.e. is not associated with an altered phenotype or disease). In various embodiments, the mutation is "functional" (i.e., disease-associated). In various embodiments, the naturally occurring variant is an allelic variant.

Particular variants of PIK3CA, which in some embodiments are targeted by the oligomers of the invention, contain spontaneous point mutations which are associated with hyperproliferative diseases such as cancer. In certain embodiments, such point mutations are those which result in amino acid substitutions at positions E542, E545 or H1047, such as point mutations which result in the amino acid substitutions E542K, E545K or H1047R. By designing oligomers which target (e.g., are fully complementary to) one or more target regions of PIK3CA mRNA which comprises such a point mutation, in certain embodiments, oligomers of the invention preferentially down-regulate (i.e., by inhibiting) the expression of such variant forms of PIK3CA mRNA. In certain embodiments, the oligomers that target these variant forms of PIK3CA selectively down-regulate one or more variant PIK3CA mRNAs (e.g., those having mutations at positions E542, E545 or H1047) that are associated with a cancer phenotype.

In certain embodiments, the PIK3CA gene or mRNA target nucleic acid comprises a target region containing a single base substitution at position 1781, 1790 or 3297 of SEQ ID NO 1. In such embodiments, the nucleobase of the monomer at position 1781 of SEQ ID NO: 1 is other than G (e.g., A, C or T/U) the nucleobase of the monomer at position 1790 is other than G, or the nucleobase of the monomer at position 3297 is other than A.

In certain embodiments, the oligomer according to the invention comprises a sequence that is fully complementary to a target region that includes a point mutation at position 1781 of SEQ ID NO: 1. In these embodiments, the nucleobase of the monomer in the oligomer that base-pairs with the nucleobase of the monomer at position 1781 of SEQ ID NO: 1 is not C (e.g., the oligomer is not fully complementary to the wild-type target region. In other embodiments, the oligomer of the invention comprises one mismatch when compared to the best aligned target region of SEQ ID NO: 1 that includes a point mutation at position 1781 of SEQ ID NO: 1.

In various embodiments, the oligomer according to the invention comprises a sequence that is fully complementary to a target region that includes a point mutation at position 1790 of SEQ ID NO 1. In these embodiments, the nucleobase of the monomer of the oligomer that base-pairs with the nucleobase of the monomer at position 1790 in SEQ ID NO:1 is not C (e.g., the oligomer is not fully complementary to the wild-type target region. In other embodiments, the oligomer comprises one mismatch when compared to the best-aligned target region of SEQ ID NO: 1 that includes a point mutation at position 1790 of SEQ ID NO:1.

In various embodiments, the oligomer according to the invention comprises a sequence that is fully complementary to a target region that includes a point mutation at position 3297 of SEQ ID NO: 1, wherein the nucleobase of the monomer of the oligomer which base-pairs with the nucleobase of the monomer at position 3297 is not T (e.g., the oligomer is not fully complementary to the wild-type target region). In other embodiments, the oligomer of the invention comprises one mismatch when compared to the best-aligned target region of SEQ ID NO: 1 that includes a point mutation at position 3297.

In some embodiments, for example when used in research or diagnostics, the "target nucleic acid" is a cDNA or a synthetic oligonucleotide derived from the above DNA or RNA nucleic acid targets. It will be recognised that the nucleic acid having the sequence as set forth in SEQ ID NO: 1 is a cDNA, and as such, has the same base sequence as the mature mRNA target, although uracil (U) bases are replaced by thymidine (T) bases in the cDNA.

In certain embodiments, oligomers described herein bind to a region of the target nucleic acid (the "target region") by either Watson-Crick base pairing, Hoogsteen hydrogen bonding, or reversed Hoogsteen hydrogen bonding, between the monomers of the oligomer and monomers of the target nucleic acid. Such binding is also referred to as "hybridisation." Unless otherwise indicated, binding is by Watson-Crick pairing of complementary bases (i.e., adenine with thymine (DNA) or uracil (RNA), and guanine with cytosine), and the Oligomer binds to the target region because the sequence of the oligomer is identical to, or partially-identical to, the sequence of the reverse complement of the target region; for purposes herein, the oligomer is said to be "complementary" or "partially complementary" to the target region, and the percentage of "complementarity" of the oligomer sequence to that of the target region is the percentage "identity" to the reverse complement of the sequence of the target region.

Unless otherwise made clear by context, the "target region" herein will be the region of the target nucleic acid having the sequence that best aligns with the reverse complement of the sequence of the specified oligomer (or region thereof), using the alignment program and parameters described herein below.

In determining the degree of "complementarity" between oligomers of the invention (or regions thereof) and the target region of the nucleic acid which encodes mammalian PIK3CA, such as those disclosed herein, the degree of "complementarity" (also, "homology") is expressed as the percentage identity between the sequence of the oligomer (or region thereof) and the reverse complement of the sequence of the target region that best aligns therewith. The percentage is calculated by counting the number of aligned bases that are identical as between the 2 sequences, dividing by the total number of contiguous monomers in the oligomer, and multiplying by 100. In such a comparison, if gaps exist, it is preferable that such gaps are merely mismatches rather than areas where the number of monomers within the gap differs between the oligomer of the invention and the target region.

Amino acid and polynucleotide alignments, percentage sequence identity, and degree of complementarity may be determined for purposes of the invention using the ClustalW algorithm using standard settings: Method: EMBOSS::water (local): Gap Open=10.0, Gap extend=0.5, using Blosum 62 (protein), or DNAfull for nucleoside/nucleobase sequences.

As will be understood, depending on context, "mismatch" refers to a non-identity in sequence (as, for example, between the nucleobase sequence of an oligomer and the reverse complement of the target region to which it binds; as for example, between the base sequence of two aligned PIK3CA encoding nucleic acids), or to noncomplementarity in sequence (as, for example, between an oligomer and the target region to which binds).

Suitably the oligomer of the invention or conjugate thereof is capable of down-regulating (i.e., by inhibiting) expression of the PIK3CA gene. In various embodiments, the oligomer of the invention can effect the inhibition of PIK3CA, typically in a mammalian cell, such as a human cell. In certain embodiments, the oligomers of the invention or conjugates thereof bind to the target nucleic acid and effect inhibition of expression of at least 10% or 20% compared to the expression level of PIK3CA in a cell immediately prior to dosing of the oligomer, more preferably at least a 30%, 40%, 50%, 60%, 70%, 80%, 90% or 95% inhibition compared to the expression level of PIK3CA in a cell immediately prior to dosing of the oligomer. In some embodiments, such inhibition is seen when using from about 0.04 nM to about 25 nM, such as from about 0.8 nM to about 20 nM concentration of the oligomer or conjugate.

In various embodiments, the inhibition of expression is less than 100% (i.e., less than complete inhibition of expression), such as less than 98% inhibition, less than 95% inhibition, less than 90% inhibition, less than 80% inhibition, such as less than 70% inhibition. In various embodiments, modulation of gene expression level can be determined by measuring protein levels, e.g. by methods such as SDS-PAGE followed by western blotting using suitable antibodies raised against the target protein. Alternatively, in certain embodiments, modulation of PIK3CA expression levels can be determined by measuring levels of mRNA. e.g. by northern blotting or quantitative RT-PCR. When measuring via mRNA levels, the level of down-regulation when using an appropriate dosage, such as from about 0.04 nM to about 25 nM, such as from about 0.8 nM to about 20 nM concentration, is, in some embodiments, typically to a level of 10-20% the expression levels in the absence of the compound or conjugate of the invention.

The invention therefore provides a method of down-regulating (e.g., by inhibiting) the expression of PIK3CA protein and/or mRNA in a cell which is expressing PIK3CA protein and/or mRNA, the method comprising contacting the cell with an effective amount of an oligomer or conjugate according to the invention to down-regulate or inhibit the expression of PIK3CA protein and/or mRNA in the cell. Suitably, the cell is a mammalian cell such as a human cell. The administration may occur, in some embodiments, in vitro. The administration may occur, in some embodiments, in vivo.

Alternatively, in certain embodiments, the invention provides for a method of inhibiting PIK3CA and beta-catenin in a cell which is expressing both PIK3CA and beta-catenin, the method comprising contacting the cell in vitro or in vivo with an effective amount of an oligomer, or a conjugate according to the invention to effect the inhibition of PIK3CA and beta-catenin expression in the cell. Suitably, the oligomer which is capable of inhibiting or down-regulating both PIK3CA and beta-catenin in a cell has significant identity to the reverse complement of a target region of a PIK3CA nucleic acid and to the reverse complement of a target region of a beta-catenin nucleic acid, such as an oligomer with the sequence of nucleobases set forth in SEQ ID NO: 82.

Oligomer Sequences

In certain embodiments, the oligomers of the invention have sequences that are identical to a sequence selected from the group consisting of SEQ ID NOs: 2-16, 17-28, 110-124, 125-136, 149-159 and 160. In various embodiments, the oligomers of the invention have base sequences that are selected from the group consisting of SEQ ID NOs: 29-55 and 56-148. In various embodiments, the oligomer has the sequence of SEQ ID NO: 67 or SEQ ID NO: 77. Further provided are target nucleic acids (e.g., DNA or mRNA encoding AR) that contain target regions that are complementary or partially-complementary to one or more of the oligomers of the invention. In certain embodiments, the oligomers bind to variants of PIK3CA target regions, such as allelic variants. In some embodiments, a variant of PIK3CA target region has at least 60%, more preferably at least 70%, more preferably at least 80%, more preferably at least 85%, more preferably at least 90%, more preferably at least 91%, at least 92%, at least 93%, at least 94%, at least 95% sequence identity to the target region in wild-type PIK3CA. Thus, in other embodiments, the oligomers of the invention have sequences that differ in 1, 2 or 3 bases when compared to a sequence selected from the group consisting of SEQ ID NOs: 2-16, 17-28, 110-124, 125-136, 149-159 and 160. Typically, an oligomer of the invention that binds to a variant of a PIK3CA target region is capable of inhibiting (e.g., by down-regulating) PIK3CA.

In other embodiments, oligomers of the invention are LNA oligomers, for example, those oligomers having the sequences shown in SEQ ID NOs: 29-104 and 137-148. In various embodiments, the oligomers of the invention are potent inhibitors of PIK3CA mRNA and protein expression. In various embodiments, oligomers of the invention are LNA oligomers having the sequences of SEQ ID NO: 67 or SEQ ID NO: 77.

In various embodiments, the oligomer comprises or consists of a region having a base sequence which is identical or partially identical to the sequence of the reverse complement of a target region in SEQ ID NO: 1. In various embodiments, the oligomer comprises or consists of a region having a sequence selected from the group consisting of SEQ ID NOS: 2-16, 17-28, 110-124, 125-136, 149-159 and 160.

In certain embodiments, the oligomer comprises or consists of a region having a base sequence which is fully complementary (perfectly complementary) to a target region of a nucleic acid which encodes a mammalian PIK3CA.

However, in some embodiments, the oligomer includes 1, 2, 3, or 4 (or more) mismatches as compared to the best-aligned target region of a PIK3CA target nucleic acid, and still sufficiently binds to the target region to effect inhibition of PIK3CA mRNA or protein expression. The destabilizing effect of mismatches on Watson-Crick hydrogen-bonded duplex may, for example, be compensated by increased length of the oligomer and/or an increased number of nucleoside analogues, such as LNA monomers, present within the oligomer.

In various embodiments, the oligomer base sequence comprises no more than 3, such as no more than 2 mismatches compared to the base sequence of the best-aligned target region of, for example, a target nucleic acid which encodes a mammalian PIK3CA.

In some embodiments, the oligomer base sequence comprises no more than a single mismatch when compared to the base sequence of the best-aligned target region of a nucleic acid which encodes a mammalian PIK3CA.

In various embodiments, the base sequence of the oligomer of the invention, or of a first region thereof, is preferably at least 80% identical to a base sequence selected from the group consisting of SEQ ID NOS: 2-16, 17-28, 110-124, 125-136, 149-159 and 160, such as at least 85%, at least 90%, at least 91%, at least 92%, at least 93%, at least 94%, at least 95%, at least 96% identical, such as 100% identical.

In certain embodiments, the base sequence of the oligomer of the invention or of a first region thereof is at least 80% identical to the base sequence of the reverse complement of a target region present in SEQ ID NO: 1, such as at least 85%, at least 90%, at least 91%, at least 92% at least 93%, at least 94%, at least 95%, at least 96% identical, at least 97% identical, at least 98% identical, at least 99% identical, such as 100% identical.

In various embodiments, the base sequence of the oligomer of the invention, or of a first region thereof, is preferably at least 80% complementary to a target region of SEQ ID NO: 1, such as at least 85%, at least 90%, at least 91%, at least 92%, at least 93%, at least 94%, at least 95%, at least 96% complementary, at least 97% complementary, at least 98% complementary, at least 99% complementary, such as 100% complementary (perfectly complementary).

In various embodiments, the sequence of the oligomer (or a first region thereof) is selected from the group consisting of SEQ ID NOS: 2, 3, 4, 5, 6, 7, 8, 9, 10, 11, 12, 13, 14, 15, 16, 17, 18, 19, 20, 21, 22, 23, 24, 25, 26 and 28, or is selected from the group consisting of at least 10 contiguous monomers of SEQ ID NOS: 2, 3, 4, 5, 6, 7, 8, 9, 10, 11, 12, 13, 14, 15, 16, 17, 18, 19, 20, 21, 22, 23, 24, 25, 26 and 28. In other embodiments, the sequence of the oligomer (or of a first region thereof) comprises one, two, or three base moieties that differ from those in oligomers having sequences of SEQ ID NOs: 2, 3, 4, 5, 6, 7, 8, 9, 10, 11, 12, 13, 14, 15, 16, 17, 18, 19, 20, 21, 22, 23, 24, 25, 26 and 28, or the sequences of at least 10 contiguous monomers thereof, when optimally aligned with the selected sequence or region thereof.

In various embodiments, the sequence of the oligomer (or region thereof) is selected from the group consisting of SEQ ID NOs: 110, 111, 112, 113, 114, 115, 116, 117, 118, 119, 120, 121, 122, 123, 124, 125, 126, 127, 28, 129, 130, 131, 132, 133, 134, 135 and 136, or is selected from the group consisting of at least 10 contiguous monomers thereof. In other embodiments, the sequence of the oligomer of the invention (or of a first region thereof) comprises one, two, or three base moieties that differ from those in oligomers having sequences of SEQ ID NOs: 110, 111, 112, 113, 114, 115, 116, 117, 118, 119, 120, 121, 122, 123, 124, 125, 126, 127, 128, 129, 130, 131, 132, 133, 134, 135 or 136, or the sequences of at least 10 contiguous monomers thereof, when optimally aligned with the selected sequence or region thereof.

In various embodiments, the sequence of the oligomer (or region thereof) is selected from the group consisting of SEQ ID NOs: 149, 150, 151, 152, 153, 154, 155, 156, 157, 158, 159 and 160 or is selected from the group consisting of at least 10 contiguous monomers of SEQ ID NOs: 149, 150, 151, 152, 153, 154, 155, 156, 157, 158, 159 and 160. In other embodiments, the sequence of the oligomer (or of a first region thereof) comprises one, two, or three base moieties that differ from those in oligomers having sequences of SEQ ID NOs: 149, 150, 151, 152, 153, 154, 155, 156, 157, 158, 159 or 160, or the sequences of at least 10 contiguous monomers thereof, when optimally aligned with the selected sequence or region thereof.

In various embodiments the sequence of the oligomer (or region thereof) is selected from the group consisting of SEQ ID NOs: 111, 112, 114, 115, 116, 118, 119, 122, 131, 132 and 136, or the sequence is selected from the group consisting of at least 10 contiguous monomers of SEQ ID NOs: 111, 112, 114, 115, 116, 118, 119, 122, 131, 132 and 136, such as the sequence of 11, 12, 13, 14, 15 or 16 contiguous monomers thereof. In other embodiments, the sequence of the oligomer (or of a region thereof) comprises one, two, or three base moieties that differ from those in oligomers having sequences of SEQ ID NOs: 111, 112, 114, 115, 116, 118, 119, 122, 131, 132 or 136, or the sequences of at least 10 contiguous monomers thereof, when optimally aligned with the selected sequence or region thereof.

In various embodiments, the sequence of the oligomer (or region thereof) is selected from the group consisting of SEQ ID NOs: 149, 150, 153, 154, 157, and 158, or the sequence is selected from the group consisting of at least 10 contiguous monomers of SEQ ID NOs: 149, 150, 153, 154, 157, and 158, such as the sequence of 11, 12, 13, 14, 15 or 16 contiguous monomers thereof. In other embodiments, the sequence of the oligomer of the invention (or of a region thereof) comprises one, two, or three base moieties that differ from those in oligomers having sequences of SEQ ID NOs: 149, 150, 153, 154, 157, or 158, or the sequences of at least 10 contiguous monomers thereof, when optimally aligned with the selected sequence or region thereof.

In various embodiments, the sequence of the oligomer (or region thereof) is selected from the group consisting of SEQ ID NOs: 3, 4, 6, 7, 8, 10, 11, 14, 23, 24 and 28, or the sequence is selected from the group of at least 10 contiguous monomers of SEQ ID NOs: 3, 4, 6, 7, 8, 10, 11, 14, 23, 24 and 28, such as the sequence of 11, 12, 13, 14, 15 or 16 contiguous monomers thereof. In other embodiments, the sequence of the oligomer (or of a region thereof) comprises one, two, or three base moieties that differ from those in oligomers having sequences of SEQ ID NOs: 3, 4, 6, 7, 8, 10, 11, 14, 23, 24 or 28, or the sequences of at least 10 contiguous monomers thereof, when optimally aligned with the selected sequence or region thereof.

In various embodiments, the sequence of the oligomer (or region thereof) is selected from the group consisting of SEQ ID NOs: 151, 152, 155, 156, 159 and 160; or the sequence is selected from the group of at least 10 contiguous monomers of SEQ ID NOs: 151, 152, 155, 156, 159 and 160, such as the sequence of 11, 12, 13, 14, 15 or 16 monomers thereof. In other embodiments, the sequence of the oligomer (or of a region thereof) comprises one, two, or three base moieties that differ from those in oligomers having sequences of SEQ ID NOs: 151, 152, 155, 156, 159 and 160, or the sequences of at least 10 contiguous monomers thereof, when optimally aligned with the selected sequence or region thereof.

In various embodiments, the sequence of the oligomer (or region thereof) is selected from the group consisting of SEQ ID NO: 57, 60, 64, 67, 70, 74, 77, 82, 87, 90 and 96, or the sequence is selected from the group of at least 10 contiguous monomers of SEQ ID NO: 57, 60, 64, 67, 70, 74, 77, 82, 87, 90 and 96, such as the sequence of 11, 12, 13, 14, 15 or 16 contiguous monomers thereof. In other embodiments, the sequence of the oligomer (or of a region thereof) comprises one, two, or three base moieties that differ from those in oligomers having sequences of SEQ ID NO: 57, 60, 64, 67, 70, 74, 77, 82, 87, 90 and 96, or the sequences of at least 10 contiguous monomers thereof, when optimally aligned with the selected sequence or region thereof.

In various embodiments, the sequence of the oligomer (or region thereof) is selected from the group consisting of SEQ ID NO: 87, 90 and 96, or the sequence is selected from the group consisting of at least 10 contiguous monomers of SEQ ID NO: 87, 90 and 96, such as the sequence of 11, 12, 13, 14, 15 or 16 contiguous monomers thereof. In other embodiments, the sequence of the oligomer (or of a region thereof) comprises one, two, or three base moieties that differ from those in oligomers having sequences of SEQ ID NO: 87, 90 and 96, or the sequences of at least 10 contiguous monomers thereof, when optimally aligned with the selected sequence or region thereof.

In various embodiments, the sequence of the oligomer (or region thereof) is selected from the group consisting of SEQ ID NO: 99, 100, 101, 102, 103, and 104, or the sequence is selected from the group consisting of at least 10 contiguous monomers of SEQ ID NO: 99, 100, 101, 102, 103, and 104, such as the sequence of 11, 12, 13, 14, 15 or 16 contiguous monomers thereof. In various embodiments, the sequence of the oligomer of the invention (or of a first region thereof) comprises one, two, or three base moieties that differ from those in oligomers having sequences of SEQ ID NO: 99, 100, 101, 102, 103, and 104, or the sequences of at least 10 contiguous monomers thereof, when optimally aligned with the selected sequence or region thereof.

In certain embodiments, the sequence of the oligomer (or region thereof) is selected from the group consisting of SEQ ID NO: 99, 100 and 104, or the sequence is selected from the group consisting of at least 10 contiguous monomers of SEQ ID NO: 99, 100 and 104. In various embodiments, the sequence of the oligomer of the invention (or of a first region thereof) comprises one, two, or three base moieties that differ from those in oligomers having sequences of SEQ ID NO: 99, 100 and 104, or the sequences of at least 10 contiguous monomers thereof, when optimally aligned with the selected sequence or region thereof.

In certain embodiments, the monomer region consists of 11, 12, 13, 14, 15, 16, 17, 18, 19, 20, 21, 22, 23, 24, 25, 26, 27, 28, or 29 contiguous monomers, such as 12-22, such as 12-18 monomers. Suitably, in some embodiments, the region is of the same length as the oligomer of the invention.

In various embodiments, the oligomer comprises additional monomers at the 5' or 3' ends, such as, independently, 1, 2, 3, 4 or 5 additional monomers at the 5' and/or 3' ends of the oligomer, which are non-complementary to the target region. In various embodiments, the oligomer of the invention comprises a region which is complementary to the target which is flanked 5' and/or 3' by additional monomers. In some embodiments, the additional monomers at the 5' and/or 3' ends are DNA or RNA monomers. In some embodiments, the additional monomers at the 5' and/or 3' ends may represent region D as referred to in the context of gapmer oligomers herein.

In various embodiments, the oligomer according to the invention consists of or comprises contiguous monomers having a base sequence according to SEQ ID NO: 2, such as SEQ ID NO 56, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 3, such as SEQ ID NOs: 57, 58 or 59, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 4, such as SEQ ID NOs: 60, 61 and 62, or according to a region of at least 10 contiguous monomers thereof, such as 11, 12, 13, 14, 15 or 16 contiguous monomers thereof.

In various embodiments the oligomer according to the invention consists of or comprises contiguous monomers having a base sequence according to SEQ ID NO: 5, such as SEQ ID NO: 63, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 6, such as SEQ ID NO 64, 65 and 66, or according to a region of at least 10 contiguous monomers thereof, such as 11, 12, 13, 14, 15 or 16 contiguous monomers thereof.

In various embodiments, the oligomer according to the invention consists of or comprises contiguous monomers having a sequence according to SEQ ID NO: 7, such as SEQ ID NOs: 67, 68 or 69, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 8, such as SEQ ID NOs: 70, 71 or 72, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 9, such as SEQ ID NO: 73, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 10, such as SEQ ID NOs: 74, 75 or 76, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 11, such as SEQ ID NOs: 77, 78 or 79, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 12, such as SEQ ID NO: 80, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 13, such as SEQ ID NO: 81, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 14, such as SEQ ID NOs: 82, 83, or 84, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 15, such as SEQ ID NO: 85, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 16, such as SEQ ID NO: 86, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 17, such as SEQ ID NOs: 87, 88 or 89, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 18, such as SEQ ID NOs: 90, 91 or 92, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 19, such as SEQ ID NO: 93, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 20, such as SEQ ID NO: 94, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 21, such as SEQ ID NO: 95, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 22, such as SEQ ID NOs: 96, 97 or 98, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 23, such as SEQ ID NOs: 99, 137 or 138, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 24, such as SEQ ID NOs: 100, 139 or 140, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 25, such as SEQ ID NOs: 101, 141 or 142, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 26, such as SEQ ID NOs: 102, 143 or 144, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 27, such as SEQ ID NOs: 103, 145 or 146, or according to a region of at least 10 contiguous monomers thereof, such as 11, 12, 13, 14, 15 or 16 contiguous monomers thereof.

In various embodiments, the oligomer according to the invention consists of or comprises contiguous monomers having a base sequence according to SEQ ID NO: 28, such as SEQ ID NOs: 104, 147 or 148 or according to a region of at least 10 contiguous monomers thereof, such as 11, 12, 13, 14, 15 or 16 contiguous monomers thereof.

In certain embodiments, the oligomer according to the invention consists of or comprises contiguous monomers having a base sequence selected from the group consisting of SEQ ID NOs: 149, 150, 151, 152, 153, 154, 155, 156, 157, 158, 159 and 160, as shown below in Table 1, or according to a region of at least 10 contiguous monomers thereof, such as 11, 12, 13, 14, 15 or 16 contiguous monomers thereof.

TABLE 1

Oligomers Targeted to Variant PIK3CA Nucleic Acids

| SEQ ID NO: 149* | GCTCAGTGATTTXAGAGAGAGGAT |
|---|---|
| SEQ ID NO: 150* | TTTCTCCTGCTXAGTGATTTCAGA |
| SEQ ID NO: 151* | GATTTXAGAGAGAGGA |
| SEQ ID NO: 152* | AGTGATTTXAGAGAGA |
| SEQ ID NO: 153* | ATCTTTCTCCTGCTXAGTGATTTC |
| SEQ ID NO: 154* | CAGTGATTTXAGAGAGAGGATCTC |
| SEQ ID NO: 155* | TCCTGCTXAGTGATTT |
| SEQ ID NO: 156* | TTCTCCTGCTXAGTGA |
| SEQ ID NO: 157† | AGCCACCATGAXGTGCATCATTCA |
| SEQ ID NO: 158† | TCCAGCCACCATGAXGTGCATCAT |
| SEQ ID NO: 159† | GCCACCATGAXGTGCA |
| SEQ ID NO: 160† | ACCATGAXGTGCATCA |

*Where X is not C (i.e., X is A, G or T, preferably T).
†Where X is not T (i.e., X is A, G or C, preferably C).

In some embodiments, the oligomer according to the invention consists of or comprises monomers having a nucleobase sequence selected from the following (5'-3'):

(G)(A)(T)TTXAG(A)(G)(A)(G) (SEQ ID NO: 161), wherein the monomers in parentheses are optionally present, and wherein X is not C (i.e., X is A, G or T, preferably T), for example, as shown in SEQ ID NOs: 149-152;

(C)(T)(G)CTXAG(T)(G)(G) (SEQ ID NO: 162), wherein the monomers in parentheses are optionally present, and wherein X is not C (i.e., X is A, G or T, preferably T), for example, as shown in SEQ ID NOs: 153-156; and (C)(A)(T)GAXGT(G)(C)(A) (SEQ ID NO: 163), wherein the monomers in parentheses are optionally present, and wherein X is not T (i.e., X is A, G or C, preferably C), for example, as shown in SEQ ID NOs: 157-160.

In certain embodiments, X is in region B (of a gapmer or shortmer), and is, e.g., a DNA monomer. Suitably, X is positioned at the center of region B. In various embodiments, X is in region B and is flanked on the 5' end by at least 1, 2, 3 or 4 additional monomers of region B and/or is independently flanked on the 3' end by at least 1, 2, 3 or 4 additional monomers of region B. In some embodiments, X is not within regions A, C or, where present, D. In other embodiments, X is within region B, but is not immediately adjacent to the monomers of regions A or C.

In certain embodiments, the oligomer or region thereof, comprises one or more base mismatches when compared to the sequence of the best-aligned target region of a nucleic acid which encodes the PIK3CA polypeptide.

In various embodiments, the oligomer of the invention does not comprise more than four, such as not more than three, such as not more than two, such as not more than one base mismatch, when compared to the sequence of the best-aligned target region of a nucleic acid which encodes the PIK3CA polypeptide, such as the target nucleic acid having the sequence of SEQ ID NO: 1, or naturally occurring variants thereof. In certain embodiments, naturally occurring variants are allelic variants and spontaneous variants, such as nucleic acids which code for one or more of the following amino acid mutations: E524K, E545K, or H1047R., such as nucleic acids which code for one of the following amino acid mutations: G1781A, G1790A or A3297G (the amino acid residue in front of the position refers to the wild-type amino acid, the letter after the position refers to the amino acid residue in a PIK3CA mutant).

In certain embodiments, the invention provides a method for the preparation of an oligomer for the down-regulation of a target mRNA associated with cancer cells, such as a PIK3CA mRNA target, the method comprising the steps of:

(a) identifying a single point mutation present in the target region of a target mRNA associated with cancer, wherein the single point mutation is present in cancer cells but is absent in non-cancer cells; and (b) preparing an oligomer which comprises a region of contiguous monomers having a base sequence that is identical to the base sequence of the reverse complement of the target region of the target mRNA.

Suitably, the single point mutation is associated with cancer, such as the PIK3CA point mutations referred to herein.

Suitably, the oligomer is a gapmer or shortmer oligonucleotide as described herein (although not limited necessarily to the oligomers targeting PIK3CA). As referred to herein, in one embodiment, the monomer of the oligomer comprising the nucleobase that is complementary to the single point mutation in the mRNA target region is in region B.

In certain embodiments, the oligomers of the invention a target region of the mRNA target nucleic acid which comprises a point mutation associated with a cancer phenotype. In these embodiments, the oligomers of the invention suitably have a lower binding affinity to a target region of a target mRNA having a wild-type sequence, such as a PIK3CA mRNA found in non-cancerous cells, thereby selectively down-regulating (e.g., by inhibiting) the variant target nucleic acid in cancerous cells and having less effect on the wild-type target nucleic acid in non-cancerous cells.

Nucleosides and Nucleoside Analogues

In various embodiments, at least one of the monomers present in the oligomer is a nucleoside analogue that contains a modified base, such as a base selected from 5-methylcytosine, isocytosine, pseudoisocytosine, 5-bromouracil, 5-propynyluracil, 6-aminopurine, 2-aminopurine, inosine, diaminopurine, 2-chloro-6-aminopurine, xanthine and hypoxanthine.

In various embodiments, at least one of the monomers present in the oligomer is a nucleoside analogue that contains a modified sugar.

In some embodiments, the linkage between at least 2 contiguous monomers of the oligomer is other than a phosphodiester linkage.

In certain embodiments, the oligomer includes at least one monomer that has a modified base, at least one monomer (which may be the same monomer) that has a modified sugar and at least one inter-monomer linkage that is non-naturally occurring.

Specific examples of nucleoside analogues are described by e.g. Freier & Altmann; *Nucl. Acid Res.,* 1997, 25, 4429-4443 and Uhlmann; *Curr. Opinion in Drug Development,* 2000, 3(2), 293-213, and in Scheme 1 (in which some nucleoside analogues are shown as nucleotides):

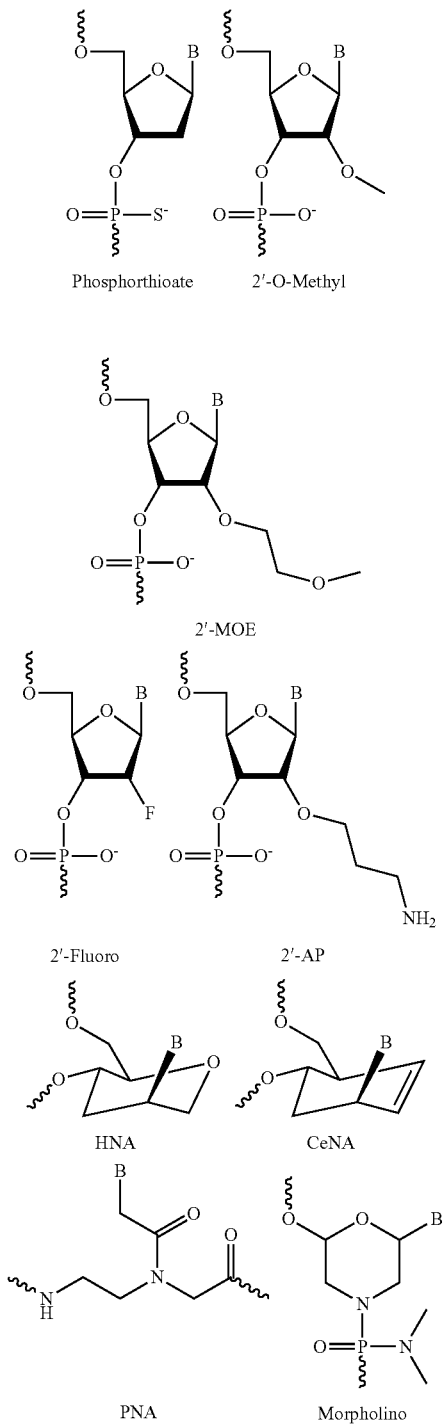

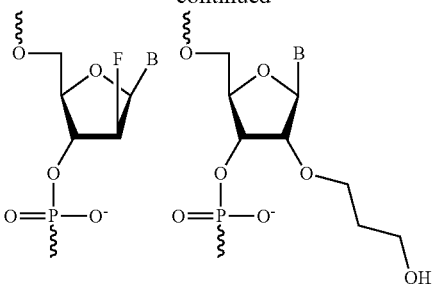

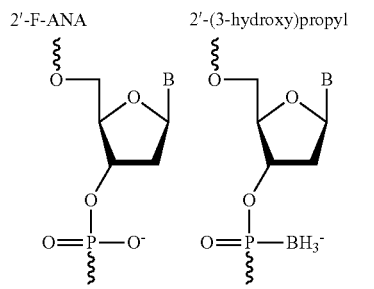

The oligomer may thus comprise or consist of a simple sequence of natural occurring nucleosides—preferably 2DNA monomers, but also possibly RNA monomers, or a combination of nucleosides and one or more nucleoside analogues. In some embodiments, the nucleoside analogues enhance the affinity of the oligomer for the target region of the target nucleic acid.

Examples of suitable and preferred nucleoside analogues are provided by PCT/DK2006/000512, incorporated herein by reference in its entirety, or are referenced therein.

In some embodiments, the nucleoside analogue comprises a sugar moiety modified to provide a 2'-substituent group, such as 2'-O-alkyl-ribose sugars, 2'-amino-deoxyribose sugars, and 2'-fluoro-deoxyribose sugars.

In some embodiments, the nucleoside analogue comprises a sugar in which a bridged structure, creating a bicyclic sugar (LNA), which enhances binding affinity and may also provide some increased nuclease resistance. In various embodiments, the LNA monomer is selected from oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). In certain embodiments, the LNA monomers are beta-D-oxy-LNA. LNA monomers are further described below.

In various embodiments, incorporation of affinity-enhancing nucleoside analogues in the oligomer, such as LNA monomers or monomers containing 2'-substituted sugars, or incorporation of modified linkage groups provides increased nuclease resistance. In various embodiments, incorporation of affinity-enhancing nucleoside analogues allows the size of the oligomer to be reduced, and also reduces the size of the oligomer that binds specifically to a target region of a target sequence.

In some embodiments, the oligomer comprises at least 2 nucleoside analogues. In some embodiments, the oligomer comprises from 3-8 nucleoside analogues, e.g. 6 or 7 nucleoside analogues. In various embodiments, at least one of the nucleoside analogues is a locked nucleic acid (LNA) monomer; for example at least 3 or at least 4, or at least 5, or at least 6, or at least 7, or 8, nucleoside analogues are LNA monomers. In some embodiments, all the nucleoside analogues are LNA monomers.

It will be recognised that when referring to a preferred oligomer base sequence, in certain embodiments, the oligomers comprise a corresponding nucleoside analogue, such as a corresponding LNA monomer or other corresponding nucleoside analogue, which raise the duplex stability ($T_m$) of the oligomer/target region duplex (i.e. affinity enhancing nucleoside analogues).

In various embodiments, any mismatches (i.e., non-complementarities) between the base sequence of the oligomer and the base sequence of the target region, if present, are preferably located other than in the regions of the oligomer that contain affinity-enhancing nucleoside analogues (e.g., regions A or C), such as within region B as referred to herein, and/or within region D as referred to herein, and/or in regions consisting of DNA monomers, and/or in regions which are 5' or 3' to the region of the oligomer that is complementary to the target region.

In some embodiments the nucleoside analogues present within the oligomer of the invention (such as in regions A and C mentioned herein) are independently selected from, for example: monomers containing 2'-O-alkyl-ribose sugars, monomers containing 2'-amino-deoxyribose sugars, monomers containing 2'-fluoro-deoxyribose sugars, LNA monomers, monomers containing arabinose sugars ("ANA monomers"), monomers containing 2'-fluoro-arabinose sugars, monomers containing d-arabino-hexitol sugars ("HNA monomers"), intercalating monomers as defined in Christensen (2002) Nucl. Acids. Res. 30: 4918-4925, hereby incorporated by reference, and 2'-O-methoxyethyl-ribose (2'MOE) sugars. In some embodiments, there is only one of the above types of nucleoside analogues present in the oligomer of the invention, or region thereof.

In certain embodiments, the nucleoside analogues contain 2'MOE sugars, 2'-fluoro-deoxyribose sugars, or LNA sugars, and as such the oligonucleotide of the invention may comprise nucleoside analogues which are independently selected from these three types. In certain oligomer embodiments containing nucleoside analogues, at least one of said nucleoside analogues contains a 2'-MOE-ribose sugar, such as 2, 3, 4, 5, 6, 7, 8, 9 or 10 nucleoside analogues containing 2'-MOE-ribose sugars. In some embodiments, at least one nucleoside analogue contains a 2'-fluoro-deoxyribose sugar, such as 2, 3, 4, 5, 6, 7, 8, 9 or 10 nucleoside analogues containing 2'-fluoro-DNA nucleoside sugars.

In various embodiments, the oligomer according to the invention comprises at least one Locked Nucleic Acid (LNA) monomer, such as 1, 2, 3, 4, 5, 6, 7, or 8 LNA monomers, such as 3-7 or 4 to 8 LNA monomers, or 3, 4, 5, 6 or 7 LNA monomers. In various embodiments, all the nucleoside analogues are LNA monomers. In certain embodiments, the oligomer comprises both beta-D-oxy-LNA monomers, and one or more of the following LNA monomers: thio-LNA monomers, amino-LNA monomers, oxy-LNA monomers, and/or ENA monomers in either the beta-D or alpha-L configurations, or combinations thereof. In certain embodiments, the cytosine base moieties of all LNA monomers in the oligomer are 5-methylcytosines. In certain embodiments of the invention, the oligomer comprises both LNA and DNA monomers. Typically, the combined total of LNA and DNA monomers is 10-25, preferably 10-20, even more preferably 12-16. In some embodiments of the invention, the oligomer or region thereof consists of at least one LNA monomer, and the remaining monomers are DNA monomers. In certain embodiments, the oligomer comprises only LNA monomers and nucleosides (such as RNA or DNA monomers, most preferably DNA monomers) optionally with modified linkage groups such as phosphorothioate.

In various embodiments, at least one of the nucleoside analogues present in the oligomer has a modified base selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

LNA

The term "LNA monomer" refers to a nucleoside analogue containing a bicyclic sugar (an "LNA sugar"). The terms "LNA oligonucleotide" and "LNA oligomer" refer to an oligomer containing one or more LNA monomers.

The LNA used in the oligonucleotide compounds of the invention preferably has the structure of the general formula I

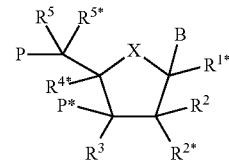

wherein X is selected from -0-, —S—, —N($R^{N*}$)—, —C($R^6R^{6*}$)—;

B is selected from hydrogen, optionally substituted $C_{1-4}$-alkoxy, optionally substituted $C_{1-4}$-alkyl, optionally substituted $C_{1-4}$-acyloxy, nucleobases, DNA intercalators, photochemically active groups, thermochemically active groups, chelating groups, reporter groups, and ligands;

P designates the radical position for an internucleoside linkage to a succeeding monomer, or a 5'-terminal group, such internucleoside linkage or 5'-terminal group optionally including the substituent $R^5$ or equally applicable the substituent $R^{5*}$;

P* designates an internucleoside linkage to a preceding monomer, or a 3'-terminal group;

$R^{4*}$ and $R^{2*}$ together designate a biradical consisting of 1-4 groups/atoms selected from —C($R^aR^b$)—, —C($R^a$)=C($R^b$)—, —C($R^a$)=N—, —O—, —Si($R^a$)$_2$—, —S—, —SO$_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, Sulphanyl, $C_{1-6}$-alkylthio, halogen, DNA intercalators, photochemically active groups, thermochemically active groups, chelating groups, reporter groups, and ligands, where aryl and heteroaryl are optionally substituted and where two geminal substituents $R^a$ and $R^b$ together may designate optionally substituted methylene (=CH$_2$), and each of the substituents $R^{1*}$, $R^2$, $R^3$, $R^5$, $R^{5*}$, $R^6$ and $R^{6*}$, which are present is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{2-12}$-alkoxycarbonyl, $C_{1-12}$-alkylcarbonyl, formyl, aryl, aryloxy-carbonyl, aryloxy, arylcarbonyl, heteroaryl, hetero-aryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1-5 carbon atom(s) alkylene chain which is optionally interrupted and/or terminated by one or more heteroatoms/groups selected from —O—, —S—, and —(NR$^N$)— where R$^N$ is selected from hydrogen and $C_{1-4}$-alkyl, and where two adjacent (non-geminal) substituents may designate an additional bond resulting in a double bond; and R$^{N*}$, when present and not involved in a biradical, is selected from hydrogen and $C_{1-4}$-alkyl; and basic salts and acid addition salts thereof;

In some embodiments R$^{s*}$ is selected from H, —CH$_3$, —CH$_2$—CH$_3$, —CH$_2$—O—CH$_3$, and —CH=CH$_2$.

In various embodiments, R$^{4*}$ and R$^{2*}$ together designate a biradical selected from —C(R$^a$R$^b$)—O—, —C(R$^a$R$^b$)—C(R$^c$R$^d$)—O—, —C(R$^a$R$^b$)—C(R$^c$R$^d$)—C(R$^e$R$^f$)—O—, —C(R$^a$R$^b$)—O—C(R$^c$R$^d$)—, —C(R$^a$R$^b$)—O—C(R$^c$R$^d$)—O—, —C(R$^a$R$^b$)—C(R$^c$R$^d$)—, —C(R$^a$R$^b$)—C(R$^c$R$^d$)—C(R$^e$R$^f$)—, —C(R$^a$)=C(R$^b$—C(R$^c$R$^d$)—, —C(R$^a$R$^b$)—N(R$^c$)—, —C(R$^a$R$^b$)—C(R$^c$R$^d$)—N(R$^e$)—, —C(R$^a$R$^b$—N(R$^c$)—O—, and —C(R$^a$R$^b$)—S—, —C(R$^a$R$^b$)—C(R$^c$R$^d$)—S—, wherein R$^a$, R$^b$, R$^c$, R$^d$, R$^e$, and R$^f$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkyl-sulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents R$^a$ and R$^b$ together may designate optionally substituted methylene (=CH$_2$), In a further embodiment R$^4$ and R$^2$ together designate a biradical (bivalent group) selected from —CH$_2$—O—, —CH$_2$—S—, —CH$_2$—NH—, —CH$_2$—N(CH$_3$)—, —CH$_2$—CH$_2$—O—, —CH$_2$—CH(CH$_3$)—, —CH$_2$—CH$_2$—S—, —CH$_2$—CH$_2$—NH—, —CH$_2$—CH$_2$—CH$_2$—, —CH$_2$—CH$_2$—CH$_2$—O—, —CH$_2$—CH$_2$—CH(CH$_3$)—, —CH=CH—CH$_2$—, —CH$_2$—O—CH$_2$—O—, —CH$_2$—NH—O—, —CH$_2$—N(CH$_3$)—O—, —CH$_2$—O—CH$_2$—, —CH(CH$_3$)—O—, —CH(CH$_2$—O—CH$_3$)—O—.

For all chiral centers, asymmetric groups may be found in either R or S orientation.

Preferably, the LNA monomer used in the oligomer of the invention comprises at least one LNA monomer according to any of the formulas

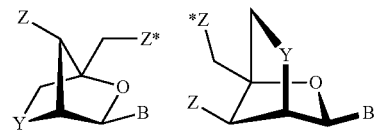

wherein Y is —O—, —O—CH$_2$—, —S—, —NH—, or N(R$^H$); Z and Z* are independently selected among an internucleoside linkage, a terminal group or a protecting group; B constitutes a natural or non-natural base moiety, and R$^H$ is selected from hydrogen and $C_{1-4}$-alkyl.

Specifically preferred LNA monomers are shown in Scheme 2:

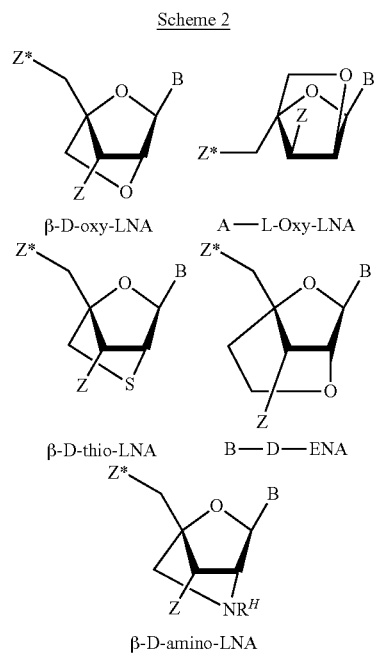

Scheme 2

β-D-oxy-LNA     A—L-Oxy-LNA

β-D-thio-LNA     B—D—ENA

β-D-amino-LNA

The term "thio-LNA"" refers to an LNA monomer in which Y in the general formula above is selected from S or —CH$_2$—S—. Thio-LNA can be in either the beta-D or the alpha-L-configuration.

The term "amino-LNA" refers to an LNA monomer in which Y in the general formula above is selected from —N(H)—, N(R)—, CH$_2$—N(H)—, and —CH$_2$—N(R)— where R is selected from hydrogen and $C_{1-4}$-alkyl Amino-LNA can be in either the beta-D or the alpha-L configuration.

The term "oxy-LNA" refers to an LNA monomer in which Y in the general formula above represents —O— or —CH$_2$—O—. Oxy-LNA can be in either the beta-D or the alpha L-configuration.

The term "ENA" refers to an LNA monomer in which Y in the general formula above is —CH$_2$—O— (where the oxygen atom of —CH$_2$—O— is attached to the 2'-position relative to the base B).

In a preferred embodiment the LNA monomer is selected from a beta-D-oxy-LNA monomer, an alpha-L-oxy-LNA monomer, a beta-D-amino-LNA monomer and beta-D-thio-LNA monomer, in particular a beta-D-oxy-LNA monomer.

In the present context, the term "$C_{1-4}$-alkyl" means a linear or branched saturated hydrocarbon chain wherein the chain has from one to four carbon atoms, such as methyl, ethyl, n-propyl, isopropyl, n-butyl, isobutyl, sec-butyl and tert-butyl.

RNAse H Recruitment

In some embodiments, the oligomer functions via non-RNase-mediated degradation of a target mRNA, such as by steric hindrance of translation, or other mechanisms; however, in various embodiments, the oligomers of the invention are capable of recruiting an endoribonuclease (RNase), such as RNase H.

Typically, the oligomer comprises of a region of at least 6, such as at least 7 contiguous monomers, such as at least 8 or at least 9 contiguous monomers, including 7, 8, 9, 10, 11, 12, 13, 14, 15 or 16 contiguous monomers, which, when forming a duplex with the target region of the target RNA. is capable of recruiting RNase. The region of the oligomer which is capable of recruiting RNAse may be region B, as referred to in the context of a gapmer as described herein. In some embodiments, the region of the oligomer which is capable of recruiting RNAse, such as region B, consists of 10, 11, 12, 13, 14, 15, 16, 17, 18, 19 or 20 monomers.

EP 1 222 309 provides in vitro methods for determining RNaseH activity, which may be used to determine the ability of the oligomers of the invention to recruit RNaseH. An oligomer is deemed capable of recruiting RNase H if, when contacted with the complementary region of the RNA target, it has an initial rate, as measured in pmol/l/min, of at least 1%, such as at least 5%, such as at least 10% or less than 20% of an oligonucleotide having the same base sequence but containing only DNA monomers, with no 2' substitutions, with phosphorothioate linkage groups between all monomers in the oligonucleotide, using the methodology provided in Examples 91-95 of EP 1 222 309, incorporated herein by reference.

In some embodiments, an oligomer is deemed essentially incapable of recruiting RNaseH if, when contacted with the target region of the RNA target, and RNaseH, the RNaseH initial rate, as measured in pmol/l/min, is less than 1%, such as less than 5%, such as less than 10% or less than 20% of the initial rate determined using an oligonucleotide having the same base sequence, but containing only DNA monomers, with no 2' substitutions, with phosphorothioate linkage groups between all monomers in the oligonucleotide, using the methodology provided in Examples 91-95 of EP 1 222 309.

In other embodiments, an oligomer is deemed capable of recruiting RNaseH if, when contacted with the target region of the RNA target, and RNaseH, the RNaseH initial rate, as measured in pmol/l/min, is at least 20%, such as at least 40%, such as at least 60%, such as at least 80% of the initial rate determined using an oligonucleotide having the same base sequence, but containing only DNA monomers, with no 2' substitutions, with phosphorothioate linkage groups between all monomers in the oligonucleotide, using the methodology provided in Examples 91-95 of EP 1 222 309.

Typically, the region of the oligomer which forms the duplex with the complementary target region of the target RNA and is capable of recruiting RNase contains DNA monomers and LNA monomers and forms a DNA/RNA-like duplex with the target region. The LNA monomers are preferably in the alpha-L configuration, particularly preferred being alpha-L-oxy LNA.

In various embodiments, the oligomer of the invention comprises both nucleosides and nucleoside analogues, and may be in the form of a gapmer, a headmer or a mixmer.

A "headmer" is defined as an oligomer that comprises a first region and a second region that is contiguous thereto, with the 5'-most monomer of the second region linked to the 3'-most monomer of the first region. The first region comprises a contiguous stretch of non-RNase-recruiting nucleoside analogues, and the second region comprises a contiguous stretch (such as at least 7 contiguous monomers) of DNA monomers or nucleoside analogue monomers recognizable and cleavable by the RNAse.

A "tailmer" is defined as an oligomer that comprises a first region and a second region that is contiguous thereto, with the 5'-most monomer of the second region linked to the 3'-most monomer of the first region. The first region comprises a contiguous stretch (such as at least 7 such monomers) of DNA monomers or nucleoside analogue monomers recognizable and cleavable by the RNase, and the second region comprises a contiguous stretch of non-RNase recruiting nucleoside analogue monomers.

Other "chimeric" oligomers, called "mixmers", consist of an alternating composition of (i) DNA monomers or nucleoside analogue monomers recognizable and cleavable by RNase, and (ii) non-RNase recruiting nucleoside analogue monomers.

In some embodiments, in addition to enhancing affinity of the oligomer for the target region, some nucleoside analogues also mediate RNase (e.g., RNase H) binding and cleavage. Since •-L-LNA monomers recruit RNase activity to a certain extent, in some embodiments, gap regions (e.g., region B as referred to herein below) of oligomers containing •-L-LNA monomers consist of fewer monomers recognizable and cleavable by the RNase, and more flexibility in the mixmer construction is introduced.

Conjugates

In the context of this disclosure, the term "conjugate" indicates a compound Formed by the covalent attachment ("conjugation") of an oligomer as described herein, to one or more moieties that are not themselves nucleic acids or monomers ("conjugated moieties"). Examples of such conjugated moieties include macromolecular compounds such as proteins, fatty acid chains, sugar residues, glycoproteins, polymers, or combinations thereof. Typically proteins may be antibodies for a target protein. Typical polymers may be polyethylene glycol.

Accordingly, provided herein are conjugates comprising an oligomer as herein described, and at least one conjugated moiety that is not a nucleic acid or monomer, covalently attached to said oligomer. Therefore, in certain embodiments where the oligomer of the invention consists of contiguous monomers having a specified sequence of bases, as herein disclosed, the conjugate may also comprise at least one conjugated moiety that is covalently attached to the oligomer.

In various embodiments of the invention, the oligomer is conjugated to a moiety that increases the cellular uptake of oligomeric compounds. WO2007/031091 provides suitable ligands and conjugates, which are hereby incorporated by reference.

In various embodiments, conjugation (to a conjugated moiety) may enhance the activity, cellular distribution or cellular uptake of the oligomer of the invention. Such moieties include, but are not limited to, antibodies, polypeptides, lipid moieties such as a cholesterol moiety, cholic acid, a thioether, e.g. Hexyl-s-tritylthiol, a thiocholesterol, an aliphatic chain, e.g., dodecandiol or undecyl residues, a phospholipids, e.g., di-hexadecyl-rac-glycerol or triethylammonium 1,2-di-o- hexadecyl-rac-glycero-3-h-phosphonate, a polyamine or a polyethylene glycol chain, an adamantane acetic acid, a palmityl moiety, an octadecylamine or hexylamino-carbonyl-oxycholesterol moiety.

In certain embodiments, the oligomers of the invention are conjugated to active drug substances, for example, aspirin, ibuprofen, a sulfa drug, an antidiabetic, an antibacterial or an antibiotic.

In certain embodiments the conjugated moiety is a sterol, such as cholesterol.

In various embodiments, the conjugated moiety comprises or consists of a positively charged polymer, such as a positively charged peptides of, for example 1-50, such as 2-20 such as 3-10 amino acid residues in length, and/or polyalkylene oxide such as polyethylene glycol (PEG) or polypropylene glycol—see WO 2008/034123, hereby incorporated by reference. Suitably the positively charged polymer, such as a polyalkylene oxide may be attached to the oligomer of the invention via a linker such as the releasable linker described in WO 2008/034123.

By way of example, the following moieties may be used in the conjugates of the invention:

gradable. See e.g., U.S. Pat. No. 7,087,229, which is incorporated by reference herein in its entirety.

In some embodiments, oligomers of the invention are functionalized at the 5' end in order to allow covalent attachment of the conjugated moiety to the 5' end of the oligomer. In other embodiments, oligomers of the invention can be functionalized at the 3' end. In still other embodiments, oligomers of the invention can be functionalized along the backbone or on the heterocyclic base moiety. In yet other embodiments, oligomers of the invention can be functionalized at more than one position independently selected from the 5' end, the 3' end, the backbone and the base.

In some embodiments, activated oligomers of the invention are synthesized by incorporating during the synthesis one or more monomers that is covalently attached to a functional moiety. In other embodiments, activated oligomers of the invention are synthesized with monomers that have not been functionalized, and the oligomer is functionalized upon completion of synthesis.

In some embodiments, the oligomers are functionalized with a hindered ester containing an aminoalkyl linker, wherein the alkyl portion has the formula $(CH_2)_w$, wherein w

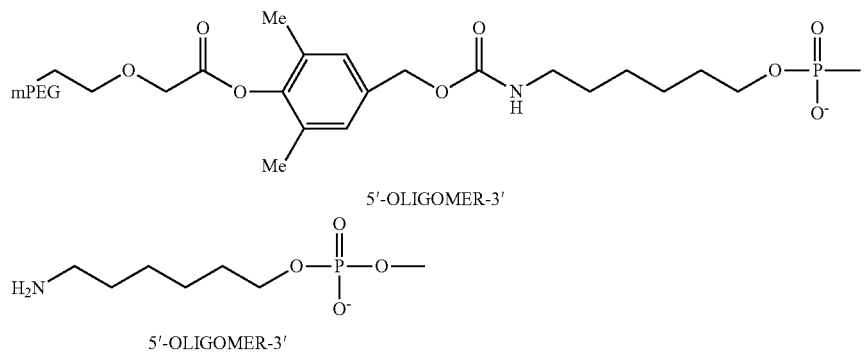

Activated Oligomers

The term "activated oligomer," as used herein, refers to an oligomer of the invention that is covalently linked (i.e., functionalized) to at least one functional moiety that permits covalent linkage of the oligomer to one or more conjugated moieties, i.e., moieties that are not themselves nucleic acids or monomers, to form the conjugates herein described. Typically, a functional moiety will comprise a chemical group that is capable of covalently bonding to the oligomer via, e.g., a 3'-hydroxyl group or the exocyclic $NH_2$ group of the adenine base, a spacer that is preferably hydrophilic and a terminal group that is capable of binding to a conjugated moiety (e.g., an amino, sulfhydryl or hydroxyl group). In some embodiments, this terminal group is not protected, e.g., is an $NH_2$ group. In other embodiments, the terminal group is protected, for example, by any suitable protecting group such as those described in "Protective Groups in Organic Synthesis" by Theodora W. Greene and Peter G. M. Wuts, 3rd edition (John Wiley & Sons, 1999). Examples of suitable hydroxyl protecting groups include esters such as acetate ester, aralkyl groups such as benzyl, diphenylmethyl, or triphenylmethyl, and tetrahydropyranyl. Examples of suitable amino protecting groups include benzyl, alpha-methylbenzyl, diphenylmethyl, triphenylmethyl, benzyloxycarbonyl, tert-butoxycarbonyl, and acyl groups such as trichloroacetyl or trifluoroacetyl.

In some embodiments, the functional moiety is self-cleaving. In other embodiments, the functional moiety is biodeis an integer ranging from 1 to 10, preferably about 6, wherein the alkyl portion of the alkylamino group can be straight chain or branched chain, and wherein the functional group is attached to the oligomer via an ester group (—O—C(O)—$(CH_2)_w$NH).

In other embodiments, the oligomers are functionalized with a hindered ester containing a $(CH_2\text{-}_w\text{-sulfhydryl (SH)})$ linker, wherein w is an integer ranging from 1 to 10, preferably about 6, wherein the alkyl portion of the alkylamino group can be straight chain or branched chain, and wherein the functional group attached to the oligomer via an ester group (—O—C(O)—$(CH_2)_w$SH). In some embodiments, sulfhydryl-activated oligonucleotides are conjugated with polymer moieties such as polyethylene glycol or peptides (via formation of a disulfide bond).

Activated oligomers containing hindered esters as described above can be synthesized by any method known in the art, and in particular, by methods disclosed in PCT Publication No. WO 2008/034122 and the examples therein, which is incorporated herein by reference in its entirety.

Activated oligomers covalently linked to at least one functional moiety can be synthesized by any method known in the art, and in particular, by methods disclosed in U.S. Patent Publication No. 2004/0235773, which is incorporated herein by reference in its entirety, and in Zhao et al. (2007) J. Controlled Release 119: 143-152; and Zhao et al. (2005) Bioconjugate Chem. 16:758-766.

In still other embodiments, the oligomers of the invention are functionalized by introducing sulfhydryl, amino or hydroxyl groups into the oligomer by means of a functionalizing reagent substantially as described in U.S. Pat. Nos. 4,962,029 and 4,914,210, i.e., a substantially linear reagent having a phosphoramidite at one end linked through a hydrophilic spacer chain to the opposing end which comprises a protected or unprotected sulfhydryl, amino or hydroxyl group. Such reagents primarily react with hydroxyl groups of the oligomer. In some embodiments, such activated oligomers have a functionalizing reagent coupled to a 5'-hydroxyl group of the oligomer. In other embodiments, the activated oligomers have a functionalizing reagent coupled to a 3'-hydroxyl group. In still other embodiments, the activated oligomers of the invention have a functionalizing reagent coupled to a hydroxyl group on the backbone of the oligomer. In yet further embodiments, the oligomer of the invention is functionalized with more than one of the functionalizing reagents as described in U.S. Pat. Nos. 4,962,029 and 4,914,210, incorporated herein by reference in their entirety. Methods of synthesizing such functionalizing reagents and incorporating them into monomers or oligomers are disclosed in U.S. Pat. Nos. 4,962,029 and 4,914,210.

In some embodiments, the 5'-terminus of a solid-phase bound oligomer is functionalized with a dienyl phosphoramidite derivative, followed by conjugation of the deprotected oligomer with, e.g., an amino acid or peptide via a Diels-Alder cycloaddition reaction.

In various embodiments, the incorporation of monomers containing 2'-sugar modifications, such as a 2'-carbamate substituted sugar or a 2'-(O-pentyl-N-phthalimido)-deoxyribose sugar into the oligomer facilitates covalent attachment of conjugated moieties to the sugars of the oligomer. In other embodiments, an oligomer with an amino-containing linker at the 2'-position of one or more monomers is prepared using a reagent such as, for example, 5'-dimethoxytrityl-2'-O-(e-phthalimidylaminopentyl)-2'-deoxyadenosine-3'-N,N-diisopropyl-cyanoethoxy phosphoramidite. See, e.g., Manoharan, et al., Tetrahedron Letters, 1991, 34, 7171.

In still further embodiments, the oligomers of the invention have amine-containing functional moieties on the nucleobase, including on the N6 purine amino groups, on the exocyclic N2 of guanine, or on the N4 or 5 positions of cytosine. In various embodiments, such functionalization may be achieved by using a commercial reagent that is already functionalized in the oligomer synthesis.

Some functional moieties are commercially available, for example, heterobifunctional and homobifunctional linking moieties are available from the Pierce Co. (Rockford, Ill.). Other commercially available linking groups are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, and 3'-Amino-Modifier is also available from Clontech Laboratories Inc. (Palo Alto, Calif.).

Compositions

In various embodiments, the oligomer of the invention, or a conjugate thereof, is used in pharmaceutical formulations and compositions. Suitably, such compositions comprise a pharmaceutically acceptable diluent, carrier, salt or adjuvant.

Suitable dosages, formulations, administration routes, compositions, dosage forms, combinations with other therapeutic agents, pro-drug formulations are also provided in PCT/DK2006/000512—which are hereby incorporated by reference. Details on techniques for formulation and administration also may be found in the latest edition of "REMINGTON'S PHARMACEUTICAL SCIENCES" (Maack Publishing Co, Easton Pa.).

In some embodiments, an oligomer of the invention is covalently linked to a conjugated moiety to aid in delivery of the oligomer across cell membranes. An example of a conjugated moiety that aids in delivery of the oligomer across cell membranes is a lipophilic moiety, such as cholesterol. In various embodiments, an oligomer of the invention is formulated with lipid formulations that form liposomes, such as Lipofectamine 2000 or Lipofectamine RNAiMAX, both of which are commercially available from Invitrogen. In some embodiments, the oligomers of the invention are formulated with a mixture of one or more lipid-like non-naturally occurring small molecules ("lipidoids"). Libraries of lipidoids can be synthesized by conventional synthetic chemistry methods and various amounts and combinations of lipidoids can be assayed in order to develop a vehicle for effective delivery of an oligomer of a particular size to the targeted tissue by the chosen route of administration. Suitable lipidoid libraries and compositions can be found, for example in Akinc et al., Nature Biotechnol., 26, 561-569 (2008), which is incorporated by reference herein.

As used herein, the term "pharmaceutically acceptable salts" refers to salts that retain the desired biological activity of the herein identified compounds and exhibit acceptable levels of undesired toxic effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N'-dibenzylethylenediamine, D-glucosamine, tetraethylammonium, or ethylenediamine; or (c) combinations of (a) and (b); e.g., a zinc tannate salt or the like.

Applications

The term "treatment" as used herein refers to both treatment of an existing disease (e.g., a disease or disorder as referred to herein below), or prevention of a disease, i.e., prophylaxis. It will therefore be recognised that, in certain embodiments, "treatment" includes prophylaxis.

In various embodiments, the oligomers of the invention may be utilized as research reagents for, for example, diagnostics, therapeutics and prophylaxis.

In some embodiments, such oligomers may be used for research purposes to specifically inhibit the expression of PIK3CA protein (typically, by degrading or inhibiting the PIK3CA mRNA and thereby preventing protein formation) in cells and experimental animals, thereby facilitating functional analysis of the target or an appraisal of its usefulness as a target for therapeutic intervention.

In certain embodiments, the oligomers may be used in diagnostics to detect and quantitate PIK3CA expression in cells and tissues by northern blotting, in-situ hybridisation or similar techniques.

In various therapeutic embodiments, a non-human animal or a human, suspected of having a disease or disorder, which can be treated by modulating the expression of PIK3CA is treated by administering an effective amount of an oligomer (or conjugate thereof) in accordance with this invention. Further provided are methods of treating a mammal, such as treating a human, suspected of having or being prone to a disease or condition, associated with expression of PIK3CA by administering a therapeutically or prophylactically effective amount of one or more of the oligomers or compositions of the invention.

In various therapeutic embodiments, a non-human animal or a human suspected of having a disease or disorder which can be treating by modulating the expression of PIK3CA and of beta-catenin is treated by administering an effective amount of an oligomer (or conjugate thereof) in accordance with this invention.

In various therapeutic embodiments, the non-human animal or human is treated with more than one oligomer of the invention (or conjugate), wherein one oligomer preferably binds to a PIK3CA target region and a second oligomer preferably binds to a beta-catenin target region.

In certain embodiments, the invention also provides for the use of the compounds or conjugates of the invention as described for the manufacture of a medicament for the treatment of a disorder as referred to herein, or for a method of the treatment of a disorder as referred to herein.

In various embodiments, the invention also provides for a method for treating a disorder as referred to herein said method comprising administering a compound according to the invention as herein described, and/or a conjugate according to the invention, and/or a pharmaceutical composition according to the invention to a patient in need thereof.

In various embodiments, the invention relates to an oligomer, a composition or a conjugate thereof as described herein for use as a medicament.

In various embodiments, the invention provides for a method for treating a disorder as referred to herein, the method comprising administering an effective amount of a compound according to the invention as herein described, and/or an effective amount of a conjugate according to the invention, and/or a pharmaceutical composition according to the invention to a patient in need thereof.

In various embodiments, the oligomer, or conjugate thereof, induces a desired therapeutic effect in humans through, for example, hydrogen bonding to a target nucleic acid. The oligomer causes a decrease (e.g., inhibition) in the expression of a target via hydrogen bonding (e.g., hybridisation) to the mRNA of the target thereby resulting in a reduction in gene expression.

It is highly preferred that the compounds of the invention are capable of hybridising to the target nucleic acid, such as PIK3CA mRNA, by Watson-Crick base pairing.

Medical Indications

In some embodiments, disorder to be treated is a hyperproliferative disorder, such as cancer, which is a solid tumor. In various embodiments, the cancer is a carcinoma. In certain embodiments, the cancer is a sarcoma. In yet further embodiments, the cancer is a glioma.

In certain embodiments, the carcinoma is selected from the group consisting of malignant melanoma, basal cell carcinoma, ovarian carcinoma, breast carcinoma, non-small cell lung cancer, renal cell carcinoma, bladder carcinoma, recurrent superficial bladder cancer, stomach carcinoma, prostatic carcinoma, pancreatic carcinoma, lung carcinoma, cervical carcinoma, cervical dysplasia, laryngeal papillomatosis, colon carcinoma, colorectal carcinoma and carcinoid tumors.

In various embodiments, the carcinoma is selected from the group consisting of malignant melanoma, non-small cell lung cancer, breast carcinoma, colon carcinoma and renal cell carcinoma. In still further embodiments, the carcinoma is a malignant melanoma selected from the group consisting of superficial spreading melanoma, nodular melanoma, lentigo malignant melanoma, acral melanoma, amelanotic melanoma and desmoplastic melanoma.

In various embodiments, the sarcoma is selected from the group consisting of osteosarcoma, Ewing's sarcoma, chondrosarcoma, malignant fibrous histiocytoma, fibrosarcoma and Kaposi's sarcoma.

In some embodiments the solid tumor is selected from the group consisting of glioblastoma, malignant melanoma, medulloblastoma, hepatocellular carcinoma, head and neck squamous cell carcinoma, gastric, ovarian, cervix and colorectal cancers, cancers of the breast, lung and colon, large B-cell lymphoma, anaplastic astrocytoma, anaplastic oligodendroglioma, prostate cancer, endometrial cancer, pancreatic cancer, bowel cancer, leukaemia, esophagus cancer, and thyroid cancer. In some embodiments, the solid tumor is liver or kidney cancer.

In various embodiments, the cancer is selected from the group consisting of Colorectal, glioblastoma, gastric, hepatocellular, breast, ovarian and lung cancer.

In various embodiments, the cancer is selected from the group consisting of; non-Hodgkin's lymphoma, Hodgkin's lymphoma, leukemia (e.g., acute leukemia such as acute lymphocytic leukemia, acute myelocytic leukemia, chronic myeloid leukemia, chronic lymphocytic leukemia, multiple myeloma), colon carcinoma, rectal carcinoma, pancreatic cancer, breast cancer, ovarian cancer, prostate cancer, renal cell carcinoma, hepatoma, bile duct carcinoma, choriocarcinoma, cervical cancer, testicular cancer, lung carcinoma, bladder carcinoma, melanoma, head and neck cancer, brain cancer, cancers of unknown primary site, neoplasms, cancers of the peripheral nervous system, cancers of the central nervous system, tumors (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, seminoma, embryonal carcinoma, Wilms' tumor, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, and retinoblastoma), heavy chain disease, metastases, and any disease or disorder characterized by uncontrolled or abnormal cell growth.

In some embodiments, the cancer is selected from the group consisting of Hodgkin's lymphoma, leukaemia, such as acute lymphocytic leukaemia, colon carcinoma, rectal carcinoma, brain cancer, neural blastomas, lung cancer, pancreatic cancer, melanoma, acute myelogenous leukaemia, liver cancer, thyroid cancer, kidney cancer, urinary tract cancer and bladder cancer.

In some embodiments, the cancer is selected from the group consisting of Hodgkin's lymphoma, leukaemia, such as acute lymphocytic leukaemia, colon carcinoma, brain cancer, and neural blastomas.

In various embodiments, the cancer is selected from the group consisting of lung, breast, colon, prostate, pancreas, lung, liver, thyroid, kidney, brain, testes, stomach, intestine, bowel, spinal cord, sinuses, bladder, urinary tract and ovarian cancer.

In certain embodiments, for example for the treatment of brain cancer, the oligomer or conjugate of the invention does not comprise phosphorothioate linkages between adjacent monomers.

In certain embodiments, the disease or disorder is associated with a mutation in the PIK3CA gene or a gene whose protein product is associated with or interacts with PIK3CA. Therefore, in various embodiments, the target mRNA is a mutated form of the PIK3CA sequence; for example, it comprises one or more single point mutations, such as SNPs associated with cancer.

In certain embodiments, the disease or disorder is associated with abnormal levels of a mutated form of PIK3CA. In certain embodiments, the disease or disorder is associated with abnormal levels of a wild-type form of PIK3CA. One aspect of the invention is directed to a method of treating a mammal suffering from or susceptible to conditions associated with abnormal levels of PIK3CA, comprising administering to the mammal a therapeutically effective amount of an oligomer of the invention targeted to PIK3CA or various conjugates thereof. In some embodiments, the oligomer comprises one or more LNA units. Another aspect of the invention is directed to a method of treating a mammal suffering from or susceptible to conditions associated with abnormal levels of PIK3CA, comprising administering to the mammal a therapeutically effective amount of an oligomer of the invention targeted to PIK3CA and to beta-catenin or various conjugates thereof.

Suitable dosages, formulations, administration routes, compositions, dosage forms, combinations with other therapeutic agents, prodrug formulations are also provided in WO 2007/031091, which is hereby incorporated by reference. The invention also provides for a pharmaceutical composition comprising a compound or a conjugate as herein described or a conjugate and a pharmaceutically acceptable diluent, carrier or adjuvant. WO 2007/031091 provides suitable and preferred pharmaceutically acceptable diluents, carriers and adjuvants, which are hereby incorporated by reference.

In various embodiments, the invention described herein encompasses a method of preventing or treating a disease comprising administering a therapeutically effective amount of an oligomer that modulates PIK3CA (and in some embodiments, beta-catenin) to a human in need of such therapy. The invention further encompasses the use of a short period of administration of an oligomer that modulates PIK3CA (and in some embodiments, beta-catenin) or conjugate thereof, rather than continuous administration.

Embodiments

The following embodiments of the present invention may be used in combination with the other embodiments described herein.

1. An oligomer of between 10-50 nucleobases in length which comprises a contiguous nucleobase sequence of a total of between 10-50 nucleobases, wherein said contiguous nucleobase sequence is at least 80% homologous to a corresponding region of a nucleic acid which encodes a mammalian PIK3CA kinase.

2. The oligomer according to embodiment 1, wherein said oligomer comprises at least one LNA unit.

3. The oligomer according to embodiment 1 or 2, wherein the contiguous nucleobase sequence comprises no more than 3, such as no more than 2 mismatches to the corresponding region of a nucleic acid which encodes a mammalian PIK3CA kinase.

4. The oligomer according to embodiment 3, wherein said contiguous nucleobase sequence comprises a single mismatch to the corresponding region of a nucleic acid which encodes a mammalian PIK3CA kinase, wherein, optionally, the single mismatch corresponds to a single nucleotide point mutation which is associated with a cancer phenotype.

5. The oligomer according to embodiment 1 or 2, wherein said contiguous nucleobase sequence comprises no mismatches, (i.e. is complementary to) the corresponding region of a nucleic acid which encodes a mammalian PIK3CA kinase.

6. The oligomer according to any one of embodiments 1-5, wherein the nucleobase sequence of the oligomer consists of the contiguous nucleobase sequence.

7. The oligomer according to any one of embodiments 1-6, wherein the nucleic acid which encodes a mammalian PIK3CA kinase is the human PIK3CA kinase nucleotide sequence such as SEQ ID No 1, or a variant thereof, such as SEQ ID NO 1 which comprises a single point mutation at a position selected from 1781, 1790 and 3297.

8. The oligomer according to any one of embodiments 1-7, wherein the contiguous nucleobase sequence is complementary to a corresponding region of both the human PIK3CA kinase nucleic acid sequence and a non-human mammalian PIK3CA kinase nucleic acid sequence, such as the mouse PIK3CA kinase nucleic acid sequence.

9. The oligomer according to any one of embodiments 1 to 8, wherein the contiguous nucleobase sequence comprises a contiguous subsequence of at least 7, nucleobase residues which, when formed in a duplex with the complementary PIK3CA kinase target RNA is capable of recruiting RNaseH.

10. The oligomer according to embodiment 9, wherein the contiguous nucleobase sequence comprises of a contiguous subsequence of at least 8, at least 9 or at least 10 nucleobase residues which, when formed in a duplex with the complementary PIK3CA kinase target RNA is capable of recruiting RNaseH.

11. The oligomer according to any one of embodiments 9 or 10 wherein said contiguous subsequence is at least 9 or at least 10 nucleobases in length, such as at least 12 nucleobases or at least 14 nucleobases in length, such as 14, 15 or 16 nucleobases residues which, when formed in a duplex with the complementary PIK3CA kinase target RNA is capable of recruiting RNaseH.

12. The oligomer according to embodiment any one of embodiments 1-11 wherein said oligomer is conjugated with one or more non-nucleobase compounds.

13. The oligomer according to any one of embodiments 1-12, wherein said oligomer has a length of between 10-22 nucleobases.

14. The oligomer according to any one of embodiments 1-13, wherein said oligomer has a length of between 12-18 nucleobases.

15. The oligomer according to any one of embodiments 1-14, wherein said oligomer has a length of 14, 15 or 16 nucleobases.

16. The oligomer according to any one of embodiments 1-15, wherein said continuous nucleobase sequence corresponds to a contiguous nucleotide sequence present in a nucleic acid sequence selected from the group consisting of SEQ ID NO 110-124, or 149-160.

17. The oligomer according to any one of embodiments 1-16, wherein the oligomer or contiguous nucleobase sequence comprises, or is selected from a corresponding nucleobase sequence present in a nucleotide sequence selected from the group consisting of SEQ ID NO 2-16.

18. The oligomer according to any one of embodiments 1-17, wherein said contiguous nucleobase sequence comprises at least one affinity enhancing nucleotide analogue.

19. The oligomer according to embodiment 18, wherein said contiguous nucleobase sequence comprises a total of 2, 3, 4, 5, 6, 7, 8, 9 or 10 affinity enhancing nucleotide analogues, such as between 5 and 8 affinity enhancing nucleotide analogues.

20. The oligomer according to any one of embodiments 1-19 which comprises at least one affinity enhancing nucleotide analogue, wherein the remaining nucleobases are selected from the group consisting of DNA nucleotides and RNA nucleotides, preferably DNA nucleotides.

21. The oligomer according to any one of embodiments 1-20, wherein the oligomer comprises of a sequence of nucleobases of formula, in 5' to 3' direction, A-B-C, and optionally of formula A-B-C-D, wherein:
  A consists or comprises of at least one nucleotide analogue, such as 1, 2, 3, 4, 5 or 6 nucleotide analogues, preferably between 2-5 nucleotide analogues, preferably 2, 3 or 4 nucleotide analogues, most preferably 2, 3 or 4 consecutive nucleotide analogues and;
  B consists or comprises at least five consecutive nucleobases which are capable of recruiting RNAseH (when formed in a duplex with a complementary RNA molecule, such as the PIK3CAK mRNA target), such as DNA nucleobases, such as 5, 6, 7, 8, 9, 10, 11 or 12 consecutive nucleobases which are capable of recruiting RNAseH, or between 6-10, or between 7-9, such as 8 consecutive nucleobases which are capable of recruiting RNAseH, and;
  C consists or comprises of at least one nucleotide analogue, such as 1, 2, 3, 4, 5, or 6 nucleotide analogues, preferably between 2-5 nucleotide analogues, such as 2, 3 or 4 nucleotide analogues, most preferably 2, 3 or 4 consecutive nucleotide analogues, and;
  D when present, consists or comprises, preferably consists, of one or more DNA nucleotide, such as between 1-3 or 1-2 DNA nucleotides.

22. The oligomer according to embodiment 21, wherein region A consists or comprises of 2, 3 or 4 consecutive nucleotide analogues.

23. The oligomer according to any one of embodiments 21-22, wherein region B consists or comprises of 7, 8, 9 or 10 consecutive DNA nucleotides or equivalent nucleobases which are capable of recruiting RNAseH when formed in a duplex with a complementary RNA, such as the PIK3CA kinase mRNA target.

24. The oligomer according to any one of embodiments 21-24, wherein region C consists or comprises of 2, 3 or 4 consecutive nucleotide analogues.

25. The oligomer according to any one of embodiments 21-24, wherein region D consists, where present, of one or two DNA nucleotides.

26. The oligomer according to any one of embodiments 21-25, wherein:
  A Consists or comprises of 3 contiguous nucleotide analogues;
  B Consists or comprises of 7, 8, 9 or 10 contiguous DNA nucleotides or equivalent nucleobases which are capable of recruiting RNAseH when formed in a duplex with a complementary RNA, such as the PIK3CA kinase mRNA target;
  A Consists or comprises of 3 contiguous nucleotide analogues;
  B Consists, where present, of one or two DNA nucleotides.

27. The oligomer according to embodiment 26, wherein the contiguous nucleobase sequence consists of 10, 11, 12, 13 or 14 nucleobases, and wherein;
  A. Consists of 1, 2 or 3 contiguous nucleotide analogues;
  B. Consists of 7, 8, or 9 consecutive DNA nucleotides or equivalent nucleobases which are capable of recruiting RNAseH when formed in a duplex with a complementary RNA, such as the PIK3CA kinase mRNA target;
  A Consists of 1, 2 or 3 contiguous nucleotide analogues;
  B Consists, where present, of one DNA nucleotide.

28. The oligomer according to any one of embodiments 21-27, wherein B comprises at least one LNA nucleobase which is in the alpha-L configuration, such as alpha-L-oxy LNA.

29. The oligomer according to any one of embodiments 1-28, wherein the nucleotide analogue(s) are independently or collectively selected from the group consisting of: Locked Nucleic Acid (LNA) units; 2'-O-alkyl-RNA units, 2'-OMe-RNA units, 2'-amino-DNA units, 2'-fluoro-DNA units, PNA units, HNA units, and INA units.

30. The oligomer according to embodiment 29 wherein all the nucleotide analogues(s) are LNA units.

31. The oligomer according to anyone of embodiments 1-30, which comprises 1, 2, 3, 4, 5, 6, 7, 8, 9 or 10 LNA units such as between 2 and 8 nucleotide LNA units.

32. The oligomer according to anyone of the embodiments 29-31, wherein the LNAs are independently selected from oxy-LNA, thio-LNA, and amino-LNA, in either of the beta-D and alpha-L configurations or combinations thereof.

33. The oligomer according to embodiment 32, wherein the LNAs are all beta-D-oxy-LNA.

34. The oligomer according to anyone of embodiments 21-33, wherein the nucleotide analogues of regions A and C are beta-D-oxy-LNA.

35. The oligomer according to anyone of embodiments 1-34, wherein at least one of the nucleobases present in the oligomers a modified nucleobase selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

36. The oligomer according to anyone of embodiments 1-35, wherein said oligomer hybridises with a corresponding mammalian PIK3CA kinase mRNA with a $T_m$ of at least 50° C.

37. The oligomer according to anyone of embodiments 1-36, wherein said oligomer hybridises with a corresponding mammalian PIK3CA kinase mRNA with a $T_m$ of no greater than 80° C.

38. The oligomer according to anyone of embodiments 1-37, wherein the internucleoside linkages are independently selected from the group consisting of: phosphodiester, phosphorothioate and boranophosphate.

39. The oligomer according to embodiment 38, wherein the oligomer comprises at least one phosphorothioate internucleoside linkage.

40. The oligomer according to embodiment 39, wherein the internucleoside linkages adjacent to and/or between DNA or RNA units, or within region B are phosphorothioate linkages.

41. The oligomer according to embodiment 39 or 40, wherein the linkages between at least one pair of consecutive nucleotide analogues is a phosphodiester linkage.

42. The oligomer according to embodiment 39 or 40, wherein all the linkages between consecutive nucleotide analogues are phosphodiester linkages.

43. The oligomer according to embodiment 38 wherein all the internucleoside linkages are phosphorothioate linkages.

44. A conjugate comprising the oligomer according to anyone of the embodiments 1-43 and at least one non-nucleotide or non-polynucleotide moiety covalently attached to said compound.

45. A pharmaceutical composition comprising an oligomer as defined in any of embodiments 1-43 or a conjugate as defined in embodiment 44, and a pharmaceutically acceptable diluent, carrier, salt or adjuvant.

46. A pharmaceutical composition according to 45, wherein the oligomer is constituted as a pro-drug.

47. Use of an oligomer as defined in anyone of the embodiments 1-43, or a conjugate as defined in embodiment 44, for the manufacture of a medicament for the treatment of a disease or disorder selected from the group consisting of hyperproliferative diseases such as cancer.

48. A method for treating a hyperproliferative disease such as cancer, said method comprising administering an oligomer as defined in one of the embodiments 1-43, or a conjugate as defined in embodiment 44, or a pharmaceutical composition as defined in anyone of the embodiments 45-46, to a patient in need thereof.

49. A method of reducing or inhibiting the expression of PIK3CA kinase in a cell or a tissue, the method comprising the step of contacting said cell or tissue with a compound as defined in one of the embodiments 1-43, or a conjugate as defined in embodiment 44, or a pharmaceutical composition as defined in anyone of the embodiments 45-46, so that expression of PIK3CA kinase is reduce or inhibited.

EXAMPLES

Example 1

Monomer Synthesis

The LNA monomer building blocks and derivatives were prepared following published procedures and references cited therein—see WO07/031,081, which is incorporated herein in its entirety, and the references cited therein.

Example 2

Oligonucleotide Synthesis

Oligonucleotides were synthesized according to the method described in WO 07/031,081. Table 2 shows examples of antisense oligonucleotide sequences of the invention. Tables 3 and 4 show examples of antisense oligonucleotides (oligomers) of the invention.

Example 3

Design of the Oligonucleotides

In accordance with the present invention, a series of different oligonucleotides were designed to target different regions of human PIK3CA mRNA (phosphoinositide-3-kinase, catalytic, alpha polypeptide). (GenBank Accession number NM_006218, SEQ ID NO: 1).

SEQ ID NOS 2-16: are oligomer sequences designed to target human wild-type PIK3CA mRNA (i.e., that are fully complementary to a target region of a wild-type PIK3CA mRNA).

TABLE 2

Antisense oligonucleotide sequences

| SEQ ID NO | Sequence (5'-3') | Length (bases) | Target site NM_006218 |
|---|---|---|---|
| SEQ ID NO: 2 | GAGGCATTCTAAAGTC | 16 | 253-268 |
| SEQ ID NO: 3 | ATTCTTCCCTTTCTGC | 16 | 386-401 |
| SEQ ID NO: 4 | TAGACATACATTGCTC | 16 | 642-657 |
| SEQ ID NO: 5 | TACTTGCCCTGATATT | 16 | 891-906 |
| SEQ ID NO: 6 | CACATAAGGGTTCTCC | 16 | 1247-1262 |
| SEQ ID NO: 7 | AGCCATTCATTCCACC | 16 | 1302-1317 |
| SEQ ID NO: 8 | CAGTAACACCAATAGG | 16 | 1529-1544 |
| SEQ ID NO: 9 | AACTCCAACTCTAAGC | 16 | 1572-1587 |
| SEQ ID NO: 10 | CAGACAGAAGCAATTT | 16 | 1856-1871 |
| SEQ ID NO: 11 | TTATTGTGCATCTCAG | 16 | 2175-2190 |
| SEQ ID NO: 12 | GCAGAGGACATAATTC | 16 | 2466-2481 |
| SEQ ID NO: 13 | GATGTCTGGGTTCTCC | 16 | 2506-2521 |
| SEQ ID NO: 14 | TTCTTCTTGTGATCCA | 16 | 2970-2985 |
| SEQ ID NO: 15 | AAGAAATCCTGTGTCA | 16 | 3024-3039 |
| SEQ ID NO: 16 | TCTCCTGAAACCTCTC | 16 | 3089-3104 |
| SEQ ID NO: 110 | CACGGAGGCATTCTAAAGTCACTA | 24 | 249-272 |
| SEQ ID NO: 111 | AAAAATTCTTCCCTTTCTGCTTCT | 24 | 382-405 |
| SEQ ID NO: 112 | AGGATAGACATACATTGCTCTACT | 24 | 638-661 |

TABLE 2-continued

Antisense oligonucleotide sequences

| SEQ ID NO | Sequence (5'-3') | Length (bases) | Target site NM_006218 |
|---|---|---|---|
| SEQ ID NO: 113 | AATATACTTGCCCTGATATTCTAA | 24 | 887-910 |
| SEQ ID NO: 114 | TTGTCACATAAGGGTTCTCCTCCA | 24 | 1243-1266 |
| SEQ ID NO: 115 | ATTCAGCCATTCATTCCACCTGGG | 24 | 1298-1321 |
| SEQ ID NO: 116 | GATCCAGTAACACCAATAGGGTTC | 24 | 1525-1548 |
| SEQ ID NO: 117 | GTCAAACTCCAACTCTAAGCATGG | 24 | 1568-1591 |
| SEQ ID NO: 118 | TTAACAGACAGAAGCAATTTGGGT | 24 | 1852-1875 |
| SEQ ID NO: 119 | TGTTTTATTGTGCATCTCAGATTT | 24 | 2171-2194 |
| SEQ ID NO: 120 | TTTTGCAGAGGACATAATTCGACA | 24 | 2462-2485 |
| SEQ ID NO: 121 | ACATGATGTCTGGGTTCTCCCAAT | 24 | 2502-2525 |
| SEQ ID NO: 122 | TTTTTTCTTCTTGTGATCCAAAAA | 24 | 2966-2989 |
| SEQ ID NO: 123 | TATTAAGAAATCCTGTGTCAAAAC | 24 | 3020-3043 |
| SEQ ID NO: 124 | CACATCTCCTGAAACCTCAAAT | 24 | 3085-3108 |

SEQ ID NOS: 17-22 show oligomer sequences designed to target the target regions of variants of human PIK3CA mRNA comprising each of the three hot-spot mutations (E542K, E545K and H1047R), and SEQ ID NOS: 23-28 show oligomer sequences that are fully complementary to the same target regions (i.e., those comprising hot-spot mutations in PIK3CA variants) of human wild-type PIK3CA. The base of each oligomer (having SEQ ID NOS: 23-28) that base pairs with the mutated base in the target regions of the variant PIK3CA nucleic acids is highlighted. The sequences of SEQ ID NOs: 125-136, respectively include the 16-mer sequences shown in SEQ ID NOs: 17-22 with additional monomers flanking the 16-mer sequences at the 5' and 3' ends. SEQ ID NOs: 17, 18, 125, and 126 are targeted to the target region comprising the E542K mutation. SEQ ID NOs: 19, 20, 127 and 128 are targeted to the target region comprising the E545K mutation, and SEQ ID NOs: 21, 22, 129 and 130 are targeted to the target region comprising the H1047R mutation.

TABLE 3

Antisense oligonucleotide sequences targeted to wild-type or mutant target regions of PIK3CA

| SEQ ID NO | Sequence (5'-3') | Length (bases) | Target site NM_006218 |
|---|---|---|---|
| SEQ ID NO: 17 | GATTTTAGAGAGAGGA | 16 | 1771-1786 |
| SEQ ID NO: 18 | AGTGATTTTAGAGAGA | 16 | 1774-1789 |
| SEQ ID NO: 19 | TCCTGCTTAGTGATTT | 16 | 1782-1797 |
| SEQ ID NO: 20 | TTCTCCTGCTTAGTGA | 16 | 1785-1800 |
| SEQ ID NO: 21 | GCCACCATGACGTGCA | 16 | 3292-3307 |
| SEQ ID NO: 22 | ACCATGACGTGCATCA | 16 | 3289-3304 |
| SEQ ID NO: 23 | GATTTCAGAGAGAGGA | 16 | 1771-1786 |
| SEQ ID NO: 24 | AGTGATTTCAGAGAGA | 16 | 1774-1789 |
| SEQ ID NO: 25 | TCCTGCTCAGTGATTT | 16 | 1782-1797 |
| SEQ ID NO: 26 | TTCTCCTGCTCAGTGA | 16 | 1785-1800 |
| SEQ ID NO: 27 | GCCACCATGATGTGCA | 16 | 3292-3307 |
| SEQ ID NO: 28 | ACCATGATGTGCATCA | 16 | 3289-3304 |
| SEQ ID NO: 125 | CAGTGATTTTAGAGAGAGGATCTC | 24 | 1767-1790 |
| SEQ ID NO: 126 | GCTCAGTGATTTTAGAGAGAGGAT | 24 | 1770-1793 |

TABLE 3-continued

Antisense oligonucleotide sequences targeted to wild-type or mutant target regions of PIK3CA

| SEQ ID NO | Sequence (5'-3') | Length (bases) | Target site NM_006218 |
|---|---|---|---|
| SEQ ID NO: 127 | TTTCTCCTGCTTAGTGATTTCAGA | 24 | 1778-1801 |
| SEQ ID NO: 128 | ATCTTTCTCCTGCTTAGTGATTTC | 24 | 1781-1804 |
| SEQ ID NO: 129 | TCCAGCCACCATGACGTGCATCAT | 24 | 3288-3311 |
| SEQ ID NO: 130 | AGCCACCATGACGTGCATCATTCA | 24 | 3285-3308 |
| SEQ ID NO: 131 | CAGTGATTTCAGAGAGGATCTC | 24 | 1767-1790 |
| SEQ ID NO: 132 | GCTCAGTGATTTCAGAGAGGAT | 24 | 1770-1793 |
| SEQ ID NO: 133 | TTTCTCCTGCTCAGTGATTTCAGA | 24 | 1778-1801 |
| SEQ ID NO: 134 | ATCTTTCTCCTGCTCAGTGATTTC | 24 | 1781-1804 |
| SEQ ID NO: 135 | TCCAGCCACCATGATGTGCATCAT | 24 | 3288-3311 |
| SEQ ID NO: 136 | AGCCACCATGATGTGCATCATTCA | 24 | 3285-3308 |

In SEQ ID NOs: 29-55, upper case letters indicates nucleoside analogue units (nucleoside analogue monomers), such as LNA monomers, and subscript "s" represents a phosphorothiote linkage. The absence of "s" (if any) indicates phosphodiester linkage. Lower case letters represent nucleoside (such as DNA or RNA monomers). All cytosine bases in the LNA monomers are 5-methylcytosines.

TABLE 4

Oligonucleotide designs of the invention

| SEQ ID NO | Sequence (5'-3') |
|---|---|
| SEQ ID NO: 29 | G$_s$A$_s$G$_s$g$_s$c$_s$a$_s$t$_s$c$_s$t$_s$a$_s$a$_s$a$_s$G$_s$T$_s$C |
| SEQ ID NO: 30 | A$_s$T$_s$T$_s$c$_s$t$_s$t$_s$c$_s$c$_s$c$_s$t$_s$t$_s$c$_s$T$_s$G$_s$C |
| SEQ ID NO: 31 | T$_s$A$_s$G$_s$a$_s$c$_s$a$_s$t$_s$a$_s$c$_s$a$_s$t$_s$t$_s$g$_s$C$_s$T$_s$C |
| SEQ ID NO: 32 | T$_s$A$_s$C$_s$t$_s$t$_s$g$_s$c$_s$c$_s$c$_s$t$_s$g$_s$a$_s$t$_s$A$_s$T$_s$T |
| SEQ ID NO: 33 | C$_s$A$_s$C$_s$a$_s$t$_s$a$_s$a$_s$g$_s$g$_s$g$_s$t$_s$t$_s$c$_s$T$_s$C$_s$C |
| SEQ ID NO: 34 | A$_s$G$_s$C$_s$c$_s$a$_s$t$_s$t$_s$c$_s$a$_s$t$_s$t$_s$c$_s$c$_s$A$_s$C$_s$C |
| SEQ ID NO: 35 | C$_s$A$_s$G$_s$t$_s$a$_s$a$_s$c$_s$a$_s$c$_s$c$_s$a$_s$a$_s$t$_s$A$_s$G$_s$G |
| SEQ ID NO: 36 | A$_s$A$_s$C$_s$t$_s$c$_s$c$_s$a$_s$a$_s$c$_s$t$_s$c$_s$t$_s$a$_s$A$_s$G$_s$C |
| SEQ ID NO: 37 | C$_s$A$_s$G$_s$a$_s$c$_s$a$_s$g$_s$a$_s$a$_s$g$_s$c$_s$a$_s$a$_s$T$_s$T$_s$T |
| SEQ ID NO: 38 | T$_s$T$_s$A$_s$t$_s$t$_s$g$_s$t$_s$g$_s$c$_s$a$_s$t$_s$c$_s$t$_s$C$_s$A$_s$G |
| SEQ ID NO: 39 | G$_s$C$_s$A$_s$g$_s$a$_s$g$_s$g$_s$a$_s$c$_s$a$_s$t$_s$a$_s$a$_s$T$_s$T$_s$C |
| SEQ ID NO: 40 | G$_s$A$_s$T$_s$g$_s$t$_s$c$_s$t$_s$g$_s$g$_s$g$_s$t$_s$t$_s$c$_s$T$_s$C$_s$C |
| SEQ ID NO: 41 | T$_s$T$_s$C$_s$t$_s$t$_s$c$_s$t$_s$t$_s$g$_s$t$_s$g$_s$a$_s$t$_s$C$_s$C$_s$A |
| SEQ ID NO: 42 | A$_s$A$_s$G$_s$a$_s$a$_s$a$_s$t$_s$c$_s$c$_s$t$_s$g$_s$t$_s$g$_s$T$_s$C$_s$A |
| SEQ ID NO: 43 | T$_s$C$_s$T$_s$c$_s$c$_s$t$_s$g$_s$a$_s$a$_s$a$_s$c$_s$c$_s$t$_s$C$_s$T$_s$C |
| SEQ ID NO: 44 | G$_s$A$_s$T$_s$t$_s$t$_s$t$_s$a$_s$g$_s$a$_s$g$_s$a$_s$g$_s$a$_s$G$_s$G$_s$A |
| SEQ ID NO: 45 | A$_s$G$_s$T$_s$g$_s$a$_s$t$_s$t$_s$t$_s$a$_s$g$_s$a$_s$g$_s$A$_s$G$_s$A |
| SEQ ID NO: 46 | T$_s$C$_s$C$_s$t$_s$g$_s$c$_s$t$_s$t$_s$a$_s$g$_s$t$_s$g$_s$a$_s$T$_s$T$_s$T |
| SEQ ID NO: 47 | T$_s$T$_s$C$_s$t$_s$c$_s$c$_s$t$_s$g$_s$c$_s$t$_s$t$_s$a$_s$g$_s$T$_s$G$_s$A |
| SEQ ID NO: 48 | G$_s$C$_s$C$_s$a$_s$c$_s$c$_s$a$_s$t$_s$g$_s$a$_s$c$_s$g$_s$t$_s$G$_s$C$_s$A |
| SEQ ID NO: 49 | A$_s$C$_s$C$_s$a$_s$t$_s$g$_s$a$_s$c$_s$g$_s$t$_s$g$_s$c$_s$a$_s$T$_s$C$_s$A |
| SEQ ID NO: 50 | G$_s$A$_s$T$_s$t$_s$t$_s$c$_s$a$_s$g$_s$a$_s$g$_s$a$_s$g$_s$a$_s$G$_s$G$_s$A |
| SEQ ID NO: 51 | A$_s$G$_s$T$_s$g$_s$a$_s$t$_s$t$_s$t$_s$c$_s$a$_s$g$_s$a$_s$g$_s$A$_s$G$_s$A |
| SEQ ID NO: 52 | T$_s$C$_s$C$_s$t$_s$g$_s$c$_s$t$_s$c$_s$a$_s$g$_s$t$_s$g$_s$a$_s$T$_s$T$_s$T |
| SEQ ID NO: 53 | T$_s$T$_s$C$_s$t$_s$c$_s$c$_s$t$_s$g$_s$c$_s$t$_s$c$_s$a$_s$g$_s$T$_s$G$_s$A |
| SEQ ID NO: 54 | G$_s$C$_s$C$_s$a$_s$c$_s$c$_s$a$_s$t$_s$g$_s$a$_s$t$_s$g$_s$t$_s$G$_s$C$_s$A |
| SEQ ID NO: 55 | A$_s$C$_s$C$_s$a$_s$t$_s$g$_s$a$_s$t$_s$g$_s$t$_s$g$_s$c$_s$a$_s$T$_s$C$_s$A |

Example 4

In Vitro Model

Cell Culture

The effect of antisense oligonucleotides on target nucleic acid expression can be tested in any of a variety of cell types provided that the target nucleic acid is present at measurable levels. The target can be expressed endogenously or by transient or stable transfection of a nucleic acid encoding said target. The expression level of target nucleic acid can be routinely determined using, for example, Northern blot analysis, Real-Time PCR, Ribonuclease protection assays. The following cell types are provided for illustrative purposes, but other cell types can be routinely used, provided that the target is expressed in the cell type chosen.

Cells were cultured in the appropriate medium as described below and maintained at 37° C. at 95-98% humidity and 5% $CO_2$. Cells were routinely passaged 2-3 times weekly.

MCF7: The human breast adenocarcinoma cell line MCF7 was cultured in Eagle MEM (Sigma)+10% fetal bovine serum (FBS)+2 mM Glutamax I+gentamicin (25 µg/ml)+1× Non Essential Amino Acid.

PC3: The human prostate adenocarcinoma cell line PC3 was cultured in DMEM (Sigma)+10% fetal bovine serum (FBS)+2 mM Glutamax I+gentamicin (25 µg/ml).

Example 5

In Vitro Model

Treatment with Antisense Oligonucleotide

The cell lines listed in Example 4 were treated with oligonucleotide using the cationic liposome formulation LipofectAMINE 2000 (Gibco) as transfection vehicle. Cells were seeded in 6-well cell culture plates (NUNC) and treated when 80-90% confluent. Oligomer concentrations used ranged from 0.8 nM to 20 nM final concentration. Formulation of oligomer-lipid complexes were carried out essentially as described by the manufacturer using serum-free OptiMEM (Gibco) and a final lipid concentration of 2.5 µg/mL (PC3) or 5 µg/mL (MCF7) LipofectAMINE 2000. Cells were incubated at 37° C. for 4 hours and treatment was stopped by removal of oligomer-containing culture medium. Cells were washed and serum-containing media was added. After oligomer treatment cells, were allowed to recover for 20 hours before they were harvested for RNA analysis.

Example 6

In Vitro Model

Extraction of RNA and cDNA Synthesis

Total RNA Isolation and First strand synthesis: Total RNA was extracted from cells transfected as described above and using the Qiagen RNeasy kit (Qiagen cat. no. 74104) according to the manufacturer's instructions. First strand synthesis was performed using Reverse Transcriptase reagents from Ambion according to the manufacturer's instructions.

For each sample 0.5·g total RNA was adjusted to (10.8·1) with RNase free H$_2$O and mixed with 2·1 random decamers (50·M) and 4·1 dNTP mix (2.5 mM each dNTP) and heated to 70° C. for 3 min after which the samples were rapidly cooled on ice. After cooling the samples on ice, 2·1 10× Buffer RT, 1·1MMLV Reverse Transcriptase (100 U/·1) and 0.25·1 RNase inhibitor (10 U/·1) were added to each sample, followed by incubation at 42° C. for 60 min, heat inactivation of the enzyme at 95° C. for 10 min and then the sample was cooled to 4° C.

Example 7

In Vitro Model

Analysis of Oligonucleotide Inhibition of PIK3CA Expression by Real-Time PCR

Antisense modulation of PIK3CA expression can be assayed in a variety of ways known in the art. For example, PIK3CA mRNA levels can be quantitated by, e.g., Northern blot analysis, competitive polymerase chain reaction (PCR), or real-time PCR. Real-time quantitative PCR is presently preferred. RNA analysis can be performed on total cellular RNA or mRNA.

Methods of RNA isolation and RNA analysis such as Northern blot analysis, are routine in the art and are taught in, for example, Current Protocols in Molecular Biology. John Wiley and Sons.

Real-time quantitative PCR can be conveniently accomplished using the commercially available Multi-Color Real Time PCR Detection System, available from Applied Biosystems.

Real-time Quantitative PCR Analysis of PIK3CA mRNA Levels: The sample content of human PIK3CA mRNA was quantified using the human PIK3CA ABI Prism Pre-Developed TaqMan Assay Reagents (Applied Biosystems cat. no. Hs00180679_ml) according to the manufacturer's instructions.

Glyceraldehyde-3-phosphate dehydrogenase (GAPDH) mRNA quantity was used as an endogenous control for normalizing any variance in sample preparation.

The sample content of human GAPDH mRNA was quantified using the human GAPDH ABI Prism Pre-Developed TaqMan Assay Reagent (Applied Biosystems cat. no. 4310884E) according to the manufacturer's instructions.

Real-time Quantitative PCR is a technique well known in the art and is taught in for example Heid et al. Real time quantitative PCR, Genome Research (1996), 6: 986-994.

Real time peR: The cDNA from the first strand synthesis performed as described in Example 5 was diluted 2-20 times, and analyzed by real time quantitative PCR using Taqman 7500 FAST or 7900 FAST from Applied Biosystems. The primers and probe were mixed with 2× Taqman Fast Universal PCR master mix (2×) (Applied Biosystems Cat.#4364103) and added to 4 µl cDNA to a final volume of 10 µl. Each sample was analysed in duplicate. Assaying 2-fold dilutions of a cDNA that had been prepared on material purified from a cell line expressing the RNA of interest generated standard curves for the assays. Sterile H$_2$O was used instead of cDNA for the no-template control. PCR program: 95° C. for 30 seconds, followed by 40 cycles of 95° C., 3 seconds, 60° C., 20-30 seconds. Relative quantities of target mRNA sequence were determined from the calculated Threshold cycle using the Applied Biosystems Fast System SDS Software Version 1.3.1.21. or SDS Software Version 2.3.

Example 8

In Vitro Analysis

Figure 2:
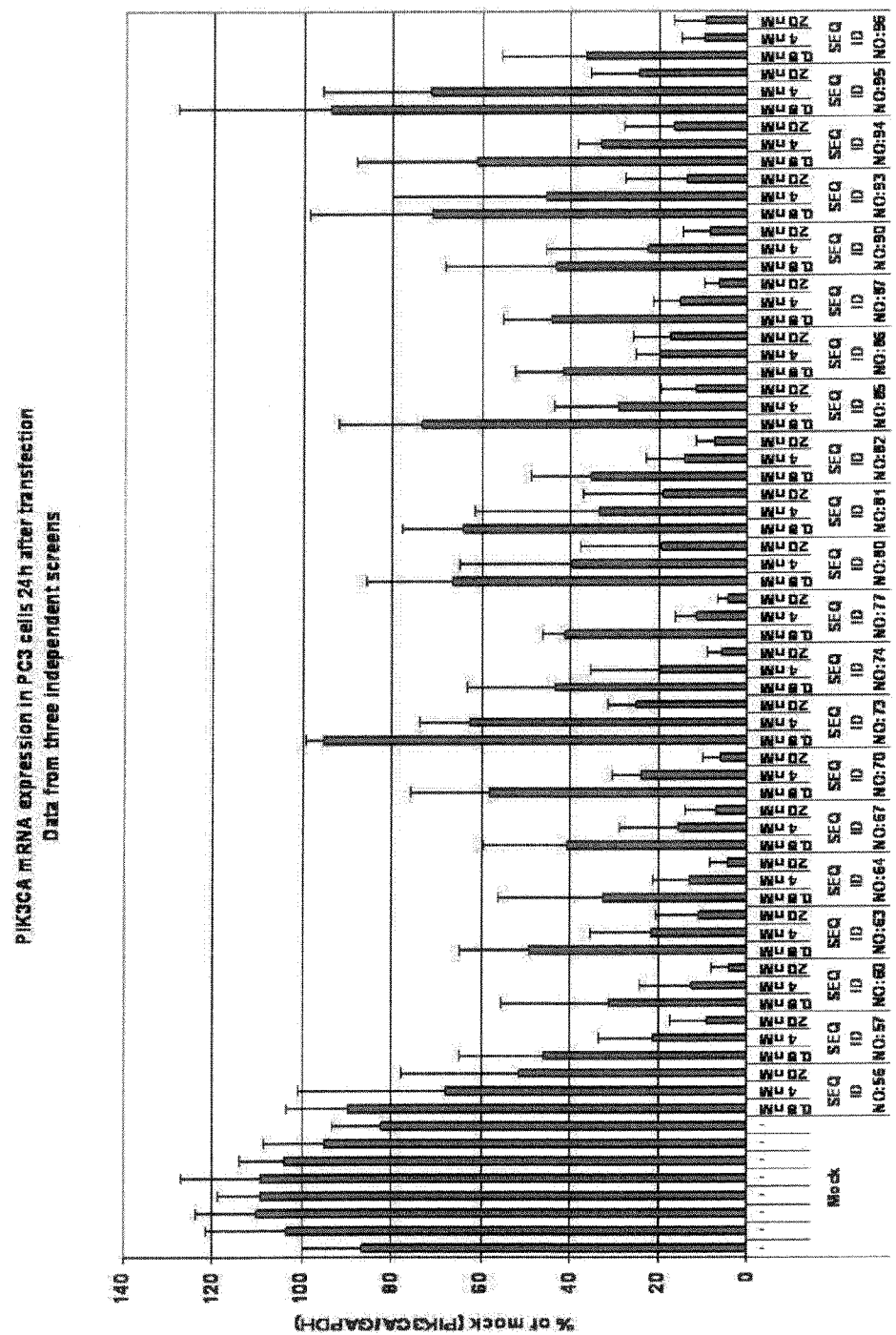
FIG. 2. Oligonucleotides presented in Table 5 were evaluated for their potential to knock down the PIK3CA mRNA at concentrations of 0.8 nM, 4 nM and 20 nM in PC3 cells 24 hours after transfection using Real-time PCR. All results were normalised to GAPDH and inhibition of PIK3CA mRNA is shown as percent of mock-transfected control. Results shown are the average of results from three independent experiments.
Figure 22:
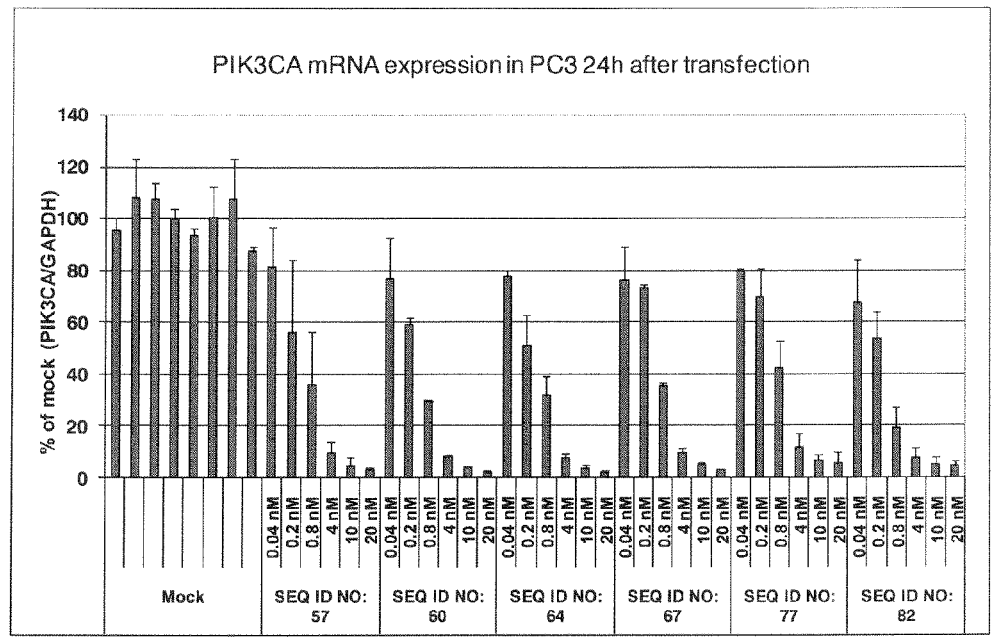
FIG. 22. The most potent oligonucleotides were evaluated for their potential to knock down the PIK3CA mRNA at concentrations of 0.04 nM, 0.2 nM, 0.8 nM, 4 nM, 10 nM and 20 nM in PC3 cells 24 hours after transfection using Real-time PCR. All results were normalised to GAPDH and inhibition of PIK3CA mRNA is shown as percent of mock-transfected control. Results shown are the average of two independent experiments.
Figure 23:
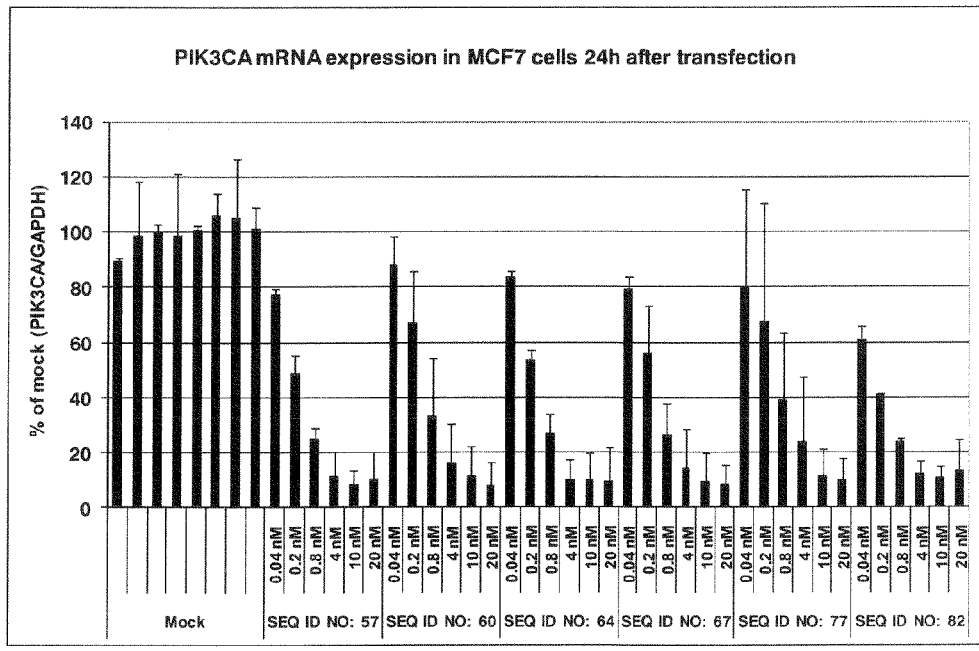
FIG. 23. The most potent oligonucleotides were evaluated for their potential to knock down the PIK3CA mRNA at concentrations of 0.04 nM, 0.2 nM, 0.8 nM, 4 nM, 10 nM and 20 nM in MCF7 cells 24 hours after transfection using Real-time PCR. All results were normalised to GAPDH and inhibition of PIK3CA mRNA is shown as percent of mock-transfected control. Results shown are the average of two independent experiments.

Antisense Inhibition of Human PIK3CA mRNA Expression by Oligonucleotide Compounds Oligonucleotides presented in Table 4 were evaluated for their potential to knock down expression of human PIK3CA mRNA at concentrations of 0.8 nM, 4 nM and 20 nM in PC3 cells and MCF7 cells (see FIGS. 1 and 2). The most active oligonucleotides, having SEQ ID NOs: 57, 60, 64, 67, 77 and 82 were further evaluated for their ability to knock down human PIK3CA mRNA at the concentrations 0.04 nM, 0.2 nM, 0.8 nM, 4 nM, 10 nM and 20 nM in PC3 and MCF7 cells (see FIGS. 22 and 23).

The data in Table 5 are presented as percentage downregulation relative to mock transfected cells at 20 nM. Lower case letters represent DNA monomers, bold upper case letters represent β-D-oxy-LNA monomers. All cytosines in LNA monomers are 5-methylcytosines. Subscript "s" represents a phosphorothioate linkage.

| Test substance | Sequence (5'-3') | Percent inhibition of PIK3CA in MCF7 | Percent inhibition of PIK3CA in PC3 |
|---|---|---|---|
| SEQ ID NO: 56 | G$_s$A$_s$G$_s$c$_s$a$_s$t$_s$t$_s$c$_s$t$_s$a$_s$a$_s$a$_s$G$_s$T$_s$C | 47 | 48 |
| SEQ ID NO: 57 | A$_s$T$_s$T$_s$c$_s$t$_s$t$_s$c$_s$c$_s$c$_s$t$_s$t$_s$t$_s$c$_s$T$_s$G$_s$C | 94 | 91 |
| SEQ ID NO: 58 | T$_s$T$_s$C$_s$t$_s$t$_s$c$_s$c$_s$c$_s$c$_s$t$_s$t$_s$t$_s$c$_s$T$_s$G | n.d. | n.d. |
| SEQ ID NO: 59 | T$_s$C$_s$t$_s$t$_s$c$_s$c$_s$c$_s$t$_s$t$_s$t$_s$C$_s$T | n.d. | n.d. |
| SEQ ID NO: 60 | T$_s$A$_s$G$_s$a$_s$c$_s$a$_s$t$_s$a$_s$c$_s$a$_s$t$_s$t$_s$g$_s$C$_s$T$_s$C | 96 | 96 |
| SEQ ID NO: 61 | A$_s$G$_s$A$_s$c$_s$a$_s$t$_s$a$_s$c$_s$a$_s$t$_s$t$_s$g$_s$C$_s$T | n.d. | n.d. |
| SEQ ID NO: 62 | G$_s$S$_s$c$_s$a$_s$t$_s$a$_s$c$_s$a$_s$t$_s$t$_s$G$_s$C | n.d. | n.d. |
| SEQ ID NO: 63 | T$_s$A$_s$C$_s$t$_s$t$_s$g$_s$c$_s$c$_s$c$_s$t$_s$g$_s$a$_s$t$_s$A$_s$T$_s$T | 94 | 89 |
| SEQ ID NO: 64 | C$_s$A$_s$C$_s$a$_s$t$_s$a$_s$a$_s$g$_s$g$_s$g$_s$t$_s$t$_s$c$_s$T$_s$C$_s$C | 97 | 95 |
| SEQ ID NO: 65 | A$_s$C$_s$A$_s$t$_s$a$_s$a$_s$g$_s$g$_s$g$_s$t$_s$t$_s$c$_s$T$_s$C | n.d. | n.d. |
| SEQ ID NO: 66 | C$_s$A$_s$t$_s$a$_s$a$_s$g$_s$g$_s$g$_s$t$_s$t$_s$C$_s$T | n.d. | n.d. |
| SEQ ID NO: 67 | A$_s$G$_s$C$_s$c$_s$a$_s$t$_s$t$_s$c$_s$a$_s$t$_s$t$_s$c$_s$c$_s$A$_s$C$_s$C | 97 | 93 |
| SEQ ID NO: 68 | G$_s$C$_s$C$_s$a$_s$t$_s$t$_s$c$_s$a$_s$t$_s$t$_s$c$_s$c$_s$A$_s$C | n.d. | n.d. |
| SEQ ID NO: 69 | C$_s$C$_s$a$_s$t$_s$t$_s$c$_s$a$_s$t$_s$t$_s$c$_s$C$_s$A | n.d. | n.d. |
| SEQ ID NO: 70 | C$_s$A$_s$G$_s$t$_s$a$_s$a$_s$c$_s$a$_s$c$_s$c$_s$a$_s$a$_s$t$_s$A$_s$G$_s$G | 92 | 94 |
| SEQ ID NO: 71 | A$_s$G$_s$T$_s$a$_s$a$_s$c$_s$a$_s$c$_s$c$_s$a$_s$a$_s$t$_s$A$_s$G | n.d. | n.d. |
| SEQ ID NO: 72 | G$_s$T$_s$a$_s$a$_s$c$_s$a$_s$c$_s$c$_s$a$_s$a$_s$T$_s$A | n.d. | n.d. |
| SEQ ID NO: 73 | A$_s$A$_s$C$_s$t$_s$c$_s$c$_s$a$_s$a$_s$c$_s$t$_s$c$_s$t$_s$a$_s$A$_s$G$_s$C | 81 | 75 |
| SEQ ID NO: 74 | C$_s$A$_s$G$_s$a$_s$c$_s$a$_s$g$_s$a$_s$a$_s$g$_s$c$_s$a$_s$a$_s$T$_s$T$_s$T | 90 | 94 |
| SEQ ID NO: 75 | A$_s$G$_s$a$_s$c$_s$a$_s$g$_s$a$_s$a$_s$g$_s$c$_s$a$_s$a$_s$T$_s$T | n.d. | n.d. |
| SEQ ID NO: 76 | G$_s$A$_s$c$_s$a$_s$g$_s$a$_s$a$_s$g$_s$c$_s$a$_s$A$_s$T | n.d. | n.d. |
| SEQ ID NO: 77 | T$_s$T$_s$A$_s$t$_s$t$_s$g$_s$t$_s$g$_s$c$_s$a$_s$t$_s$c$_s$t$_s$C$_s$A$_s$G | 91 | 96 |
| SEQ ID NO: 78 | T$_s$A$_s$T$_s$t$_s$g$_s$t$_s$g$_s$c$_s$a$_s$t$_s$c$_s$t$_s$C$_s$A | n.d. | n.d. |
| SEQ ID NO: 79 | A$_s$T$_s$t$_s$g$_s$t$_s$g$_s$c$_s$a$_s$t$_s$c$_s$T$_s$C | n.d. | n.d. |
| SEQ ID NO: 80 | G$_s$C$_s$A$_s$g$_s$a$_s$g$_s$g$_s$a$_s$c$_s$a$_s$t$_s$a$_s$a$_s$T$_s$T$_s$C | 76 | 80 |
| SEQ ID NO: 81 | G$_s$A$_s$T$_s$g$_s$t$_s$c$_s$t$_s$g$_s$g$_s$g$_s$t$_s$t$_s$c$_s$T$_s$C$_s$C | 90 | 81 |
| SEQ ID NO: 82 | T$_s$T$_s$C$_s$t$_s$t$_s$c$_s$t$_s$t$_s$g$_s$t$_s$g$_s$a$_s$t$_s$C$_s$C$_s$A | 92 | 93 |
| SEQ ID NO: 83 | T$_s$C$_s$T$_s$t$_s$c$_s$t$_s$t$_s$g$_s$t$_s$g$_s$a$_s$t$_s$C$_s$C | n.d. | n.d. |
| SEQ ID NO: 84 | C$_s$T$_s$t$_s$c$_s$t$_s$t$_s$g$_s$t$_s$g$_s$a$_s$t$_s$T$_s$C | n.d. | n.d. |
| SEQ ID NO: 85 | A$_s$A$_s$G$_s$a$_s$a$_s$a$_s$t$_s$c$_s$c$_s$t$_s$g$_s$t$_s$g$_s$T$_s$C$_s$A | 87 | 88 |
| SEQ ID NO: 86 | T$_s$C$_s$T$_s$c$_s$c$_s$t$_s$g$_s$a$_s$a$_s$a$_s$c$_s$c$_s$t$_s$C$_s$T$_s$C | 85 | 83 |
| SEQ ID NO: 87 | G$_s$A$_s$T$_s$t$_s$t$_s$c$_s$a$_s$g$_s$a$_s$g$_s$a$_s$g$_s$a$_s$G$_s$G$_s$A | 94 | 94 |
| SEQ ID NO: 88 | A$_s$T$_s$T$_s$c$_s$a$_s$g$_s$a$_s$g$_s$asg$_s$a$_s$G$_s$G | n.d. | n.d. |
| SEQ ID NO: 89 | T$_s$T$_s$c$_s$a$_s$g$_s$a$_s$g$_s$a$_s$g$_s$A$_s$G | n.d. | n.d. |
| SEQ ID NO: 90 | A$_s$G$_s$T$_s$g$_s$a$_s$t$_s$t$_s$t$_s$c$_s$a$_s$g$_s$a$_s$g$_s$A$_s$G$_s$A | 96 | 92 |
| SEQ ID NO: 91 | G$_s$T$_s$G$_s$a$_s$t$_s$t$_s$t$_s$c$_s$a$_s$g$_s$a$_s$g$_s$A$_s$G | n.d. | n.d. |
| SEQ ID NO: 92 | T$_s$G$_s$a$_s$t$_s$t$_s$t$_s$c$_s$a$_s$g$_s$a$_s$G$_s$A | n.d. | n.d. |
| SEQ ID NO: 93 | T$_s$C$_s$C$_s$t$_s$g$_s$c$_s$t$_s$c$_s$a$_s$g$_s$t$_s$g$_s$a$_s$T$_s$T$_s$T | 85 | 86 |

-continued

| Test substance | Sequence (5'-3') | Percent inhibition of PIK3CA in MCF7 | Percent inhibition of PIK3CA in PC3 |
|---|---|---|---|
| SEQ ID NO: 94 | T$_s$T$_s$C$_s$t$_s$c$_s$c$_s$t$_s$g$_s$c$_s$t$_s$c$_s$a$_s$g$_s$T$_s$G$_s$A | 78 | 83 |
| SEQ ID NO: 95 | G$_s$C$_s$C$_s$a$_s$c$_s$c$_s$a$_s$t$_s$g$_s$a$_s$t$_s$g$_s$t$_s$G$_s$C$_s$A | 84 | 75 |
| SEQ ID NO: 96 | A$_s$C$_s$C$_s$a$_s$t$_s$g$_s$a$_s$t$_s$g$_s$t$_s$g$_s$c$_s$a$_s$T$_s$C$_s$A | 94 | 91 |
| SEQ ID NO: 97 | C$_s$C$_s$a$_s$t$_s$g$_s$a$_s$t$_s$g$_s$t$_s$g$_s$c$_s$a$_s$T$_s$C | n.d. | n.d. |
| SEQ ID NO: 98 | C$_s$A$_s$t$_s$g$_s$a$_s$t$_s$g$_s$t$_s$g$_s$C$_s$A$_s$T | n.d. | n.d. |
| SEQ ID NO: 99 | G$_s$A$_s$T$_s$t$_s$t$_s$t$_s$a$_s$g$_s$a$_s$g$_s$a$_s$g$_s$a$_s$G$_s$G$_s$A | n.d. | n.d. |
| SEQ ID NO: 137 | A$_s$T$_s$T$_s$t$_s$t$_s$a$_s$g$_s$a$_s$g$_s$a$_s$g$_s$A$_s$G$_s$G | n.d. | n.d. |
| SEQ ID NO: 138 | T$_s$T$_s$t$_s$t$_s$a$_s$g$_s$a$_s$g$_s$a$_s$g$_s$A$_s$G | n.d. | n.d. |
| SEQ ID NO: 100 | A$_s$G$_s$T$_s$g$_s$a$_s$t$_s$t$_s$t$_s$a$_s$g$_s$a$_s$g$_s$A$_s$G$_s$A | n.d. | n.d. |
| SEQ ID NO: 139 | G$_s$T$_s$G$_s$a$_s$t$_s$t$_s$t$_s$a$_s$g$_s$a$_s$G$_s$A$_s$G | n.d. | n.d. |
| SEQ ID NO: 140 | T$_s$G$_s$a$_s$t$_s$t$_s$t$_s$a$_s$g$_s$a$_s$G$_s$A | n.d. | n.d. |
| SEQ ID NO: 101 | T$_s$C$_s$C$_s$t$_s$g$_s$c$_s$t$_s$t$_s$a$_s$g$_s$t$_s$g$_s$a$_s$T$_s$T$_s$T | n.d. | n.d. |
| SEQ ID NO: 141 | C$_s$C$_s$T$_s$g$_s$c$_s$t$_s$t$_s$a$_s$g$_s$t$_s$g$_s$A$_s$T$_s$T | n.d. | n.d. |
| SEQ ID NO: 142 | C$_s$T$_s$g$_s$c$_s$t$_s$t$_s$a$_s$g$_s$t$_s$g$_s$A$_s$T | n.d. | n.d. |
| SEQ ID NO: 102 | T$_s$T$_s$C$_s$t$_s$c$_s$c$_s$t$_s$g$_s$c$_s$t$_s$t$_s$a$_s$g$_s$T$_s$G$_s$A | n.d. | n.d. |
| SEQ ID NO: 143 | T$_s$C$_s$T$_s$c$_s$c$_s$t$_s$g$_s$c$_s$t$_s$t$_s$a$_s$G$_s$T$_s$G | n.d. | n.d. |
| SEQ ID NO: 144 | C$_s$T$_s$c$_s$c$_s$t$_s$g$_s$c$_s$t$_s$t$_s$a$_s$G$_s$T | n.d. | n.d. |
| SEQ ID NO: 103 | G$_s$C$_s$C$_s$a$_s$c$_s$c$_s$a$_s$t$_s$g$_s$a$_s$c$_s$g$_s$t$_s$G$_s$C$_s$A | n.d. | n.d. |
| SEQ ID NO: 145 | C$_s$C$_s$A$_s$c$_s$c$_s$a$_s$t$_s$g$_s$a$_s$c$_s$g$_s$T$_s$G$_s$C | n.d. | n.d. |
| SEQ ID NO: 146 | C$_s$A$_s$c$_s$c$_s$a$_s$t$_s$g$_s$a$_s$c$_s$g$_s$T$_s$G | n.d. | n.d. |
| SEQ ID NO: 104 | A$_s$C$_s$C$_s$a$_s$t$_s$g$_s$a$_s$c$_s$g$_s$t$_s$g$_s$c$_s$a$_s$T$_s$C$_s$A | n.d. | n.d. |
| SEQ ID NO: 147 | C$_s$C$_s$A$_s$t$_s$g$_s$a$_s$c$_s$g$_s$t$_s$g$_s$c$_s$A$_s$T$_s$C | n.d. | n.d. |
| SEQ ID NO: 148 | C$_s$A$_s$t$_s$g$_s$a$_s$c$_s$g$_s$t$_s$g$_s$c$_s$A$_s$T | n.d. | n.d. |

As shown in Table 5, oligonucleotides having the sequences of SEQ ID NOs: 57, 60, 64, 67, 70, 74, 77, 82, 87, 90 and 96 demonstrated about 90% or greater inhibition of PIK3CA mRNA expression at 20 nM in PC3 and MCF7 cells in these experiments.

In certain embodiments, oligomers based on the tested antisense oligomer sequences and designs, but having, for example, different lengths (shorter or longer) and/or monomer content (e.g. the type and/or number of nucleoside analogues) than those shown, e.g., in Table 5, could also provide suitable inhibition of PIK3CA expression.

Example 9

In Vitro Analysis

Effect of Antisense Inhibition of Human PIK3CA mRNA on Cell Proliferation (MTS Assay)

Figure 11:
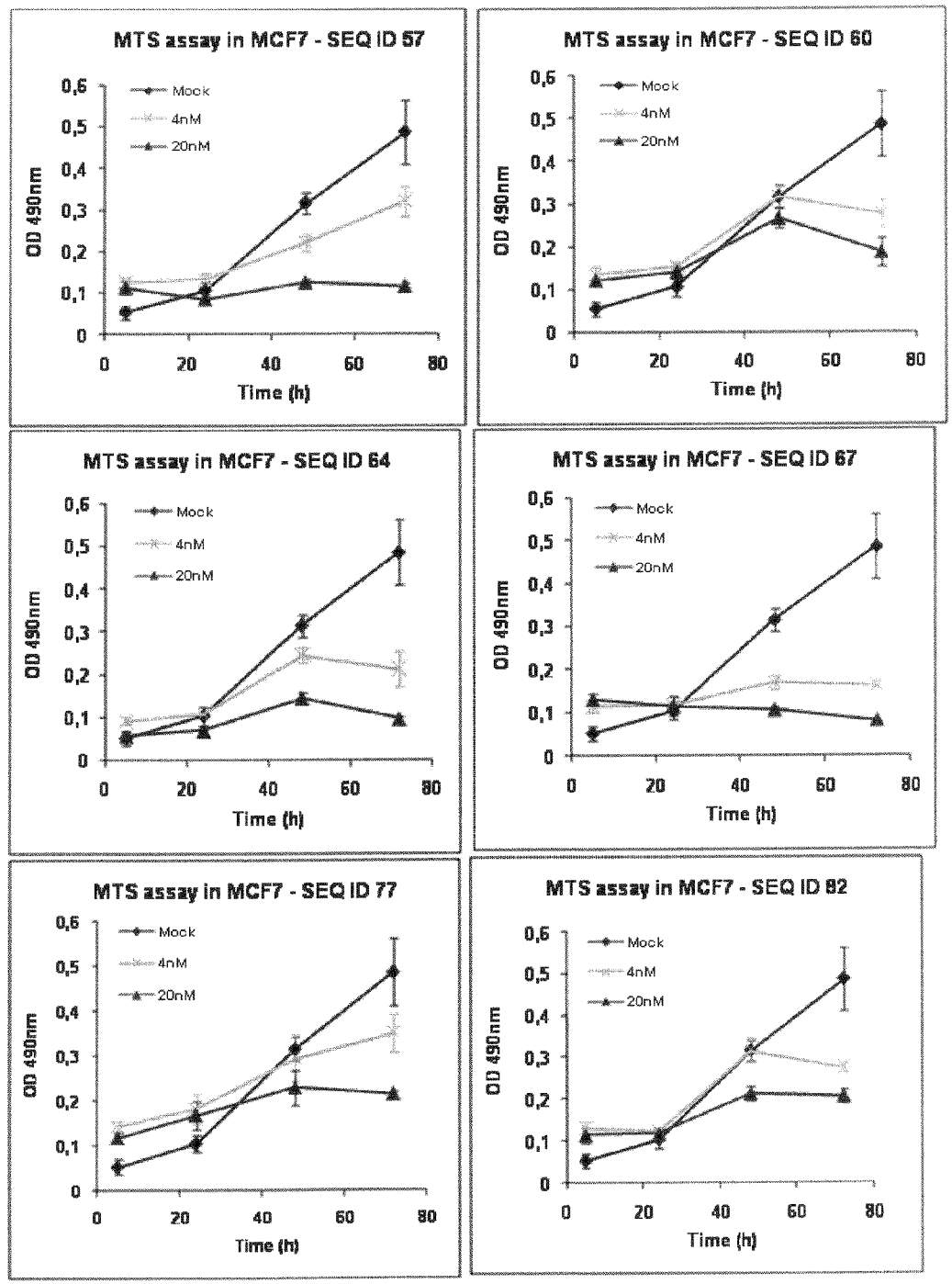
FIG. 11. Cell proliferation assay (MTS assay) in MCF7 cells. Four independent experiments were performed. The results from the experiment best representing the average activity of each oligomer are shown.
Figure 12:
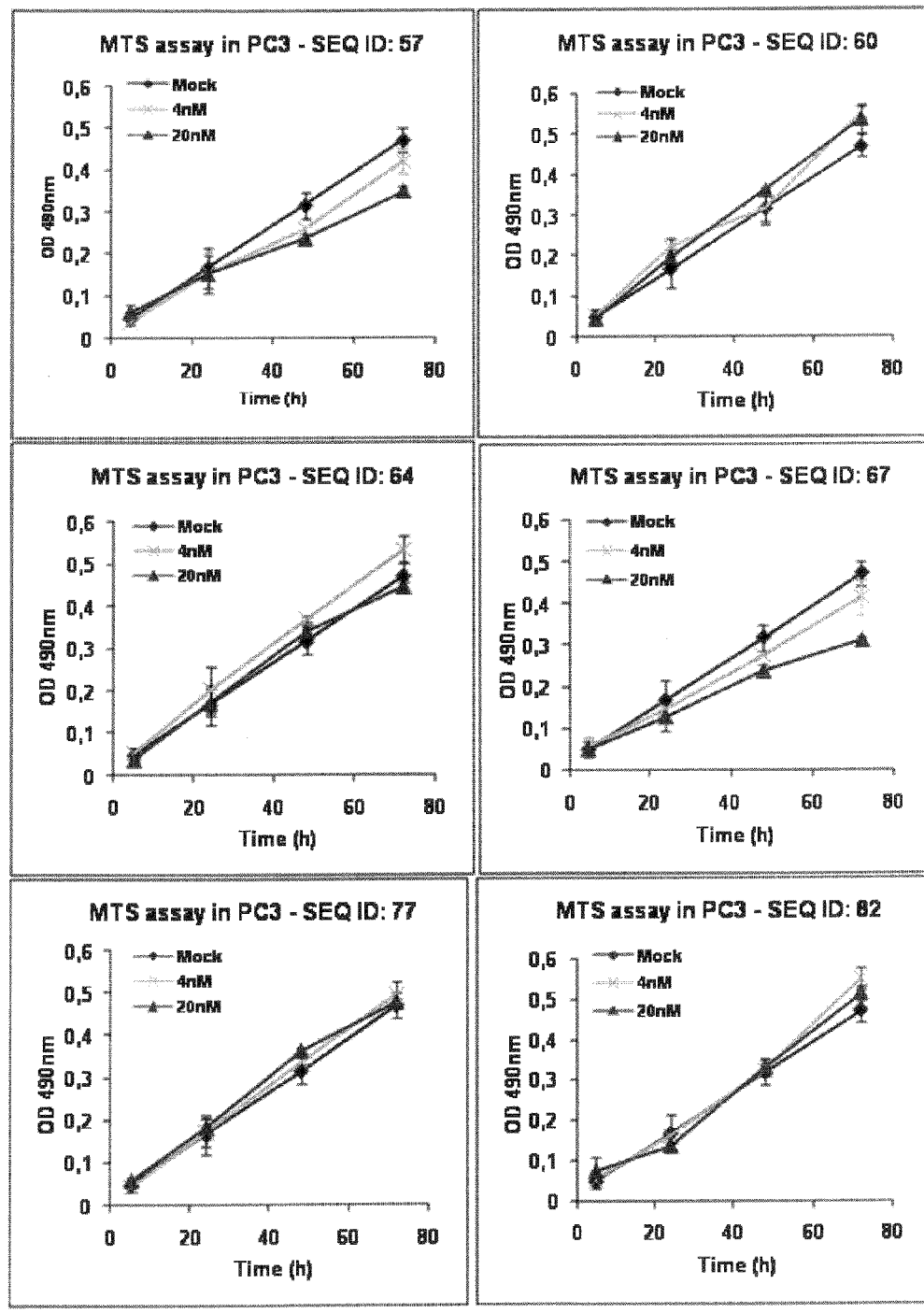
FIG. 12. Cell proliferation assay (MTS) in PC3 cells. Two independent experiments were performed. The results from the experiment best representing the average activity of each oligomer are shown.
Figure 14:
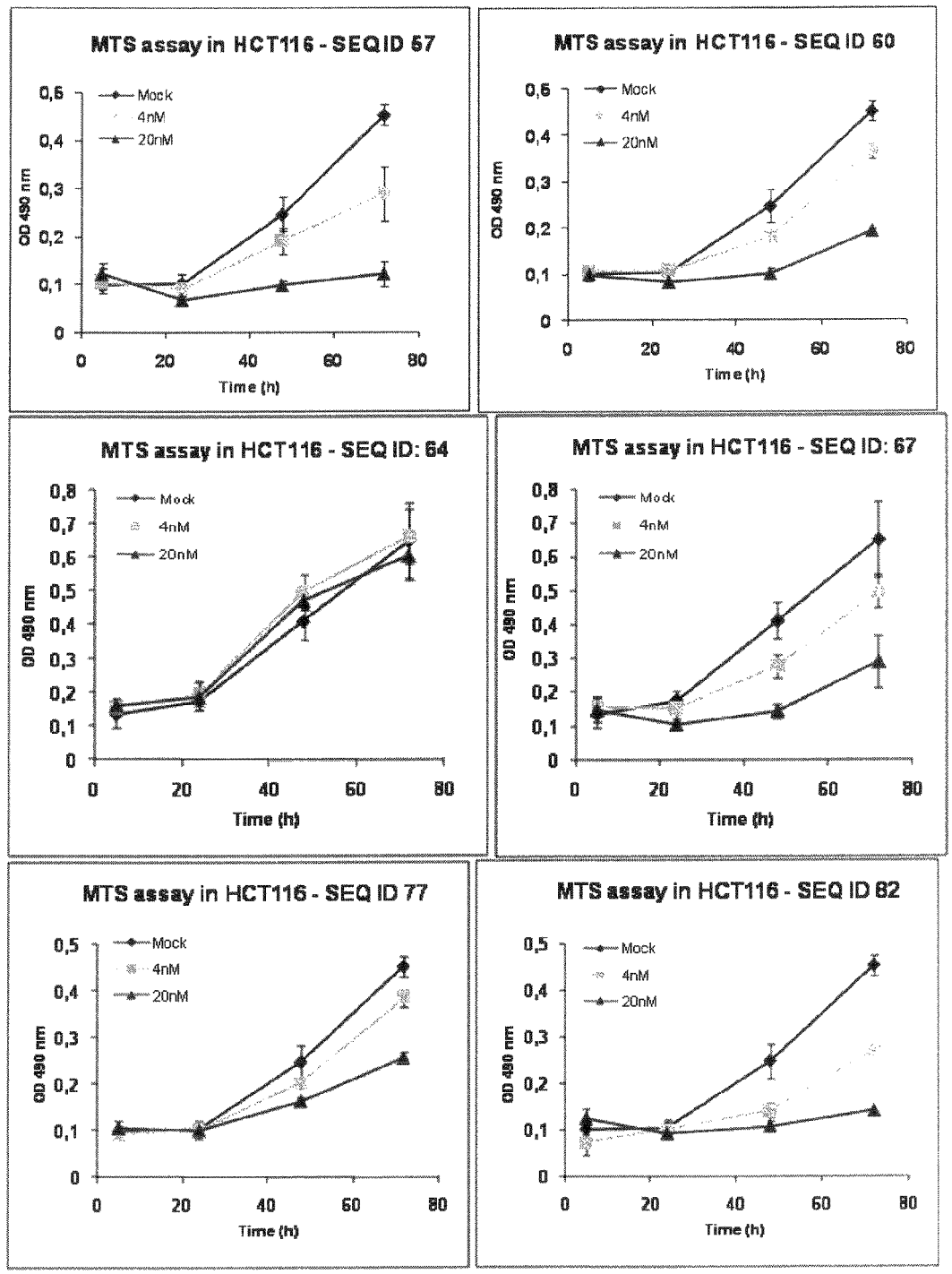
FIG. 14. Cell proliferation assay (MTS) in HCT116 cells.

MCF7 breast cancer, PC3 prostate cancer and HCT116 colon cancer cells were treated with oligonucleotides using the cationic liposome formulation LipofectAMINE 2000 (Invitrogen) as transfection vehicle. Cells were seeded in 6-well culture plates (NUNC) the day before transfection at a density of 2.5×10$^5$ cells/well (MCF7 and HCT116) or at 2.4×10$^5$ cells/well (PC3). The cells were treated when 75-90% confluent with different concentrations of oligomers. Formulation of oligomer-lipid complexes was carried out using serum-free OptiMEM (Invitrogen) and a final lipid concentration of 2.5 µg/ml (PC3), 5 µg/ml (MCF7) or 10 µg/ml (HCT116) LipofectAMINE 2000. Cells were incubated at 37° C. for 4 hours and transfection was stopped by removal of oligomer-containing culture medium. After 4 hours of treatment, media was removed and cells were trypsinized and seeded to a density of 5000 cells per well in clear 96 well plate (Scientific Orange no. 1472030100) in 100 µl media. Viable cells were measured at the times indicated by adding 10 µl of the tetrazolium compound [3-(4,5-dimethy 1-2-yl)-2-(3-carboxymethoxyphenyl)-2-(4-sulfophenyl)-2H-tetrazolium, inner salt; MTS] and an electron coupling reagent (phenazine ethosulfate; PES) (CellTiter 96® AQueous One Solution Cell Proliferation Assay, Promega). Viable cells were measured at 490 nm in a Powerwave (Biotek Instruments). The OD490 nm was plotted against time/h. (See FIGS. 11, 12 and 14). As shown in FIG. 11, oligonucleotides having the sequences of SEQ ID NOs: 57, 60, 64, 67, 77 and 82 inhibited proliferation of the breast cancer cell line MCF7, while none of the oligonucleotides had any pronounced effect on proliferation of PC3 cells (FIG. 12). Oligonucleotides having the sequences of SEQ ID NOs: 57, 60, 67, 77 and 82 inhibited the proliferation of HCT116 cells. The PIK3CA gene in the cell line MCF7 has the E545K hot-spot mutation and the PIK3CA gene in the HCT116 cell line has the H1047R hot-spot mutation. These hot-spot mutations are activating mutations. As a result, MCF7 and HCT116 cells are more sensitive to changes in PIK3CA signalling than the PC3 cell line, which has no reported hot-spot mutation in the PIK3CA gene.

Example 10

In Vitro Analysis

Effect on Caspase-3/7 Induction after Antisense Inhibition of PIK3CA in Human Cancer Cell Lines PC3 prostate cancer and HCT116 colon cancer cells were treated with oligonucleotides using the cationic liposome formulation LipofectAMINE 2000 (Invitrogen) as transfection vehicle. Cells were seeded in 6-well culture plates (NUNC) the day before transfection at a density of 2.5×$10^5$cells/well (MCF7 and HCT116) or of 2.4×$10^5$cells/well (PC3). The cells were treated when 75-90% confluent with different concentrations of oligomers. Formulation of oligomer-lipid complexes was carried out using serum-free Opti-MEM (Invitrogen) and a final lipid concentration of 2.5 µg/ml (PC3) or 10 µg/ml (HCT116) LipofectAMINE 2000. Cells were incubated at 37° C. for 4 hours and transfection was stopped by removal of oligomer-containing culture medium.

Figure 13:
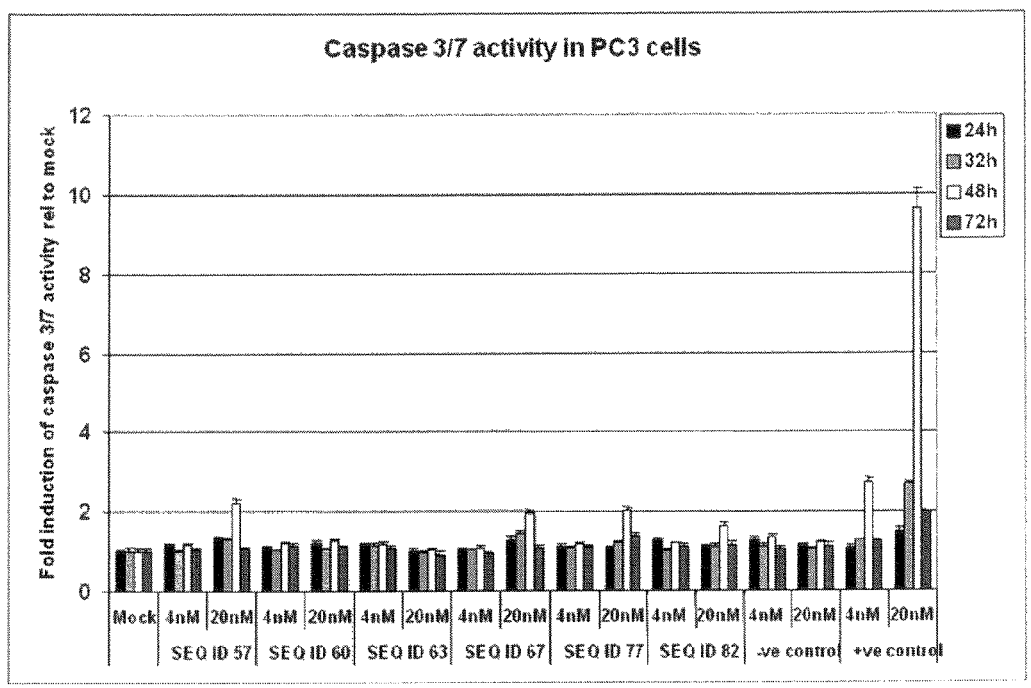
FIG. 13. Caspase 3/7 activity in PC3 cells after transfection with PIK3CA oligonucleotides. Data are expressed as fold induction compared to mock.

After 4 hours of treatment, media was removed and cells were trypsinized and seeded to a density of 5000 cells per well in white 96 well plate (NUNC) in 100 µl media. Caspase 3/7 activity was measured at the times indicated by adding 100 µl Caspase-Glo 3/7 assay (Promega). Caspase 3/7 activity was measured using a luminometer. The caspase 3/7 activities were measured at four different time points 24 h, 32 h, 48 h and 72 h (See FIG. 13 and FIG. 15). The oligomers having the sequences of SEQ ID NOs: 57, 67, 77 and 82 showed dose-dependent induction in Caspase 3/7 activity in HCT116 cells, which has a PIK3CA gene have the H1047R hot-spot mutation (FIG. 15), while the oligonucleotides had no effect on caspase 3/7 induction in PC3 cells (which have no reported hot-spot mutation in the PIK3CA gene).

Example 11

In Vitro Analysis

Biostability of PIK3CA Oligonucleotides in Mouse Plasma

Mouse plasma (Lithium heparin plasma fromBomTac:N-MRI mice, collected 14-09-05, Taconic Europe) was defrosted and aliquoted into tubes with 45·1 plasma/tube. Following this step, 5·1 oligomer (200·M) was added to the 45·1 plasma to a final concentration of 20·M. After thorough mixing, the samples were incubated at 37° C. for 0-120 ms. At different time points (0 h, 24 h, 48 h and 120 h) samples were collected and the reaction was quenched by snap freezing the samples in liquid nitrogen. For analysis, loading buffer was added to the samples, which ere then analysed by electrophoresis on a PAGE-sequencing gel under denaturing conditions. The oligonucleotides of the invention showed high plasma stability for up to 120 hrs, as shown in FIG. 16.

Example 12

In Vitro Analysis

Tm Measurement of PIK3CA Oligonucleotides Against Complementary RNA

The melting temperature of antisense oligomer/RNA duplexes was determined using a UV-spectrometry system with corresponding software (Perkin Elmer, Fremont, USA). The LNA oligomer and RNA comprising a fully-complementary target region were added in final concentrations of 1.5·M to the $T_m$-buffer (200 nM NaCl, 0.2 nM EDTA, 20 mM NaP, pH 7.0). Duplex formation was effected by heating the samples to 95° C. for 3 min followed by cooling at room temperature for 30 min.

Melting temperature ($T_m$) values were measured in a Lambda 25 UV/VIS spectrometer (Perkin Elmer) and data were collected and analysed using the TempLab software (Perkin Elmer). The instrument was programmed to heat the oligomer/RNA duplex sample from 20-95° C. and afterwards cooling the sample to 25° C. During this process the absorbance at 260 nm was recorded. The melting curves were used to calculate $T_m$ values.

The Tm values for SEQ ID NO: 57, 60, 64, 67, 77 and 82 are presented in FIG. 17.

Example 13

In Vitro Analysis

Down-Regulation of PIK3CA and pAkt in A549 Cells

A549 cells were transfected with 30 nM of LNA and cultured for 24 h. WB: 24 h, 20 ug protein/lane, 8% gel. Significant reduction of PIK3CA level was seen after transfection of A549 cells with PIK3CA LNAs. (FIG. 18) Reduction of pAkt levels was also observed 24 h post transfection. (FIG. 18). Transfection with the oligomer having the sequence of SEQ ID NO: 60 had less effect on downstream signals compared to the other tested LNAs.

Example 14

In Vitro Analysis

Down-Regulation of PIK3CA and pAkt in 15PC3 Cells

15PC3 cell were transfected with 30 nM of LNA or treated with LY294200 (a small molecule PI3K inhibitor) for 24 and 48 h. WB: 48 h, 15 ug protein/lane, 8% gel. Significant reduction of PIK3CA levels was observed after transfection of 15PC3 cells with PIK3CA LNAs. (FIG. 19) pAkt levels were reduced up to 80% at 24 h post transfection determined by ELISA. (FIG. 19). Transfection with the oligomer having the sequence of SEQ ID NO: 82 had less effect on downstream signals compared to the other tested LNAs.

Example 15

In Vivo Analysis

Figure 21:
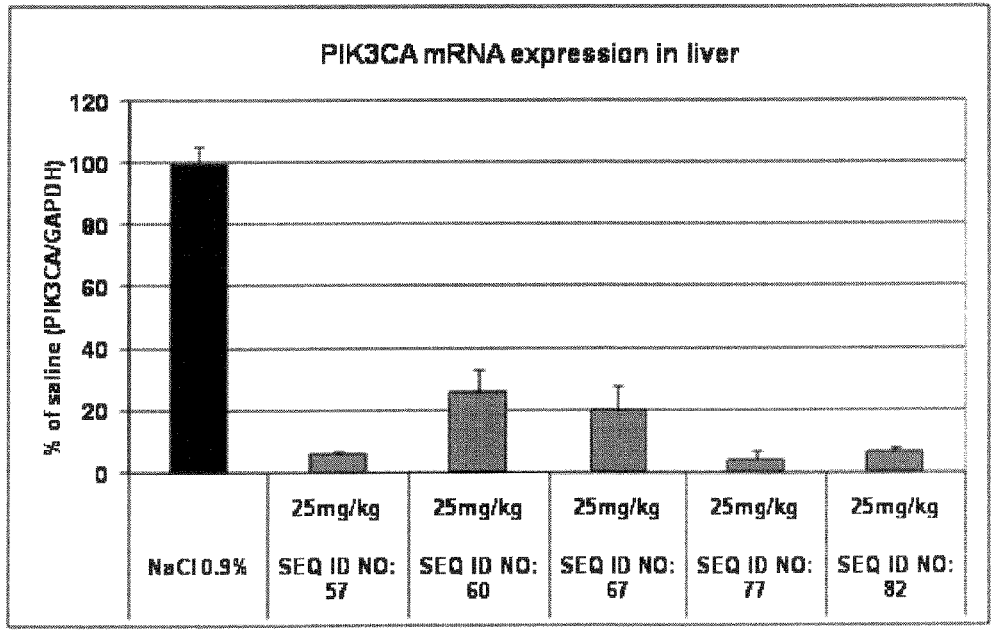
FIG. 21. In vivo knock down of PIK3CA mRNA in mouse liver. Data are expressed as % down-regulation compared to saline (100%)±stdev. There were 5 animals in each group.

Down-Regulation of Mouse PIK3CA in Mouse Liver after i.v. Administration of PIK3CA Oligonucleotides Female NMRI mice received i.v. injection of oligonucleotides having the sequences of SEQ ID NO: 57, 60, 67, 77 and 82 on three consecutive days at a dosage of 25 mg/kg. Animals were sacrificed 24 h after last dosing. The liver was stored in RNAlater stabilizing solution until use. Total RNA was extracted from liver tissue and PIK3CA mRNA levels were analyzed with qPCR. Data were compared to PIK3CA expression in saline treated control animals. As shown in FIG. 21, all oligonucleotides in the study showed potent down-regulation of PIK3CA mRNA.

All PIK3CA oligomers used in the second screening showed potent downregulation of PIK3CA in PC3 and MCF7 cells with $IC_{50}$ values below 1 nM. SEQ ID NO: 82 also shows down-regulation of the control target beta-catenin gene in both MCF7 and PC3 cells (SEQ ID NO: 82 has 2 mismatches when compared to the reverse complement of the best-aligned target region of beta-catenin).

Example 16

In Vivo Analysis

Effect of Oligomers on Lung Cancer Tumor Size in Mice

Figure 20:
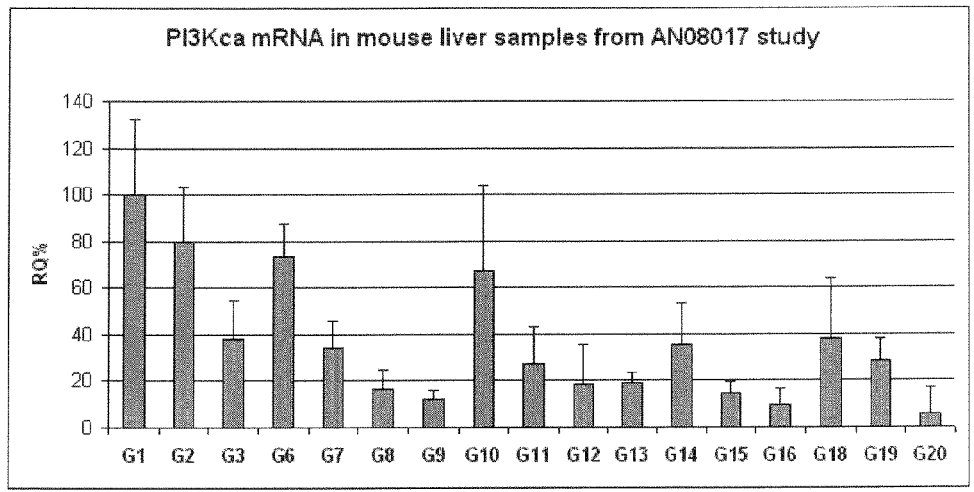
FIG. 20. Analysis of knock down of PIK3CA mRNA in liver.

Six- to seven-week old male athymic nu/nu mice (Harlan Sprague Dawley) weighing an average of 27.3±2.4 g were used in the study. Five million cells of Calu-6 (lung cancer cell line) were suspended in PBS (Gibco#14190) were injected subcutaneously into each mouse. The mice were injected with two hundred µl of oligomer intravenously when the average tumor size reached 150 mm³. Oligomers were given every 3 days for a total of 5 dosings. The control vehicles were given the same dosing regimen as the oligomers. The tumor volumes for each mouse were determined by measuring two dimensions with calipers and calculated using the formula: tumor volume=(length×width)/2). FIG. 20 shows down regulation of PIK3CA expression in liver by oligomers of the invention.

The following oligomers were found to have a good toxicity profile in terms of good animal survival in in vivo experiments at 3 mg/kg dose—SEQ IDs 60, 67, 77 & 82. SEQ IDs 60, 67 and 77 showed a good toxicity profile at 10 mg/kg dosage.

TABLE 6

Effect of oligomers on PIK3CA mRNA in mouse liver and tumor and on tumor size

| Group | Dose (mg/kg) | Tumor KD | Liver KD | TGI on day 12 (%) |
|---|---|---|---|---|
| Control | — | ND | — | — |
| SEQ ID 57 | 3 | ND | 20 ± 23 | 22.9 |
|  | 10 | ND | 62 ± 16 | 18.0 |
| SEQ ID 60 | 3 | ND | 27 ± 14 | 24.7 |
|  | 10 | ND | 66 ± 11 | 53.6 |
|  | 30 | ND | 84 ± 8 | 49.4 |
|  | 100 | ND | 88 ± 4.0 | 54.1 |
| SEQ ID 67 | 3 | 16 ± 12 | 33 ± 37 | 50.6 |
|  | 10 | 36 ± 11 | 73 ± 16 | 50.5 |
|  | 30 | 58 ± 5.2 | 82 ± 17 | 44.5 |
|  | 100 | 65 ± 12 | 81 ± 4.2 | 31.5 |
| SEQ ID 77 | 3 | ND | 65 ± 18 | 57.6 |
|  | 10 | ND | 86 ± 5.6 | 21.2 |
|  | 30 | ND | 91 ± 6.9 | 48.5 |
| SEQ ID 82 | 3 | ND | 62 ± 26 | 37.5 |
|  | 10 | ND | 72 ± 10 | 50.0 |

Example 17

Preparation of Conjugates of Oligomers with Polyethylene Glycol

The oligomers having sequences shown as SEQ ID NO: 60 (IA) or SEQ ID NO: 87 (IB) are functionalized on the 5' terminus by attaching an aminoalkyl group, such as hexan-1-amine blocked with a blocking group such as Fmoc to the 5' phosphate groups of the oligomers using routine phosphoramidite chemistry, oxidizing the resultant compounds, deprotecting them and purifying them to achieve the functionalized oligomers, respectively, having the formulas (IA) and (IB):

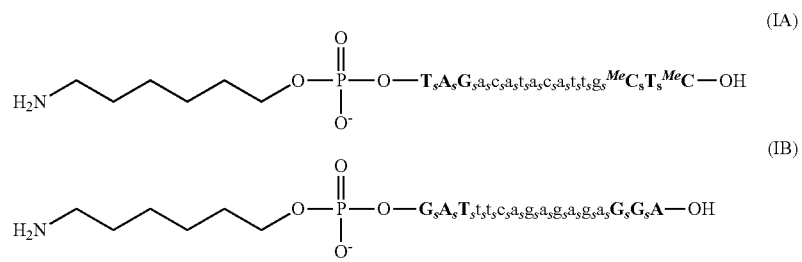

wherein the bold uppercase letters represent nucleoside analogue monomers, lowercase letters represent DNA monomers, the subscript "s" represents a phosphorothioate linkage, and $^{Me}C$ represents 5-methylcytosine.

A solution of activated PEG, such as the one shown in formula (II):

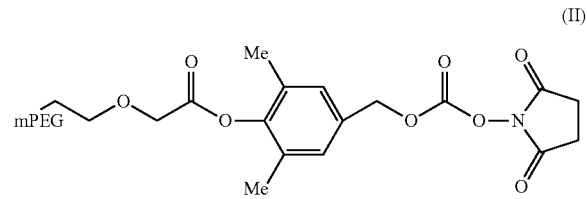

wherein the PEG moiety has an average molecular weight of 12,000, and each of the compounds of formulas (IA) and (IB) in PBS buffer are stirred in separate vessels at room temperature for 12 hours. The reaction solutions are extracted three times with methylene chloride and the combined organic layers are dried over magnesium sulphate and filtered and the solvent is evaporated under reduced pressure. The resulting residues are dissolved in double distilled water and loaded onto an anion exchange column. Unreacted PEG linker is eluted with water and the products are eluted with $NH_4HCO_3$ solution. Fractions containing pure products are pooled and lypophilized to yield the conjugates SEQ ID NOs: 60 and 87, respectively as show in formulas (IIIA) and (IIIB):

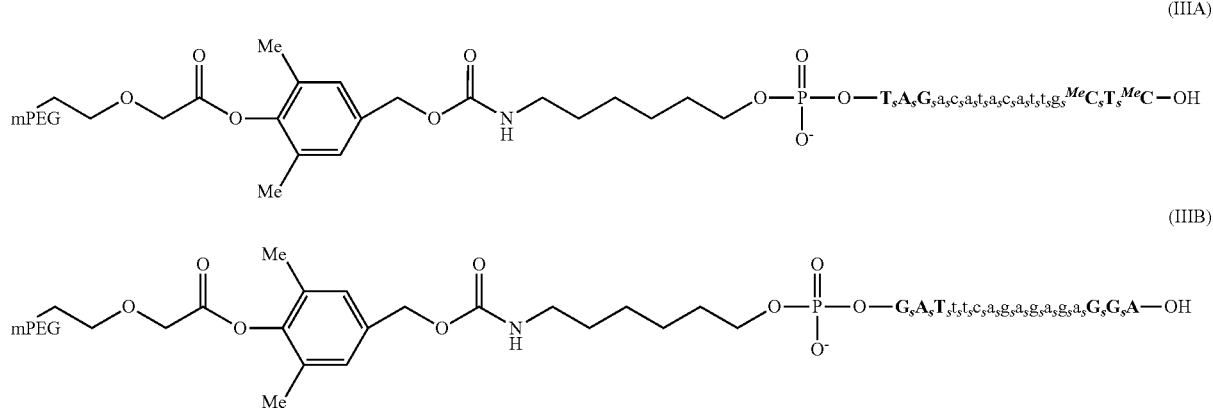

wherein each of the oligomers of SEQ ID NOs: 60 and 87 is attached to a PEG polymer having average molecular weight of 12,000 via a releasable linker.

Chemical structures of PEG polymer conjugates that can be made with oligomers having sequences shown in SEQ ID NOs: 67, 77 and 82 using the process described above are respectively shown in formulas (IVA), (IVB) and (IVC):

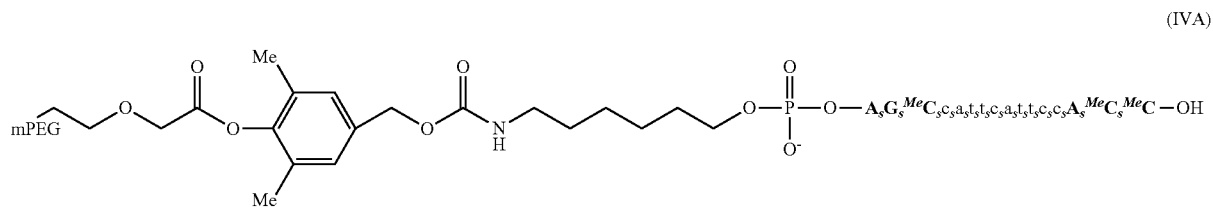

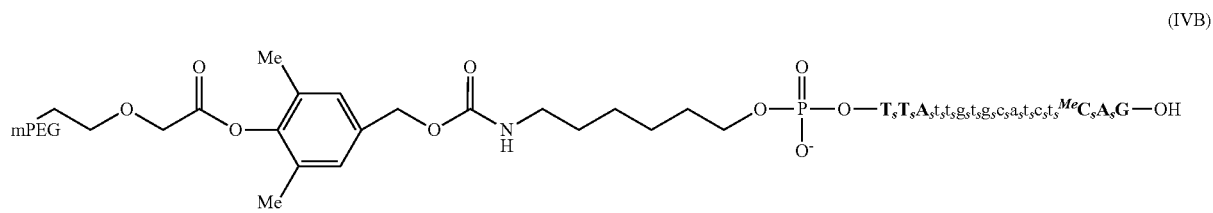

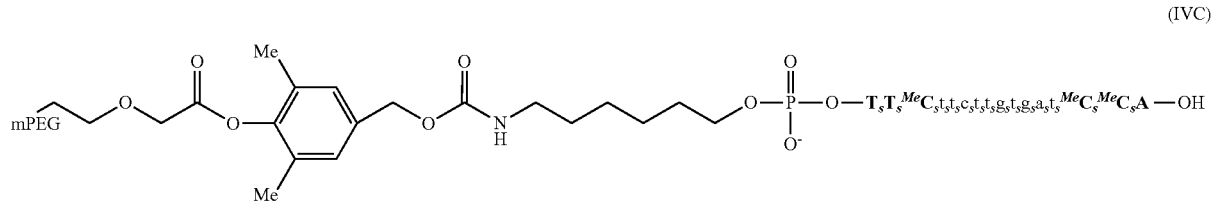

wherein bold uppercase letters represent beta-D-oxy-LNA monomers, lowercase letters represent DNA monomers, the subscript "s" represents a phosphorothioate linkage and $^{Me}C$ represent 5-methylcytosine.

Activated oligomers that can be used in this process to respectively make the conjugates shown in formulas (IVA) (SEQ ID NO: 67), (IVB) (SEQ ID NO: 77) and (IVC) (SEQ ID NO: 82) have the chemical structures shown in formulas (VA), (VB) and (VC):

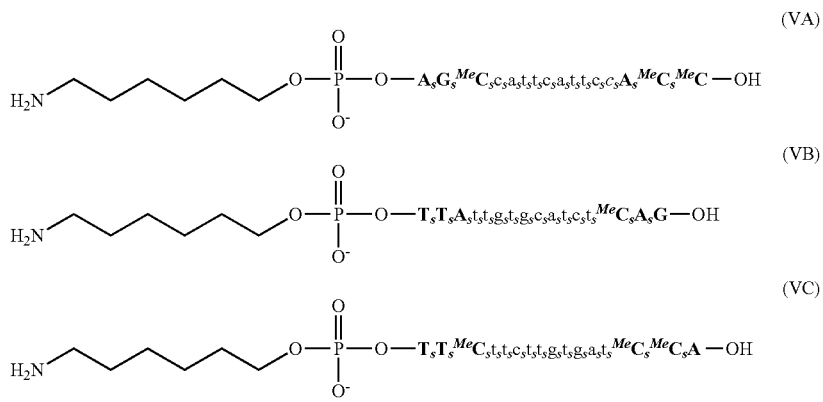

I claim:

1. A method of inhibiting the expression of PIK3CA in a cell, comprising contacting said cell with an effective amount of an oligomer, wherein the oligomer has the formula:

5' $A_sG_s{}^{Me}C_sc_sa_st_st_sc_sa_st_st_sc_sc_sA_s{}^{Me}C_s{}^{Me}C$-3' (SEQ ID NO: 67); or

5'-$T_sT_sA_st_st_sg_st_sg_sc_sa_st_sc_st_s{}^{Me}C_sA_sG$-3' (SEQ ID NO: 77), wherein uppercase letters denote beta-D-oxy-LNA monomers and lowercase letters denote DNA monomers, the subscript "s" denotes a phosphorothioate linkage, and $^{Me}C$ denotes a beta-D-oxy-LNA monomer containing a 5-methyl cytosine base.

2. A method of inhibiting the expression of PIK3CA in a cell, comprising contacting said cell with an effective amount of a conjugate, wherein the conjugate comprises the oligomer of claim 1 covalently attached to at least one moiety that is not a nucleic acid or a monomer.

3. A method of inhibiting the expression of PIK3CA in a tissue of a mammal, comprising contacting said tissue with an effective amount of an oligomer, wherein the oligomer has the formula:

5' $A_sG_s{}^{Me}C_sc_sa_st_st_sc_sa_st_st_sc_sc_sA_s{}^{Me}C_s{}^{Me}C$-3' (SEQ ID NO: 67); or

5'-$T_sT_sA_st_st_sg_st_sg_sc_sa_st_sc_st_s{}^{Me}C_sA_sG$-3' (SEQ ID NO: 77), wherein uppercase letters denote beta-D-oxy-LNA monomers and lowercase letters denote DNA monomers, the subscript "s" denotes a phosphorothioate linkage, and $^{Me}C$ denotes a beta-D-oxy-LNA monomer containing a 5-methyl cytosine base.

4. A method of inhibiting the expression of PIK3CA in a tissue of a mammal comprising contacting said tissue with an effective amount of a conjugate, wherein the conjugate comprises the oligomer of claim 3 covalently attached to at least one moiety that is not a nucleic acid or a monomer.

5. A method of inhibiting the expression of PIK3CA and beta-catenin in a cell or tissue of a mammal, comprising contacting said cell or tissue with an effective amount of an oligomer, wherein the oligomer has the formula:

5' $A_sG_s{}^{Me}C_sc_sa_st_st_sc_sa_st_st_sc_sc_sA_s{}^{Me}C_s{}^{Me}C$-3' (SEQ ID NO: 67); or

5'-$T_sT_sA_st_st_sg_st_sg_sc_sa_st_sc_st_s{}^{Me}C_sA_sG$-3' (SEQ ID NO: 77), wherein uppercase letters denote beta-D-oxy-LNA monomers and lowercase letters denote DNA monomers, the subscript "s" denotes a phosphorothioate linkage, and $^{Me}C$ denotes a beta-D-oxy-LNA monomer containing a 5-methylcytosine base.

6. A method of inhibiting the expression of PIK3CA and beta-catenin in a tissue of a mammal comprising contacting said tissue with an effective amount of a conjugate, wherein the conjugate comprises the oligomer of claim 5 covalently attached to at least one moiety that is not a nucleic acid or a monomer.

7. A method of treating cancer in a mammal, comprising administering to said mammal an effective amount of an oligomer, wherein the oligomer has the formula:

5' $A_s G_s{}^{Me}C_s c_s a_s t_s t_s c_s a_s t_s t_s c_s c_s A_s{}^{Me}C_s{}^{Me}C$-3' (SEQ ID NO: 67); or

5'-$T_s T_s A_s t_s t_s g_s t_s g_s c_s a_s t_s c_s t_s{}^{Me}C_s A_s G$-3' (SEQ ID NO: 77), wherein uppercase letters denote beta-D-oxy-LNA monomers and lowercase letters denote DNA monomers, the subscript "s" denotes a phosphorothioate linkage, and $^{Me}C$ denotes a beta-D-oxy-LNA monomer containing a 5-methylcytosine base.

8. The method of claim 7, wherein the cancer is selected from the group consisting of non-Hodgkin's lymphoma, Hodgkin's lymphoma, acute lymphocytic leukemia, acute myelocytic leukemia, chronic myeloid leukemia, chronic lymphocytic leukemia, multiple myeloma, colon cancer, rectal carcinoma, pancreatic cancer, breast cancer, ovarian cancer, prostate cancer, renal cell carcinoma, hepatoma, bile duct carcinoma, choriocarcinoma, cervical cancer, testicular cancer, lung cancer, bladder carcinoma, melanoma, head and neck cancer, brain cancer, neoplasms, cancers of the peripheral nervous system, cancers of the central nervous system, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, seminoma, embryonal carcinoma, Wilms' tumor, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, and retinoblastoma, heavy chain disease.

9. The method of claim 8, wherein the cancer is breast cancer or prostate cancer.

10. An oligomer of the formula:

5'-$T_s T_s A_s t_s t_s g_s t_s g_s c_s a_s t_s c_s t_s{}^{Me}C_s A_s G$-3' (SEQ ID NO: 77), wherein uppercase letters denote beta-D-oxy-LNA monomers and lowercase letters denote DNA monomers, the subscript "s" denotes a phosphorothioate linkage, and $^{Me}C$ denotes a beta-D-oxy-LNA monomer containing a 5-methylcytosine base.

11. A conjugate comprising the oligomer of claim 10 covalently attached to at least one moiety that is not a nucleic acid or a monomer.

12. A pharmaceutical composition comprising the oligomer of claim 10, and a pharmaceutically acceptable diluents, carrier, salt or adjuvant.

13. An activated oligomer comprising the oligomer of claim 10 and least one functional group covalently attached thereto at one or more positions independently selected from the 5'-end, the 3'-end, the 2'-OR of a ribose sugar, and the base.

14. A pharmaceutical composition comprising the conjugate of claim 11, and a pharmaceutically acceptable diluents, carrier, salt or adjuvant.

* * * * *

UNITED STATES PATENT AND TRADEMARK OFFICE
CERTIFICATE OF CORRECTION

| | | |
|---|---|---|
| PATENT NO. | : 8,450,291 B2 | Page 1 of 1 |
| APPLICATION NO. | : 12/947865 | |
| DATED | : May 28, 2013 | |
| INVENTOR(S) | : Maj Hedtjarn | |

It is certified that error appears in the above-identified patent and that said Letters Patent is hereby corrected as shown below:

In the Claims

Col. 150, line 25, claim 13, delete "2'-OR" and insert -- 2'-OH --

Signed and Sealed this
Seventeenth Day of June, 2014

Michelle K. Lee
*Deputy Director of the United States Patent and Trademark Office*

SEQUENCE LISTING

<160> NUMBER OF SEQ ID NOS: 160

<210> SEQ ID NO 1
<211> LENGTH: 3724
<212> TYPE: DNA
<213> ORGANISM: homo sapiens

<400> SEQUENCE: 1

```
tctccctcgg cgccgccgcc gccgcccgcg gggctgggac ccgatgcggt tagagccgcg      60
gagcctggaa gagccccgag cgtttctgct ttgggacaac catacatcta attccttaaa     120
gtagttttat atgtaaaact tgcaagaat cagaacaatg cctccacgac catcatcagg     180
tgaactgtgg ggcatccact tgatgccccc aagaatccta gtagaatgtt tactaccaaa     240
tggaatgata gtgactttag aatgcctccg tgaggctaca ttaataacca taaagcatga     300
actatttaaa gaagcaagaa aataccccct ccatcaactt cttcaagatg aatcttctta     360
cattttcgta agtgttactc aagaagcaga aagggaagaa ttttttgatg aaacaagacg     420
actttgtgac cttcggcttt ttcaacccct tttaaagta attgaaccag taggcaaccg     480
tgaagaaaag atcctcaatc gagaaattgg ttttgctatc ggcatgccag tgtgtgaatt     540
tgatatggtt aaagatccag aagtacagga cttccgaaga aatattctga acgtttgtaa     600
agaagctgtg gatcttaggg acctcaattc acctcatagt agagcaatgt atgtctatcc     660
tccaaatgta gaatcttcac cagaattgcc aaagcacata tataataaat tagataaagg     720
gcaaataata gtggtgatct gggtaatagt ttctccaaat aatgacaagc agaagtatac     780
tctgaaaatc aaccatgact gtgtaccaga acaagtaatt gctgaagcaa tcaggaaaaa     840
aactcgaagt atgttgctat cctctgaaca actaaaactc tgtgttttag aatatcaggg     900
caagtatatt ttaaaagtgt gtggatgtga tgaatacttc ctagaaaaat atcctctgag     960
tcagtataag tatataagaa gctgtataat gcttgggagg atgcccaatt tgatgttgat    1020
ggctaaagaa agcctttatt ctcaactgcc aatggactgt tttacaatgc catcttattc    1080
cagacgcatt tccacagcta caccatatat gaatggagaa acatctacaa aatcccttg    1140
```

```
ggttataaat agtgcactca gaataaaaat tctttgtgca acctacgtga atgtaaatat    1200
tcgagacatt gataagatct atgttcgaac aggtatctac catggaggag aaccccttatg   1260 tgacaatgtg aacactcaaa gagtaccttg ttccaatccc aggtggaatg aatggctgaa    1320
ttatgatata tacattcctg atcttcctcg tgctgctcga ctttgccttt ccatttgctc    1380
tgttaaaggc cgaaagggtg ctaaagagga acactgtcca ttggcatggg aaatataaa    1440 cttgtttgat tacacagaca ctctagtatc tggaaaaatg ctttgaatc tttggccagt     1500 acctcatgga ttagaagatt tgctgaaccc tattggtgtt actggatcaa atccaaataa   1560
agaaactcca tgcttagagt tggagtttga ctggttcagc agtgtggtaa agttcccaga   1620
tatgtcagtg attgaagagc atgccaattg gtctgtatcc cgagaagcag gatttagcta   1680
ttcccacgca ggactgagta acagactagc tagagacaat gaattaaggg aaaatgacaa   1740
agaacagctc aaagcaattt ctacacgaga tcctctctct gaaatcactg agcaggagaa   1800
agattttcta tggagtcaca gacactattg tgtaactatc cccgaaattc tacccaaatt   1860
gcttctgtct gttaaatgga attctagaga tgaagtagcc cagatgtatt gcttggtaaa   1920
agattggcct ccaatcaaac ctgaacaggc tatggaactt ctggactgta attacccaga   1980
tcctatggtt cgaggttttg ctgttcggtg cttggaaaaa tatttaacag atgacaaact   2040
ttctcagtat ttaattcagc tagtacaggt cctaaaatat gaacaatatt tggataactt   2100
gcttgtgaga tttttactga agaaagcatt gactaatcaa aggattgggc acttttctct   2160 ttggcatttta aaatctgaga tgcacaataa acagttagc cagaggtttg gcctgctttt    2220
ggagtcctat tgtcgtgcat gtgggatgta tttgaagcac ctgaataggc aagtcgaggc   2280
aatggaaaag ctcattaact taactgacat tctcaaacag gagaagaagg atgaaacaca   2340
aaaggtacag atgaagtttt tagttgagca aatgaggcga ccagatttca tggatgctct   2400
acagggcttt ctgtctcctc taaaccctgc tcatcaacta ggaaacctca ggcttgaaga   2460
gtgtcgaatt atgtcctctg caaaaaggcc actgtggttg aattgggaga cccagacat    2520 catgtcagag ttactgtttc agaacaatga gatcatcttt aaaaatgggg atgatttacg   2580
gcaagatatg ctaacacttc aaattattcg tattatggaa aatatctggc aaaatcaagg   2640
tcttgatctt cgaatgttac cttatggttg tctgtcaatc ggtgactgtg tgggacttat   2700
tgaggtggtg cgaaattctc acactattat gcaaattcag tgcaaaggcg gcttgaaagg   2760
tgcactgcag ttcaacagcc acacactaca tcagtggctc aaagacaaga caaaggaga   2820 aatatatgat gcagccattg acctgtttac acgttcatgt gctggatact gtgtagctac   2880
cttcattttg ggaattggag atcgtcacaa tagtaacatc atggtgaaag acgatggaca   2940
actgtttcat atagattttg gacacttttt ggatcacaag aagaaaaaat ttggttataa   3000
acgagaacgt gtgccatttg ttttgacaca ggatttctta atagtgatta gtaaaggagc   3060
ccaagaatgc acaaagacaa gagaatttga gaggtttcag gagatgtgtt acaaggctta   3120
tctagctatt cgacagcatg ccaatctctt cataaatctt ttctcaatga tgcttggctc   3180
tggaatgcca gaactacaat cttttgatga cattgcatac attcgaaaga ccctagcctt   3240
agataaaact gagcaagagg ctttggagta tttcatgaaa caaatgaatg atgcacatca   3300
tggtggctgg acaacaaaaa tggattggat cttccacaca attaaacagc atgcattgaa   3360
ctgaaaagat aactgagaaa atgaaagctc actctggatt ccacactgca ctgttaataa   3420
ctctcagcag gcaagaccg attgcatagg aattgcacaa tccatgaaca gcattagaat   3480
ttacagcaag aacagaaata aaatactata taatttaaat aatgtaaacg caaacagggt   3540
```

```
ttgatagcac ttaaactagt tcatttcaaa attaagcttt agaataatgc gcaatttcat    3600
gttatgcctt aagtccaaaa aggtaaactt tgaagattgt ttgtatcttt ttttaaaaaa    3660 caaacaaaa caaaatccc caaatatat agaaatgatg gagaaggaaa aaaaaaaaa        3720 aaaa                                                                 3724

<210> SEQ ID NO 2
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 2
gaggcattct aaagtc                                                    16

<210> SEQ ID NO 3
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 3
attcttccct ttctgc                                                    16

<210> SEQ ID NO 4
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 4
tagacataca ttgctc                                                    16

<210> SEQ ID NO 5
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 5
tacttgccct gatatt                                                    16

<210> SEQ ID NO 6
<211> LENGTH: 16
<212> TYPE: DNA
```

```
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 6
cacataaggg ttctcc                                                       16

<210> SEQ ID NO 7
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 7
agccattcat tccacc                                                       16

<210> SEQ ID NO 8
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 8
cagtaacacc aatagg                                                       16

<210> SEQ ID NO 9
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 9
aactccaact ctaagc                                                       16

<210> SEQ ID NO 10
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 10
cagacagaag caattt                                                       16
```

```
<210> SEQ ID NO 11
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 11
ttattgtgca tctcag                                                         16

<210> SEQ ID NO 12
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 12
gcagaggaca taattc                                                         16

<210> SEQ ID NO 13
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 13
gatgtctggg ttctcc                                                         16

<210> SEQ ID NO 14
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 14
ttcttcttgt gatcca                                                         16

<210> SEQ ID NO 15
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
```

```
                                   -continued phosphorothioate

<400> SEQUENCE: 15
aagaaatcct gtgtca                                                      16

<210> SEQ ID NO 16
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
        phosphorothioate

<400> SEQUENCE: 16
tctcctgaaa cctctc                                                      16

<210> SEQ ID NO 17
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
        phosphorothioate

<400> SEQUENCE: 17
gattttagag agagga                                                      16

<210> SEQ ID NO 18
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
        phosphorothioate

<400> SEQUENCE: 18
agtgatttta gagaga                                                      16

<210> SEQ ID NO 19
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
        phosphorothioate

<400> SEQUENCE: 19
tcctgcttag tgattt                                                      16

<210> SEQ ID NO 20
<211> LENGTH: 16
<212> TYPE: DNA
<213> ORGANISM: artificial
<220> FEATURE:
```

```
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 20
ttctcctgct tagtga                                                     16

<210> SEQ ID NO 21
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 21
gccaccatga cgtgca                                                     16

<210> SEQ ID NO 22
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 22
accatgacgt gcatca                                                     16

<210> SEQ ID NO 23
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 23
gatttcagag agagga                                                     16

<210> SEQ ID NO 24
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 24
agtgatttca gagaga                                                     16
```

-continued

```
<210> SEQ ID NO 25
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 25
tcctgctcag tgattt                                                    16

<210> SEQ ID NO 26
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 26
ttctcctgct cagtga                                                    16

<210> SEQ ID NO 27
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 27
gccaccatga tgtgca                                                    16

<210> SEQ ID NO 28
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate

<400> SEQUENCE: 28
accatgatgt gcatca                                                    16

<210> SEQ ID NO 29
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 29
```

-continued gaggcattct aaagtc                                                      16

<210> SEQ ID NO 30
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 30
attcttccct ttctgc                                                      16

<210> SEQ ID NO 31
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 31
tagacataca ttgctc                                                      16

<210> SEQ ID NO 32
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 32
tacttgccct gatatt                                                      16

<210> SEQ ID NO 33
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 33
cacataaggg ttctcc                                                      16

<210> SEQ ID NO 34
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 34

```
agccattcat tccacc                                              16
```

<210> SEQ ID NO 35
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 35

```
cagtaacacc aatagg                                              16
```

<210> SEQ ID NO 36
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 36

```
aactccaact ctaagc                                              16
```

<210> SEQ ID NO 37
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 37

```
cagacagaag caattt                                              16
```

<210> SEQ ID NO 38
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 38

```
ttattgtgca tctcag                                              16
```

<210> SEQ ID NO 39
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 39
gcagaggaca taattc                                                      16

<210> SEQ ID NO 40
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 40
gatgtctggg ttctcc                                                      16

<210> SEQ ID NO 41
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 41
ttcttcttgt gatcca                                                      16

<210> SEQ ID NO 42
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 42
aagaaatcct gtgtca                                                      16

<210> SEQ ID NO 43
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 43
tctcctgaaa cctctc                                                      16

<210> SEQ ID NO 44
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 44

```
gattttagag agagga                                                    16

<210> SEQ ID NO 45
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 45 agtgattta gagaga                                                     16

<210> SEQ ID NO 46
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 46
tcctgcttag tgattt                                                    16

<210> SEQ ID NO 47
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 47
ttctcctgct tagtga                                                    16

<210> SEQ ID NO 48
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 48
gccaccatga cgtgca                                                    16

<210> SEQ ID NO 49
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 49
```

```
accatgacgt gcatca                                                    16

<210> SEQ ID NO 50
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 50
gatttcagag agagga                                                    16

<210> SEQ ID NO 51
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 51
agtgatttca gagaga                                                    16

<210> SEQ ID NO 52
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 52
tcctgctcag tgattt                                                    16

<210> SEQ ID NO 53
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 53
ttctcctgct cagtga                                                    16

<210> SEQ ID NO 54
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 54
```
gccaccatga tgtgca                                                            16

<210> SEQ ID NO 55
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 Gapmer - optionally phosphorothioate

<400> SEQUENCE: 55
accatgatgt gcatca                                                            16

<210> SEQ ID NO 56
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 56
gaggcattct aaagtc                                                            16

<210> SEQ ID NO 57
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 57
attcttccct ttctgc                                                            16

<210> SEQ ID NO 58
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 58
ttcttccctt tctg                                                              14

<210> SEQ ID NO 59
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 59
tcttcccttt ct                                                    12

<210> SEQ ID NO 60
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 60
tagacataca ttgctc                                                16

<210> SEQ ID NO 61
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 61
agacatacat tgct                                                  14

<210> SEQ ID NO 62
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 62
gacatacatt gc                                                    12

<210> SEQ ID NO 63
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 63
tacttgccct gatatt                                                16

<210> SEQ ID NO 64
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 64
cacataaggg ttctcc                                              16

<210> SEQ ID NO 65
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 65
acataagggt tctc                                                14

<210> SEQ ID NO 66
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 66
cataagggtt ct                                                  12

<210> SEQ ID NO 67
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 67
agccattcat tccacc                                              16

<210> SEQ ID NO 68
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 68
gccattcatt ccac                                                14

<210> SEQ ID NO 69
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 69
ccattcattc ca                                                    12

<210> SEQ ID NO 70
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 70
cagtaacacc aatagg                                                16

<210> SEQ ID NO 71
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 71
agtaacacca atag                                                  14

<210> SEQ ID NO 72
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 72
gtaacaccaa ta                                                    12

<210> SEQ ID NO 73
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 73
aactccaact ctaagc                                                16

<210> SEQ ID NO 74
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 74
cagacagaag caattt                                                16

<210> SEQ ID NO 75
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 75
agacagaagc aatt                                                  14

<210> SEQ ID NO 76
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 76
gacagaagca at                                                    12

<210> SEQ ID NO 77
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 77
ttattgtgca tctcag                                                16

<210> SEQ ID NO 78
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 78
tattgtgcat ctca                                                  14

<210> SEQ ID NO 79
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 79

-continued attgtgcatc tc                                                       12

<210> SEQ ID NO 80
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 80
gcagaggaca taattc                                                   16

<210> SEQ ID NO 81
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 81
gatgtctggg ttctcc                                                   16

<210> SEQ ID NO 82
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 82
ttcttcttgt gatcca                                                   16

<210> SEQ ID NO 83
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 83
tcttcttgtg atcc                                                     14

<210> SEQ ID NO 84
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 84
cttcttgtga tc                                                         12

<210> SEQ ID NO 85
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 85
aagaaatcct gtgtca                                                     16

<210> SEQ ID NO 86
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 86
tctcctgaaa cctctc                                                     16

<210> SEQ ID NO 87
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 87
gatttcagag agagga                                                     16

<210> SEQ ID NO 88
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 88
atttcagaga gagg                                                       14

<210> SEQ ID NO 89
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 89

-continued

```
tttcagagag ag                                                          12

<210> SEQ ID NO 90
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 90
agtgatttca gagaga                                                      16

<210> SEQ ID NO 91
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 91
gtgatttcag agag                                                        14

<210> SEQ ID NO 92
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 92
tgatttcaga ga                                                          12

<210> SEQ ID NO 93
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 93
tcctgctcag tgattt                                                      16

<210> SEQ ID NO 94
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 94
```

```
ttctcctgct cagtga                                                    16

<210> SEQ ID NO 95
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 95
gccaccatga tgtgca                                                    16

<210> SEQ ID NO 96
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 96
accatgatgt gcatca                                                    16

<210> SEQ ID NO 97
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-9-2 LNA Gapmer - fully phosphorothioate

<400> SEQUENCE: 97
ccatgatgtg catc                                                      14

<210> SEQ ID NO 98
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 98
catgatgtgc at                                                        12

<210> SEQ ID NO 99
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 99
```
gattttagag agagga                                                     16

<210> SEQ ID NO 100
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 100
agtgatttta gagaga                                                     16

<210> SEQ ID NO 101
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 101
tcctgcttag tgattt                                                     16

<210> SEQ ID NO 102
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 102
ttctcctgct tagtga                                                     16

<210> SEQ ID NO 103
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 103
gccaccatga cgtgca                                                     16

<210> SEQ ID NO 104
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: 3-10-3 LNA Gapmer - fully phosphorothioate

<400> SEQUENCE: 104

```
accatgacgt gcatca                                                    16
```

<210> SEQ ID NO 105
<211> LENGTH: 1068
<212> TYPE: PRT
<213> ORGANISM: homo sapiens

<400> SEQUENCE: 105

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

-continued

```
Asp Asn Val Asn Thr Gln Arg Val Pro Cys Ser Asn Pro Arg Trp Asn
    370                 375                 380
Glu Trp Leu Asn Tyr Asp Ile Tyr Ile Pro Asp Leu Pro Arg Ala Ala
385                 390                 395                 400
Arg Leu Cys Leu Ser Ile Cys Ser Val Lys Gly Arg Lys Gly Ala Lys
            405                 410                 415
Glu Glu His Cys Pro Leu Ala Trp Gly Asn Ile Asn Leu Phe Asp Tyr
            420                 425                 430
Thr Asp Thr Leu Val Ser Gly Lys Met Ala Leu Asn Leu Trp Pro Val
        435                 440                 445
Pro His Gly Leu Glu Asp Leu Leu Asn Pro Ile Gly Val Thr Gly Ser
    450                 455                 460
Asn Pro Asn Lys Glu Thr Pro Cys Leu Glu Leu Glu Phe Asp Trp Phe
465                 470                 475                 480
Ser Ser Val Val Lys Phe Pro Asp Met Ser Val Ile Glu Glu His Ala
            485                 490                 495
Asn Trp Ser Val Ser Arg Glu Ala Gly Phe Ser Tyr Ser His Ala Gly
            500                 505                 510
Leu Ser Asn Arg Leu Ala Arg Asp Asn Glu Leu Arg Glu Asn Asp Lys
        515                 520                 525
Glu Gln Leu Lys Ala Ile Ser Thr Arg Asp Pro Leu Ser Glu Ile Thr
    530                 535                 540
Glu Gln Glu Lys Asp Phe Leu Trp Ser His Arg His Tyr Cys Val Thr
545                 550                 555                 560
Ile Pro Glu Ile Leu Pro Lys Leu Leu Leu Ser Val Lys Trp Asn Ser
            565                 570                 575
Arg Asp Glu Val Ala Gln Met Tyr Cys Leu Val Lys Asp Trp Pro Pro
            580                 585                 590
Ile Lys Pro Glu Gln Ala Met Glu Leu Leu Asp Cys Asn Tyr Pro Asp
        595                 600                 605
Pro Met Val Arg Gly Phe Ala Val Arg Cys Leu Glu Lys Tyr Leu Thr
    610                 615                 620
Asp Asp Lys Leu Ser Gln Tyr Leu Ile Gln Leu Val Gln Val Leu Lys
625                 630                 635                 640
Tyr Glu Gln Tyr Leu Asp Asn Leu Leu Val Arg Phe Leu Leu Lys Lys
            645                 650                 655
Ala Leu Thr Asn Gln Arg Ile Gly His Phe Phe Phe Trp His Leu Lys
            660                 665                 670
Ser Glu Met His Asn Lys Thr Val Ser Gln Arg Phe Gly Leu Leu Leu
        675                 680                 685
Glu Ser Tyr Cys Arg Ala Cys Gly Met Tyr Leu Lys His Leu Asn Arg
    690                 695                 700
Gln Val Glu Ala Met Glu Lys Leu Ile Asn Leu Thr Asp Ile Leu Lys
705                 710                 715                 720
Gln Glu Lys Lys Asp Glu Thr Gln Lys Val Gln Met Lys Phe Leu Val
            725                 730                 735
Glu Gln Met Arg Arg Pro Asp Phe Met Asp Ala Leu Gln Gly Phe Leu
            740                 745                 750
Ser Pro Leu Asn Pro Ala His Gln Leu Gly Asn Leu Arg Leu Glu Glu
        755                 760                 765
Cys Arg Ile Met Ser Ser Ala Lys Arg Pro Leu Trp Leu Asn Trp Glu
    770                 775                 780
Asn Pro Asp Ile Met Ser Glu Leu Leu Phe Gln Asn Asn Glu Ile Ile
785                 790                 795                 800
```

```
Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn Leu Phe Ser Met Met Leu Gly Ser
        995                 1000                1005

Gly Met Pro Glu Leu Gln Ser Phe Asp Asp Ile Ala Tyr Ile Arg
    1010                1015                1020

Lys Thr Leu Ala Leu Asp Lys Thr Glu Gln Glu Ala Leu Glu Tyr
    1025                1030                1035

Phe Met Lys Gln Met Asn Asp Ala His His Gly Gly Trp Thr Thr
    1040                1045                1050

Lys Met Asp Trp Ile Phe His Thr Ile Lys Gln His Ala Leu Asn
    1055                1060                1065

<210> SEQ ID NO 106
<211> LENGTH: 3207
<212> TYPE: DNA
<213> ORGANISM: Mus musculus

<400> SEQUENCE: 106
atgcctccac gaccatcttc gggtgaactg tggggcatcc acttgatgcc cccacgaatc      60
ctagtggaat gtttactccc caatggaatg atagtgactt agaatgcct ccgtgaggcc     120 acactcgtca ccatcaaaca tgaactgttc agagaggcca ggaataccc tctccatcag     180 cttctgcaag acgaaacttc ttacattttc gtaagtgtca cccaagaagc agaaagggaa     240 gaatttttg atgaaacaag acgactttgt gaccttcggc ttttcaacc cttttaaaa      300 gttattgaac cagtaggcaa ccgtgaagaa aagatcctca atcgagaaat tggttttgtt     360
attggcatgc cagtgtgtga atttgatatg gttaaagatc cagaagtcca agactttcga     420
aggaacattc tgaatgtttg caaagaagct gtggacctgc gggatctcaa ctcgcctcat     480
agcagagcaa tgtatgtcta ccctccaaat gtcgagtctt ccccagaact gccaaagcac     540
atctacaaca agttagataa aggacaaatc atagtggtga tttgggtaat agtctctcca     600
```

```
aacaacgaca agcagaagta cactctgaag atcaatcatg actgtgtgcc agagcaagtc    660
attgctgaag ccatcaggaa aaagactcgg agcatgttgt tgtcctctga gcagctgaaa    720
ctctgtgtct tagaatatca gggcaagtat attctgaaag tgtgtggctg tgacgaatac    780
ttcctggaaa agtaccctct gagtcagtac aagtacataa gaagctgtat aatgctgggg    840
aggatgccca acttgatgct gatggccaaa gaaagcctat actctcagct gccgattgat    900
agcttcacca tgccgtcata ctccaggcgc atctccacag ccacacccta catgaatgga    960
gagacatcta cgaaatccct ctgggtcata aatagtgcgc tcagaataaa aattctttgt   1020
gcaacctatg taaatgtaaa tattcgagac attgataaga tctatgttcg aacaggtatc   1080
taccatggag gagaacccctt atgtgacaat gtgaacactc aaagagtacc ttgttccaat   1140
cctaggtgga atgaatggct gaattatgat atatacattc ctgatcttcc tcgtctggcg   1200
cgcctttgcc tttcaatctg ctctgttaaa ggccgaaagg gtgctaagga ggagcactgt   1260
ccgttggcct ggggaaacat aaacttgttt gattatacag acaccctagt gtccgggaaa   1320
atggctttga atctctggcc tgtaccgcat gggttagaag atctgctgaa ccctattggt   1380
gttactgggt caaatccaaa taagaaaact ccatgcttag agttggagtt tgattggttc   1440
agcagtgtgg tgaagtttcc agacatgtct gtgatcgaag aacatgccaa ttggtccgtg   1500
tcccgagaag ctggattcag ttactcccat acaggactga gtaacagact agccagagac   1560
aatgagttaa gagaaaatga caaggaacag ctccgagcac tttgcacccg ggacccacta   1620
tctgaaatca ctgaacaaga gaaagacttc ctatggagcc acagacacta ctgcgtaact   1680
attcctgaaa tcctacccaa attgcttctg tctgtcaagt ggaattccag agacgaagtg   1740
gcccagatgt actgcttagt aaaagattgg cctccaatca aaccagagca agccatggaa   1800
ctcctggact gtaactatcc agatcctatg gttcggagtt ttgctgttcg gtgcttagaa   1860
aaatatttaa cagatgacaa actttctcag tacctcattc aacttgtaca ggtcttaaaa   1920
tatgaacagt atttggataa cctgcttgtg agatttttac tcaagaaagc attgacaaat   1980
caaaggattg gccattttt cttttggcat ttaaaatctg agatgcacaa taagactgtc   2040
agtcagaggt ttggcctgct attggagtcc tactgccgtg cctgtgggat gtatctgaag   2100
cacctgaaca gacaagtaga ggccatggag aagctcatca acctaacgga catccttaag   2160
caggagaaga aggatgagac acaaaaggta cagatgaagt ttttggttga acagatgaga   2220
cagccagact tcatggatgc tttgcagggt tttctgtccc ctctgaatcc tgctcaccaa   2280
ctaggaaacc tcaggcttga agagtgtcga attatgtcct ctgcaaaaag gccactgtgg   2340
ttgaattggg agaacccaga catcatgtca gagctactgt ttcagaacaa tgagatcatc   2400
tttaaaaatg gcgacgactt acggcaagat atgttaaccc ttcagatcat ccgaatcatg   2460
gagaacatct ggcaaaacca aggccttgac cttcgcatgc taccttatgg ctgtctatcc   2520 attgggact gtgtgggtct catcgaggtg gtgagaaact ctcacaccat catgcaaatc   2580
cagtgcaaag gaggcctgaa gggggcgctg cagttcaaca gccacacact gcatcaatgg   2640
ctcaaggaca gaacaagggg cgagatatat gatgcagcca ttgacctgtt cactcggtcc   2700
tgcgctgggt actgcgtggc aacctttatc ttgggaattg gagaccggca acagcaac     2760 atcatggtga agatgacgg acagctgttt catatagatt tgggcactt tttggatcac   2820 aagaagaaaa aatttggcta taagcgggaa cgtgtgccat ttgtgttgac acaggatttc   2880
ttgattgtga ttagtaaggg agcacaagag tacaccaaga ccagagagtt tgagaggttt   2940
caggagatgt gttacaaggc ttacctagca attcggcagc atgccaatct cttcatcaac   3000
```

```
ctttttttcaa tgatgcttgg ctctggaatg ccagaactac aatcttttga tgacattgca   3060
tatatccgaa agactctagc cttgacaaaa actgagcaag aagctttgga atatttcaca   3120
aagcaaatga atgatgcaca tcatggtgga tggacgacaa aaatggattg gatcttccac   3180
accatcaagc agcatgcttt gaactga                                        3207
```

<210> SEQ ID NO 107
<211> LENGTH: 1068
<212> TYPE: PRT
<213> ORGANISM: Mus musculus

<400> SEQUENCE: 107

```
Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Val Thr Ile Lys His Glu
        35                  40                  45

Leu Phe Arg Glu Ala Arg Lys Tyr Pro Leu His Gln Leu Leu Gln Asp
    50                  55                  60

Glu Thr Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Val Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Ile Asp Ser Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
```

```
                340             345             350
Lys Ile Tyr Val Arg Thr Gly Ile Tyr His Gly Gly Glu Pro Leu Cys
            355             360             365

Asp Asn Val Asn Thr Gln Arg Val Pro Cys Ser Asn Pro Arg Trp Asn
            370             375             380

Glu Trp Leu Asn Tyr Asp Ile Tyr Ile Pro Asp Leu Pro Arg Leu Ala
385             390             395             400

Arg Leu Cys Leu Ser Ile Cys Ser Val Lys Gly Arg Lys Gly Ala Lys
            405             410             415

Glu Glu His Cys Pro Leu Ala Trp Gly Asn Ile Asn Leu Phe Asp Tyr
            420             425             430

Thr Asp Thr Leu Val Ser Gly Lys Met Ala Leu Asn Leu Trp Pro Val
            435             440             445

Pro His Gly Leu Glu Asp Leu Leu Asn Pro Ile Gly Val Thr Gly Ser
            450             455             460

Asn Pro Asn Lys Glu Thr Pro Cys Leu Glu Leu Glu Phe Asp Trp Phe
465             470             475             480

Ser Ser Val Val Lys Phe Pro Asp Met Ser Val Ile Glu Glu His Ala
            485             490             495

Asn Trp Ser Val Ser Arg Glu Ala Gly Phe Ser Tyr Ser His Thr Gly
            500             505             510

Leu Ser Asn Arg Leu Ala Arg Asp Asn Glu Leu Arg Glu Asn Asp Lys
            515             520             525

Glu Gln Leu Arg Ala Leu Cys Thr Arg Asp Pro Leu Ser Glu Ile Thr
            530             535             540

Glu Gln Glu Lys Asp Phe Leu Trp Ser His Arg His Tyr Cys Val Thr
545             550             555             560

Ile Pro Glu Ile Leu Pro Lys Leu Leu Leu Ser Val Lys Trp Asn Ser
            565             570             575

Arg Asp Glu Val Ala Gln Met Tyr Cys Leu Val Lys Asp Trp Pro Pro
            580             585             590

Ile Lys Pro Glu Gln Ala Met Glu Leu Leu Asp Cys Asn Tyr Pro Asp
            595             600             605

Pro Met Val Arg Ser Phe Ala Val Arg Cys Leu Glu Lys Tyr Leu Thr
            610             615             620

Asp Asp Lys Leu Ser Gln Tyr Leu Ile Gln Leu Val Gln Val Leu Lys
625             630             635             640

Tyr Glu Gln Tyr Leu Asp Asn Leu Leu Val Arg Phe Leu Leu Lys Lys
            645             650             655

Ala Leu Thr Asn Gln Arg Ile Gly His Phe Phe Phe Trp His Leu Lys
            660             665             670

Ser Glu Met His Asn Lys Thr Val Ser Gln Arg Phe Gly Leu Leu Leu
            675             680             685

Glu Ser Tyr Cys Arg Ala Cys Gly Met Tyr Leu Lys His Leu Asn Arg
            690             695             700

Gln Val Glu Ala Met Glu Lys Leu Ile Asn Leu Thr Asp Ile Leu Lys
705             710             715             720

Gln Glu Lys Lys Asp Glu Thr Gln Lys Val Gln Met Lys Phe Leu Val
            725             730             735

Glu Gln Met Arg Gln Pro Asp Phe Met Asp Ala Leu Gln Gly Phe Leu
            740             745             750

Ser Pro Leu Asn Pro Ala His Gln Leu Gly Asn Leu Arg Leu Glu Glu
            755             760             765
```

Cys Arg Ile Met Ser Ser Ala Lys Arg Pro Leu Trp Leu Asn Trp Glu
              770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
                820                 825                 830

Met Leu Pro Tyr Gly Cys Leu Ser Ile Gly Asp Cys Val Gly Leu Ile
                835                 840                 845

Glu Val Val Arg Asn Ser His Thr Ile Met Gln Ile Gln Cys Lys Gly
                850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
                900                 905                 910

Ile Gly Asp Arg His Asn Ser Asn Ile Met Val Lys Asp Asp Gly Gln
                915                 920                 925

Leu Phe His Ile Asp Phe Gly His Phe Leu Asp His Lys Lys Lys Lys
930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Tyr Thr Lys Thr Arg Glu
                965                 970                 975

Phe Glu Arg Phe Gln Glu Met Cys Tyr Lys Ala Tyr Leu Ala Ile Arg
                980                 985                 990

Gln His Ala Asn Leu Phe Ile Asn Leu Phe Ser Met Met Leu Gly Ser
                995                 1000                1005

Gly Met Pro Glu Leu Gln Ser Phe Asp Asp Ile Ala Tyr Ile Arg
            1010                1015                1020

Lys Thr Leu Ala Leu Asp Lys Thr Glu Gln Glu Ala Leu Glu Tyr
            1025                1030                1035

Phe Thr Lys Gln Met Asn Asp Ala His His Gly Gly Trp Thr Thr
            1040                1045                1050

Lys Met Asp Trp Ile Phe His Thr Ile Lys Gln His Ala Leu Asn
            1055                1060                1065

<210> SEQ ID NO 108
<211> LENGTH: 4326
<212> TYPE: DNA
<213> ORGANISM: Macaca mulatta

<400> SEQUENCE: 108
tctccctcgg cgccgccgcc gccgcccgcg gggctgggac ccgatgcggt tagagccgcg      60
gagcctggaa gagccccgag cgtttctgct ttgggacaac catacgtcta attctttaaa    120
gtagttttat atgtaaaacc tgcaaaaaat cagaacaatg cctccacgac catcatcagg    180
tgaactgtgg ggcatccact tgatgccccc aagaatccta gtagaatgtt tactaccaaa    240
tggaatgata gtgactttag aatgcctccg tgaggctaca ttaataacca taaagcatga    300
actatttaaa gaagcaagaa ataccccct ccatcaactt cttcaagatg aatcttctta    360
cattttcgta agtgttaccc aagaagcaga aaggagaa ttttttgatg aaacaagacg    420
actttgtgac cttcggcttt ttcaacccctt tttaaaagta attgaaccag taggcaaccg    480

```
tgaagaaaag atcctcaatc gagaaattgg ttttgctatt ggcatgccag tgtgtgaatt    540
tgatatggtt aaagatccag aagtacagga cttccgaaga aatattctga atgtttgtaa    600
agaagctgtg gatcttaggg atctcaattc acctcatagt agagcaatgt atgtctatcc    660
tccaaatgta gaatcttcgc cagaattgcc aaagcacata tataataaat tagataaagg    720
gcaaataata gtggtgattt gggtaatagt ttctccaaat aatgacaagc agaagtatac    780
tctgaaaatc aaccatgact gtgtaccaga acaagtaatt gctgaagcaa tcaggaaaaa    840
aactcgaagt atgttgctat cctctgaaca gctaaaactc tgtgttttag aatatcaggg    900
caagtatatt ttaaaagtgt gtggatgtga tgaatacttc ctagaaaaat atcctctgag    960
tcagtataag tatataagaa gctgtataat gcttgggagg atgcccaatt tgatgttgat   1020
ggctaaagaa agcctttatt ctcaactgcc aatggactgt tttacaatgc catcttattc   1080
cagacgcatt tccacagcta caccatatat gaatggagaa acatctacaa aatcccttg    1140 ggttataaat agtgcactca gaataaaaat tctttgtgca acctacgtga atgtaaatat   1200
tcgagacatt gataagatct atgttcgaac aggtatctac catggaggag aacccttatg   1260
tgacaatgtg aacactcaaa gagtaccttg ttccaatccc aggtggaatg aatggctgaa   1320
ttatgatata tacattcctg accttcctcg tgctgctcga ctttgccttt ccatttgctc   1380
tgttaaaggc cgaaagggtg ctaaagagga acactgtcca ttggcatggg aaatataaa    1440 cttgtttgat tacacagaca ctctagtatc tggaaaaatg gctttgaatc tttggccagt   1500
acctcatgga ttagaagatt tgctgaaccc tattggtgtt actggatcaa atccaaataa   1560
agaaactcca tgcttagagt tggagtttga ctggttcagc agtgtggtaa agttcccaga   1620
tatgtcagtg attgaagagc atgccaattg gtctgtgtcc cgagaagcag gatttagcta   1680
ttcccacgca ggactgagta acaggctagc tagagacaat gaattaaggg aaaatgacaa   1740
agaacagctc aaagcaattt ctacacgaga tcctctctct gaaatcactg agcaggagaa   1800
agattttctg tggagccaca gacactattg tgtaactatc cccgaaattc tacccaaatt   1860
gcttctgtct gttaaatgga attctagaga tgaagtagcc cagatgtatt gcttggtaaa   1920
agactggcct ccaatcaaac ctgaacaggc tatggaactt ctggactgta attacccaga   1980
tcctatggtt cgaggttttg ctgttcggtg cttggaaaaa tatttaacag atgacaaact   2040
ttctcagtat ttaattcagc tagtacaggt cctaaaatat gaacaatatt tggataactt   2100
gcttgtgaga tttttactga agaaagcatt gactaatcaa aggattgggc acttttctt    2160 ttggcattta aaatctgaga tgcacaataa aacagttagc cagaggtttg gcctgctttt   2220
ggagtcctat tgtcgtgcat gtgggatgta tttgaagcac ctgaataggc aagtcgaggc   2280
aatggaaaag ctcattaact taactgacat tctcaaacag gagaaaaagg atgaaacaca   2340
aaaggtacag atgaagtttt tagttgagca aatgaggcga ccagatttca tggatgctct   2400
gcagggcttt ctatctcctc taaaccctgc tcatcaacta ggaaatctca ggcttgaaga   2460
gtgtcgaatt atgtccctctg caaaaaggcc actgtggttg aattgggaga acccagacat   2520
catgtcagag ttactgtttc agaacaatga gatcatcttt aaaaatgggg atgatttacg   2580
gcaagatatg ctaacacttc aaattattcg tattatggaa aatatctggc aaaatcaagg   2640
tcttgatctt cgaatgttac cttatggttg tctgtcaatc ggtgactgtg tgggacttat   2700
tgaggtggtg cgaaattctc acactattat gcaaattcag tgcaaaggcg cttgaaagg    2760 tgcactgcag ttcaacagcc acactctaca tcagtggctc aaagacaaga acaaaggaga   2820
aatatatgat gcagccattg acctgttta cacgttcatgt gctggatatt gtgtcgctac   2880
```

```
cttcattctg ggaattggag atcgtcacaa tagtaacatc atggtgaaag acgatggaca      2940
actgtttcat atagattttg dcacttttt ggatcacaag aagaaaaaat ttggctataa      3000
acgagaacgt gtgccatttg ttttgacaca ggatttctta atagtgatta gtaaaggagc      3060
ccaagaatgc acaaagacaa gagaatttga gaggtttcag gagatgtgtt acaaggctta      3120
tctagctatt cgacagcatg ccaatctctt cataaatctt ttctcaatga tgcttggctc      3180
tggaatgcca gaactacaat cttttgatga cattgcatac attcgaaaga ccctagcctt      3240
agataaaact gagcaagagg ctttggaata tttcatgaaa caaatgaatg atgcacatca      3300
tggtggctgg acaacaaaaa tggattggat cttccacaca attaaacagc atgcattgaa      3360
ctgaaaagat aactgagaaa atgaaagctc actctctgga ttccacactg cactgttaat      3420
aactatcagc aggcaaagac cgattgcata ggaattgcac aatccatgaa cagcattaga      3480
atttacagca agaacagaaa taaaatacta tataatttaa tgtaaacgca aacagggttt      3540
gatagcactt aaactagttc atttcacaat taagctttag aataatgcgc aatttcatgt      3600
tatgccttaa gtccaaaaag gtaaactttg aagattgttt gtatcttttt ttaaaaaaca      3660
aaacaaaaca aaaatcccca aaatatatag aaatgatgga gaaggaaaaa tgatgttttt      3720
ttttgtcttg caaatgttct atgttttgaa atgtggacac aacaaaagct gttattgttt      3780
taggtgtaag taaactggag tttatgttaa attacattaa gattgaaaaa gaatgaaaat      3840
ttcttatttt tccattgctg ttcaatttat agtttgagtg ggttttgac tccttgttta      3900 atgaagaaaa atgcttgggg tggaagggac tcttgagatt tcaccagaga cttttctctt      3960
ttaataaatc aaacctttg atgatttgag gtcttatctg cagttttgga agcagtcaca      4020
aatgagacct gttataaggt ggtattttt tttttttct ggacagtatt taaaggattt      4080
tatttcccag ggaaattctg ggctcccaca gagtttaaaa aaaaaaaaaa aaaaaaatca      4140
tagaaaaaga atgaacagga atagttctta ttccaaaatt gtacagtatt caccttaagt      4200 tgatttttt ctccttttgc agttgaactg aatacatttt tcatgcatgt tttccaaaaa      4260
atagaagtat taatgttatt aaaaagatta ttttttttat taaaggctat ttatattata      4320
gaaact                                                                4326

<210> SEQ ID NO 109
<211> LENGTH: 1068
<212> TYPE: PRT
<213> ORGANISM: Macaca mulatta

<400> SEQUENCE: 109

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
                20                  25                  30

Thr Leu Glu Cys Leu Arg Glu Ala Thr Leu Ile Thr Ile Lys His Glu
            35                  40                  45

Leu Phe Lys Glu Ala Arg Lys Tyr Pro Leu His Gln Leu Leu Gln Asp
        50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
                100                 105                 110
```

-continued

```
Leu Asn Arg Glu Ile Gly Phe Ala Ile Gly Met Pro Val Cys Glu Phe
            115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Glu Ile Thr
530                 535                 540
```

```
Glu Gln Glu Lys Asp Phe Leu Trp Ser His His Tyr Cys Val Thr
545                 550                 555                 560

Ile Pro Glu Ile Leu Pro Lys Leu Leu Leu Ser Val Lys Trp Asn Ser
            565                 570                 575

Arg Asp Glu Val Ala Gln Met Tyr Cys Leu Val Lys Asp Trp Pro Pro
                580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
```

```
            965                 970                 975
Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                1005

Gly Met  Pro Glu Leu Gln Ser  Phe Asp Asp Ile Ala  Tyr Ile Arg
    1010                 1015                1020

Lys Thr  Leu Ala Leu Asp Lys  Thr Glu Gln Glu Ala  Leu Glu Tyr
    1025                 1030                1035

Phe Met  Lys Gln Met Asn Asp  Ala His His Gly Gly  Trp Thr Thr
    1040                 1045                1050

Lys Met  Asp Trp Ile Phe His  Thr Ile Lys Gln His  Ala Leu Asn
    1055                 1060                1065
```

```
<210> SEQ ID NO 110
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 110
cacggaggca ttctaaagtc acta                                           24

<210> SEQ ID NO 111
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 111
aaaaattctt ccctttctgc ttct                                           24

<210> SEQ ID NO 112
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 112
aggatagaca tacattgctc tact                                           24

<210> SEQ ID NO 113
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
```

```
<222> LOCATION: (1)..(24)
<223> OTHER INFORMATION: nucleotide or nucleotide analogues - optionally
      phosphorothioate

<400> SEQUENCE: 113
aatatacttg ccctgatatt ctaa                                            24

<210> SEQ ID NO 114
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 114
ttgtcacata agggttctcc tcca                                            24

<210> SEQ ID NO 115
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 115
attcagccat tcattccacc tggg                                            24

<210> SEQ ID NO 116
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 116
gatccagtaa caccaatagg gttc                                            24

<210> SEQ ID NO 117
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 117
gtcaaactcc aactctaagc atgg                                            24

<210> SEQ ID NO 118
<211> LENGTH: 24
<212> TYPE: DNA
```

```
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 118
ttaacagaca gaagcaattt gggt                                              24

<210> SEQ ID NO 119
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 119
tgttttattg tgcatctcag attt                                              24

<210> SEQ ID NO 120
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 120
ttttgcagag gacataattc gaca                                              24

<210> SEQ ID NO 121
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 121
acatgatgtc tgggttctcc caat                                              24

<210> SEQ ID NO 122
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 122 tttttcttc ttgtgatcca aaaa                                               24
```

```
<210> SEQ ID NO 123
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 123
tattaagaaa tcctgtgtca aaac                                              24

<210> SEQ ID NO 124
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 124
cacatctcct gaaacctctc aaat                                              24

<210> SEQ ID NO 125
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 125
cagtgatttt agagagagga tctc                                              24

<210> SEQ ID NO 126
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 126
gctcagtgat tttagagaga ggat                                              24

<210> SEQ ID NO 127
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
```

-continued

```
      phosphorothioate

<400> SEQUENCE: 127
tttctcctgc ttagtgattt caga                                              24

<210> SEQ ID NO 128
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 128
atctttctcc tgcttagtga tttc                                              24

<210> SEQ ID NO 129
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 129
tccagccacc atgacgtgca tcat                                              24

<210> SEQ ID NO 130
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 130
agccaccatg acgtgcatca ttca                                              24

<210> SEQ ID NO 131
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 131
cagtgatttc agagagagga tctc                                              24

<210> SEQ ID NO 132
<211> LENGTH: 24
<212> TYPE: DNA
<213> ORGANISM: artificial
<220> FEATURE:
```

```
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 132
gctcagtgat ttcagagaga ggat                                              24

<210> SEQ ID NO 133
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 133
tttctcctgc tcagtgattt caga                                              24

<210> SEQ ID NO 134
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 134
atctttctcc tgctcagtga tttc                                              24

<210> SEQ ID NO 135
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 135
tccagccacc atgatgtgca tcat                                              24

<210> SEQ ID NO 136
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate

<400> SEQUENCE: 136
agccaccatg atgtgcatca ttca                                              24
```

```
<210> SEQ ID NO 137
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-8-3 LNA Gapmer - fully phosphorothioate

<400> SEQUENCE: 137
attttagaga gagg                                                     14

<210> SEQ ID NO 138
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 138
ttttagagag ag                                                       12

<210> SEQ ID NO 139
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-8-3 LNA Gapmer - fully phosphorothioate

<400> SEQUENCE: 139
gtgattttag agag                                                     14

<210> SEQ ID NO 140
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 140
tgattttaga ga                                                       12

<210> SEQ ID NO 141
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-8-3 LNA Gapmer - fully phosphorothioate

<400> SEQUENCE: 141
cctgcttagt gatt                                                     14
```

```
<210> SEQ ID NO 142
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 142
ctgcttagtg at                                                              12

<210> SEQ ID NO 143
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-8-3 LNA Gapmer - fully phosphorothioate

<400> SEQUENCE: 143
tctcctgctt agtg                                                            14

<210> SEQ ID NO 144
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 144
ctcctgctta gt                                                              12

<210> SEQ ID NO 145
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-8-3 LNA Gapmer - fully phosphorothioate

<400> SEQUENCE: 145
ccaccatgac gtgc                                                            14

<210> SEQ ID NO 146
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 146
caccatgacg tg                                                              12
```

```
<210> SEQ ID NO 147
<211> LENGTH: 14
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(14)
<223> OTHER INFORMATION: 3-8-3 LNA Gapmer - fully phosphorothioate

<400> SEQUENCE: 147
ccatgacgtg catc                                                       14

<210> SEQ ID NO 148
<211> LENGTH: 12
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(12)
<223> OTHER INFORMATION: 2-8-2 LNA Gapmer - fully phosphorothioate

<400> SEQUENCE: 148
catgacgtgc at                                                         12

<210> SEQ ID NO 149
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate
<220> FEATURE:
<221> NAME/KEY: misc_feature
<222> LOCATION: (13)..(13)
<223> OTHER INFORMATION: n is a, c, g, or t

<400> SEQUENCE: 149
gctcagtgat ttnagagaga ggat                                            24

<210> SEQ ID NO 150
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate
<220> FEATURE:
<221> NAME/KEY: misc_feature
<222> LOCATION: (12)..(12)
<223> OTHER INFORMATION: n is a, c, g, or t

<400> SEQUENCE: 150
tttctcctgc tnagtgattt caga                                            24

<210> SEQ ID NO 151
<211> LENGTH: 16
<212> TYPE: DNA
<213> ORGANISM: artificial
<220> FEATURE:
<223> OTHER INFORMATION: LNA oligomer Sequence/oligomer Sequence motif
```

```
<220> FEATURE:
<221> NAME/KEY: misc_feature
<222> LOCATION: (1)..(16)
<223> OTHER INFORMATION: nucleotide or nucleotide analogues - optionally
      phosphorothioate
<220> FEATURE:
<221> NAME/KEY: misc_feature
<222> LOCATION: (6)..(6)
<223> OTHER INFORMATION: n is a, c, g, or t

<400> SEQUENCE: 151
gatttnagag agagga                                                       16

<210> SEQ ID NO 152
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate
<220> FEATURE:
<221> NAME/KEY: misc_feature
<222> LOCATION: (9)..(9)
<223> OTHER INFORMATION: n is a, c, g, or t

<400> SEQUENCE: 152
agtgatttna gagaga                                                       16

<210> SEQ ID NO 153
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate
<220> FEATURE:
<221> NAME/KEY: misc_feature
<222> LOCATION: (15)..(15)
<223> OTHER INFORMATION: n is a, c, g, or t

<400> SEQUENCE: 153
atctttctcc tgctnagtga tttc                                              24

<210> SEQ ID NO 154
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate
<220> FEATURE:
<221> NAME/KEY: misc_feature
<222> LOCATION: (10)..(10)
<223> OTHER INFORMATION: n is a, c, g, or t

<400> SEQUENCE: 154
cagtgatttn agagagagga tctc                                              24

<210> SEQ ID NO 155
<211> LENGTH: 16
```

```
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate
<220> FEATURE:
<221> NAME/KEY: misc_feature
<222> LOCATION: (8)..(8)
<223> OTHER INFORMATION: n is a, c, g, or t

<400> SEQUENCE: 155
tcctgctnag tgattt                                                    16

<210> SEQ ID NO 156
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate
<220> FEATURE:
<221> NAME/KEY: misc_feature
<222> LOCATION: (11)..(11)
<223> OTHER INFORMATION: n is a, c, g, or t

<400> SEQUENCE: 156
ttctcctgct nagtga                                                    16

<210> SEQ ID NO 157
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate
<220> FEATURE:
<221> NAME/KEY: misc_feature
<222> LOCATION: (12)..(12)
<223> OTHER INFORMATION: n is a, c, g, or t

<400> SEQUENCE: 157
agccaccatg angtgcatca ttca                                           24

<210> SEQ ID NO 158
<211> LENGTH: 24
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(24)
<223> OTHER INFORMATION: nucleotide or nucleotide analogues - optionally
      phosphorothioate
<220> FEATURE:
<221> NAME/KEY: misc_feature
<222> LOCATION: (15)..(15)
<223> OTHER INFORMATION: n is a, c, g, or t

<400> SEQUENCE: 158
tccagccacc atgangtgca tcat                                           24
```

```
<210> SEQ ID NO 159
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate
<220> FEATURE:
<221> NAME/KEY: misc_feature
<222> LOCATION: (11)..(11)
<223> OTHER INFORMATION: n is a, c, g, or t

<400> SEQUENCE: 159
gccaccatga ngtgca                                                   16

<210> SEQ ID NO 160
<211> LENGTH: 16
<212> TYPE: DNA
<213> ORGANISM: artificial
<220> FEATURE:
<223> OTHER INFORMATION: LNA oligomer Sequence/oligomer Sequence motif
<220> FEATURE:
<221> NAME/KEY: misc_feature
<222> LOCATION: (1)..(16)
<223> OTHER INFORMATION: nucleotide or nucleotide analogues - optionally
      phosphorothioate
<220> FEATURE:
<221> NAME/KEY: misc_feature
<222> LOCATION: (8)..(8)
<223> OTHER INFORMATION: n is a, c, g, or t

<400> SEQUENCE: 160
accatgangt gcatca                                                   16
```